(12) United States Patent
Deppe et al.

(10) Patent No.: US 8,841,459 B2
(45) Date of Patent: *Sep. 23, 2014

(54) 3-ARYLAMINO PYRIDINE DERIVATIVES

(71) Applicant: Merck Serono SA, Vaud (CH)

(72) Inventors: Holger Deppe, Basel (CH); Matthias Schwarz, Geneve (CH); Ulrich Abel, Heidelberg (DE); Achim Feurer, Auggen (DE); Ulrich Grädler, Heidelberg (DE); Kerstin Otte, Heidelberg (DE); Renate Sekul, Ladenburg (DE); Meinolf Thiemann, Schriesheim (DE); Andreas Goutopoulos, Boston, MA (US); Xuliang Jiang, Braintree, MA (US)

(73) Assignee: Merck Serono SA, Vaud (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/940,065

(22) Filed: Jul. 11, 2013

(65) Prior Publication Data

US 2014/0051686 A1 Feb. 20, 2014

Related U.S. Application Data

(60) Division of application No. 13/472,721, filed on May 16, 2012, now Pat. No. 8,524,911, which is a continuation of application No. 13/112,490, filed on May 20, 2011, now Pat. No. 8,198,457, which is a division of application No. 11/665,651, filed as application No. PCT/EP2005/011257 on Oct. 19, 2005, now Pat. No. 7,956,191.

(30) Foreign Application Priority Data

Oct. 20, 2004 (EP) ..................... 04024967

(51) Int. Cl.
| | |
|---|---|
| C07D 213/72 | (2006.01) |
| C07D 213/46 | (2006.01) |
| A01N 43/58 | (2006.01) |
| C07D 405/12 | (2006.01) |
| C07D 213/79 | (2006.01) |
| C07D 401/12 | (2006.01) |
| C07D 295/13 | (2006.01) |
| C07D 213/81 | (2006.01) |
| C07D 295/125 | (2006.01) |
| C07D 295/32 | (2006.01) |
| C07D 213/89 | (2006.01) |

(52) U.S. Cl.
CPC .......... *C07D 405/12* (2013.01); *C07D 213/79* (2013.01); *C07D 401/12* (2013.01); *C07D 295/13* (2013.01); *C07D 213/81* (2013.01); *C07D 295/125* (2013.01); *C07D 295/32* (2013.01); *C07D 213/89* (2013.01)
USPC ............ 546/314; 546/315; 514/247

(58) Field of Classification Search
USPC ............... 546/310, 312, 315; 514/247
See application file for complete search history.

(56) References Cited

U.S. PATENT DOCUMENTS

| | | | |
|---|---|---|---|
| 4,959,378 A | 9/1990 | Allen et al. | |
| 5,525,625 A | 6/1996 | Bridges et al. | |
| 7,956,191 B2 | 6/2011 | Abel et al. | |
| 8,198,457 B2 * | 6/2012 | Abel et al. | 546/310 |
| 8,524,911 B2 | 9/2013 | Abel et al. | |

FOREIGN PATENT DOCUMENTS

| | | |
|---|---|---|
| JP | 6 222 3173 | 10/1987 |
| WO | WO 98/43960 | 10/1998 |
| WO | WO 99/01421 | 1/1999 |
| WO | WO 99/01426 | 1/1999 |
| WO | WO 2000/37141 | 6/2000 |
| WO | WO 00/041505 | 7/2000 |
| WO | WO 00/41994 | 7/2000 |
| WO | WO 00/42002 | 7/2000 |
| WO | WO 00/42003 | 7/2000 |
| WO | WO 00/42022 | 7/2000 |
| WO | WO 00/42029 | 7/2000 |

(Continued)

OTHER PUBLICATIONS

Bachman, B.G., and Barker, R.S., "Derivatives of the Pyridoquinolines," Contribution from the Purdue Research Foundation and the Department of Chemistry, Purdue University. Ph.D. thesis of R.S. Barker, Sep. 1948.

(Continued)

*Primary Examiner* — Nizal Chandrakumar
(74) *Attorney, Agent, or Firm* — Hamilton, Brook, Smith & Reynolds, P.C.

(57) ABSTRACT

The invention provides novel, substituted 3-arylamino pyridine compounds

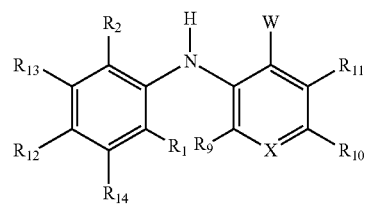

X = N; NO pharmaceutically acceptable salts, solvates and prodrug compounds thereof, wherein W, R1, R2, R9, R10, R11, R12, R13, R14 are as defined in the specification. Such compounds are MEK inhibitors and useful in the treatment of hyperproliferative diseases, such as cancer, restenosis and inflammation. Also disclosed is the use of such compounds in the treatment of hyperproliferative diseases in mammals, especially humans, and pharmaceutical compositions containing such compounds.

18 Claims, No Drawings

(56) References Cited

FOREIGN PATENT DOCUMENTS

| | | |
|---|---|---|
| WO | WO 00/68201 | 11/2000 |
| WO | WO 01/05391 | 1/2001 |
| WO | WO 01/68619 | 9/2001 |
| WO | WO 01/90074 | 11/2001 |
| WO | WO 02/06213 | 1/2002 |
| WO | WO 02/083622 | 10/2002 |
| WO | WO 03/027085 | 4/2003 |
| WO | WO 03/035626 | 5/2003 |
| WO | WO 03/077855 | 9/2003 |
| WO | WO 03/077914 | 9/2003 |
| WO | WO 03/101988 | 12/2003 |
| WO | WO 2004/005284 | 1/2004 |
| WO | WO 2004/052280 | 6/2004 |
| WO | WO 2004/056789 | 7/2004 |
| WO | WO 2004/091480 | 10/2004 |

OTHER PUBLICATIONS

Carter, A., et al., "A Constitutive Active MEK—> ERK Pathway Negatively Regulates NF-κB-dependent Gene Expression by Modulating TATA-binding Protein Phosphorylation," *The Journal of Biological Chemistry*, 275(36): 27858-27864 (2000).

Chang, F., et al., "Signal Transduction Mediated by the Ras/Raf/MEK/ERK Pathway From Cytokine Receptors to Transcription Factors: Potential Targeting for Therapeutic Intervention," *Leukemia*, 17: 1263-1293 (2003).

Crews, C., et al., "The Primary Structure of MEK, a Protein Kinase That Phosphorylates the ERK Gene Product," *Science*, 258: 478-480 (1992).

Davies, H., et al., "Mutations of the BRAF Gene in Human Cancer," *Nature*, 417: 949-954 (2002).

Dudley, D., et al., "A Synthetic Inhibitor of the Mitogen-activated Protein Kinase Cascade," *Proc. National Academy of Science U.S.A.*, 92: 7686-7689 (1995).

Huang, W., et al., "Biochemical and Biological Analysis of Mek 1 Phosphorylation Site Mutants," *Molecular Biology of the Cell*, 6: 237-245 (1995).

Kohl, N., et al., "Selective Inhibition of ras-Dependent Transformation by a Farnesyltransferase Inhibitor," *Science*, 260: 1934-1937 (1993).

Lee, J., et at., "A Protein Kinase Involved in The Regulation of Inflammatory Cytokine Biosynthesis," *Nature*, 372: 739-746 (1994).

Lee, P., et al., "ARRY-142886, A Potent and Selective MEK Inhibitor: III) Efficacy in Murine Xenograft Models Correlates With Decreased ERK Phosphorylation," *Proceedings of the American Association of Cancer Research*, 45: Abs 3890 (2004).

Lewis, T., et al., "Signal Transduction Through MAP Kinase Cascades," *In Advances in Cancer Research*, George F. Vande Woude, et al., eds. (London: Academic Press), pp. 49-139 (1998).

Lin, A., et al., "Premature Senescence Involving p. 53 and p. 16 is Activated in Response to Constitutive MEK/MAPK Mitogenic Signaling," *Genes & Development*, 12: 3008-3019 (1998).

McCubrey, J., et al., "Differential Effects of Viral and Cellular Oncogenes on the Growth Factor-Dependency of Hematopoietic Cells," *International Journal of Oncology*, 7(2): 295-310 (1995).

McInnes, C., "Protein Kinases: Addressing the Challenges Across the Kinome—IIR's Second Annual Conference (Part 1), Kinase Drug Discovery and Disease Biology, Amsterdam, the Netherlands," (Reference No. RF511413) Amsterdam, the Netherlands: IDDB—Meeting Report (2003).

McInnes, C., "Protein Kinases: Addressing the Challenges Across the Kinome—IIR's Second Annual Conference (Part II), Clinical Update, New Therapies and New Technologies, Amsterdam, the Netherlands," (Reference No. RF511633) Amsterdam, the Netherlands: IDDB—Meeting Report (2003).

Orlova, N., et al., "Interaction of Polyfluorosubstituted Pyridine and Naphthalene Carbonic Acids With Bromomagnezylaniline," *Sibirskogo Otdeleniya Akademii Nauk SSR Seriya Khimicheskikh Nauk*, 17: 93-97 (1984).

Sherlock, M., et al., "Antiallergy Agents. 1. Substituted 1,8-Naphthyridin-2(1H)-ones as Inhibitors of SRS-A Release," *Journal of Medicinal Chemistry*, 31: 2108-2121 (1988).

Steelman, L., et al., "JAKISTAT, Raf/MEK/ERK, P13K/Akt and BCR-ABL in Cell Cycle Progression and Leukemogenesis," *Leukemia*, 18: 189-218 (2004).

Stirewalt, D., et al., "FLT3, RAS, and TP53 Mutations in Elderly Patients With Acute Myeloid Leukemia," *Blood*, 97(11): 3589-3595 (2001).

Swanton, c., et al., "New Targets and Innovative Strategies in Cancer Treatment: One Year of Progress, Nice, France," (Reference No. RF524997) France: IDDB—Meeting Report (2003).

Wallace, E., et at., "Preclinical Development of ARRY-142886, A Potent and Selective MEK Inhibitor," *Proceedings of the American Association of Cancer Research*, 45: Abs 3891 (2004).

Waterhouse, D., et al., "A Phase 2 Study of an Oral MEK Inhibitor, CI-1040, in Patients With Advanced Nonsmall-cell Lung, Breast, Colon, or Pancreatic Cancer," *Proceedings of the American Society for Clinical Oncology*, 22: Abs 816 (2003).

Yeh, T., et at., "ARRY-I42886, A Potent and Selective MEK Inhibitor: II) Potency Against Cellular MEK Leads to Inhibition of Cellular Proliferation and Induction of Apoptosis in Cell Lines With Mutant Ras or B-Raf," *Proceedings of the American Association of Cancer Research*, 45: Abs 3889 (2004).

Zhu, P., et al., "Studies of Antimalarials: Synthesis of Derivatives of Benzo[b][1,7]Naphthyridine With Aminophenol Mannich Base," *Gongye*, 19(2): 55-57 (1988).

International Search Report, PCT/EP2005/011257, "3-Arylamino Pyridine Derivatives" mailed Feb. 24, 2006.

Written Opinion of the International Searching Authority, PCT/EP2005/011257, "3-Arylamino Pyridine Derivatives" mailed Feb. 24, 2006.

Talik, STN Accession No. 1953 :435518 *Abstract of Roczniki Chemii* (1962), 36, 1465-1475.

Brandenburg, J. et al., "Bicyclic Oxalic Amidines as Building Blocks for Highly Substituted 2,2'-Bipyridines and Benzene Derivatives", *Journal für praktishe Chemie Chemiker-Zeitung*, 338: 430-435 (1996).

Evans, D., et at., "Substituted Anilinopyridine Carboxylic Acids with Antiinflammatory Activity", *Med. Chem.*, 10(3): 428-431 (1967).

Gawinecki, R, et at., "Fragmentation of o-Nitrodiarylamines on Electron Impact: Formation of Carbazole Radical Cations", *Organic Mass Spectrometry*, 27: 39-43 (1992).

Julemont, F. et al., "Design, Synthesis, and Pharmacological Evaluation of Pyridinic Analogues of Nimesulide as Cyclooxygenase-2 Selective Inhibitors", *J. Med. Chem.*, 47: 6749-6759 (2004).

Rasala, D., "$^1$H NMR Spectra of Substituted Aminopyridines", *Spectroscopy Letters*, 26(2): 227-235 (1993).

International Preliminary Report on Patentability, PCT/EP2005/011257, "3-Arylamino Pyridine Derivatives" issued Apr. 24, 2007.

* cited by examiner

3-ARYLAMINO PYRIDINE DERIVATIVES

RELATED APPLICATIONS

This application is a divisional of U.S. application Ser. No. 13/472,721 filed on May 16, 2012, now U.S. Pat. No. 8,524,911, issued on Sep. 3, 2013, which is a continuation of U.S. application Ser. No. 13/112,490, filed on May 20, 2011, now U.S. Pat. No. 8,198,457, issued on Jun. 12, 2012, which is a divisional of U.S. application Ser. No. 11/665,651, filed on Oct. 19, 2005, now U.S. Pat. No. 7,956,191, issued on Jul. 7, 2011, which is the U.S. National Stage of International Application No. PCT/EP2005/011257, filed on Oct. 19, 2005, published in English, which claims priority under 35 U.S.C. §119 or §365 to European Application No. 04024967.4, filed Oct. 20, 2004. The entire teachings of the above applications are incorporated herein by reference.

FIELD OF THE INVENTION

The invention relates to a series of substituted 3-arylamino pyridine derivatives that are useful in the treatment of hyperproliferative diseases, such as cancer and inflammation, in mammals. Also disclosed is the use of such compounds in the treatment of hyperproliferative diseases in mammals, especially humans, and pharmaceutical compositions containing such compounds.

SUMMARY OF THE RELATED ART

The Ras/Raf/MEK/ERK pathway is a central signal transduction pathway, which transmits signals from multiple cell surface receptors to transcription factors in the nucleus which regulate gene expression. This pathway is frequently referred to as the MAP kinase pathway as MAPK stands for mitogen-activated protein kinase indicating that this pathway can be stimulated by mitogens, cytokines and growth factors (Steelman et al., Leukemia 2004, 18, 189-218). Depending upon the stimulus and cell type, this pathway can transmit signals, which result in the prevention or induction of apoptosis or cell cycle progression. The Ras/Raf/MEK/ERK pathway has been shown to play important roles in cell proliferation and the prevention of apoptosis. Aberrant activation of this pathway is commonly observed in malignantly transformed cells. Amplification of ras proto-oncogenes and activating mutations that lead to the expression of constitutively active Ras proteins are observed in approximately 30% of all human cancers (Stirewalt et al., Blood 2001, 97, 3589-95). Mutated, oncogenic forms of Ras are found in 50% of colon and >90% pancreatic cancers as well as many other types of cancers (Kohl et al., Science 1993, 260, 1834-1837). The effects of Ras on proliferation and tumorigenesis have been documented in immortal cell lines (McCubrey et al., Int J Oncol 1995, 7, 295-310). bRaf mutations have been identified in more than 60% of malignant melanoma (Davies, H et al., Nature 2002, 417, 949-954). Given the high level of mutations that have been detected at Ras, this pathway has always been considered a key target for therapeutic intervention (Chang et al., Leukemia 2003, 17, 1263-93).

The Ras/Raf/MEK/ERK signaling pathway can exert proliferative or antiproliferative effects through downstream transcription factor targets including NF-κB, CREB, Ets-1, AP-1 and c-Myc. ERKs can directly phosphorylate Ets-1, AP-1 and c-Myc, which lead to their activation. Alternatively, ERKs can phosphorylate and activate a downstream kinase target RSK, which then phosphorylates and activates transcription factors, such as CREB. These transcription factors induce the expression of genes important for cell cycle progression, for example, Cdks, cyclins, growth factors, and apoptosis prevention, for example, antiapoptotic Bcl-2 and cytokines. Overall, treatment of cells with growth factors leads to the activation of ERKs which results in proliferation and, in some cases, differentiation (Lewis et al., Adv. Cancer Res, 1998, 74, 49-139).

MEK proteins are the primary downstream targets of Raf. The MEK family of genes consists of five genes: MEK1, MEK2, MEK3, MEK4 and MEK5. This family of dual-specificity kinases has both serine/threonine and tyrosine kinase activity. The structure of MEK consists of an amino-terminal negative regulatory domain and a carboxy-terminal MAP kinase-binding domain, which is necessary for binding and activation of ERKs. Deletion of the regulatory MEK1 domain results in constitutive MEK1 and ERK activation (Steelman et al., Leukemia 2004, 18, 189-218).

MEK1 is a 393-amino-acid protein with a molecular weight of 44 kDa (Crews et al., Science 1992, 258, 478-80). MEK1 is modestly expressed in embryonic development and is elevated in adult tissue with the highest levels detected in brain tissue. MEK1 requires phosphorylation of S218 and S222 for activation, and substitution of these residues with D or glutamic acid (E) led to an increase in activity and foci formation in NIH3T3 cells (Huang et al., Mol Biol Cell, 1995, 6, 237-45). Constitutive activity of MEK1 in primary cell culture promotes senescence and induces p53 and p16$^{INK4a}$, and the opposite was observed in immortalized cells or cells lacking either p53 or p16$^{INK4a}$ (Lin et al., Genes Dev, 1998, 12, 3008-3019). Constitutive activity of MEK1 inhibits NF-κB transcription by negatively regulating p38$^{MAPK}$ activity (Carter et al., J Biol Chem 2000, 275, 27858-64). The main physiological substrates of MEK are the members of the ERK (extracellular signal-regulated kinase) or MAPK (mitogen activated protein kinase) family of genes. Aberrant expression of MEK1 has been detected in many different types of cancer, and mutated forms of MEK1 will transform fibroblast, hematopoietic and other cell types.

Constitutive activation of MEK1 results in cellular transformation. It therefore represents a likely target for pharmacological intervention in proliferative and inflammatory diseases (Lee et al., Nature 1994, 372, 739-746; Dudley et al., Proc. Natl. Acad. Sci. U.S.A. 1995, 92, 7686-7689).

Useful inhibitors of MEK have been developed that show potential therapeutic benefit in several studies. For example, small molecule MEK inhibitors have been shown to inhibit human tumor growth in nude mouse xenografts (Yeh, T. et al, *Proceedings of the American Association of Cancer Research* 2004, 45, Abs 3889 and Lee, P. et al., *Proceedings of the American Association of Cancer Research* 2004, 45, Abs 3890). MEK inhibitors also entered clinical trials, i.e. ARRY142886 (Wallace, E. et al, *Proceedings of the American Association of Cancer Research* 2004, 45, Abs 3891), PD-0325901 (Swanton C, Johnston S *IDDB MEETING REPORT* 2003, Feb. 13-1) and PD-184352 (Waterhouse et al., *Proceedings of the American Society for Clinical Oncology* 2003, 22, Abs 816).

Compounds suitable as MEK inhibitors are also disclosed in U.S. Pat. No. 5,525,625; WO 98/43960; WO 99/01421; WO 99/01426; WO 00/41505; WO 00/42002; WO 00/42003; WO 00/41994; WO 00/42022; WO 00/42029; WO 00/68201; WO 01/68619; WO 02/06213; WO 03/077855; WO03/077914; WO2004/005284; WO2004/056789.

However, PD-184352 was lacking efficacy in clinical phase II trials. Tumors were much less responsive, as no partial responses and only a few patients with stable disease were observed. As a result, the clinical trials of this molecule were suspended (McInnes C *IDDB MEETING REPORT* 2003). PD-184352 was limited by poor solubility, high metabolic clearance and low bioavailability. This exemplifies the need for novel MEK inhibitors with superior pharmacological properties.

DESCRIPTION OF THE INVENTION

In view of the foregoing it is the object of the present invention to provide novel MEK inhibitors useful in the treatment of hyperproliferative diseases related to the hyperactivity of MEK as well as diseases modulated by the MEK cascade, such as cancer and inflammation, in mammals with superior pharmacological properties both with respect to their activities as well as their solubility, metabolic clearance and bioavailability characteristics.

As a result, this invention provides novel, substituted 3-arylamino pyridine derivatives and pharmaceutically acceptable salts, solvates or prodrugs thereof, that are MEK inhibitors and useful in the treatment of the above mentioned diseases.

The compounds are defined by Formula (I):

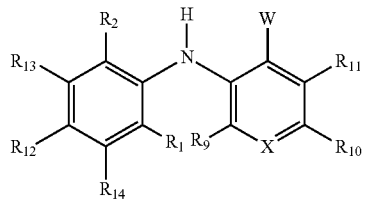

Formula (I)

a pharmaceutically acceptable salt, solvate or prodrug thereof,
wherein:
$R_1$, $R_2$, $R_9$, $R_{10}$, $R_{11}$ $R_{12}$, $R_{13}$ and $R_{14}$ are independently selected from hydrogen, halogen, cyano, nitro, azido, —$OR_3$, —$C(O)R_3$, —$C(O)OR_3$, —$NR_4C(O)OR_6$, —$OC(O)R_3$, —$NR_4S(O)_jR_6$, —$S(O)_jNR_3R_4$, —$S(O)_jNR_4C(O)R_3$, —$C(O)NR_4S(O)_jR_6$, $S(O)_jR_6$, —$NR_4C(O)R_3$, —$C(O)NR_3R_4$, —$NR_5C(O)NR_3R_4$, —$NR_5C(NCN)NR_3R_4$, —$NR_3R_4$ and $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —$S(O)_j$ ($C_1$-$C_6$ alkyl), —$S(O)_j(CR_4R_5)_m$-aryl, aryl, arylalkyl, heteroaryl, heteroarylalkyl, heterocyclyl, heterocyclylalkyl, —$O(CR_4R_5)_m$-aryl, —$NR_4(CR_4R_5)_m$-aryl, —$O(CR_4R_5)_m$-heteroaryl, —$NR_4(CR_4R_5)_m$, heteroaryl, —$O(CR_4R_5)_m$-heterocyclyl, —$NR_4(CR_4R_5)_m$-heterocyclyl, and —$S(C_1$-$C_2$ alkyl) substituted with 1 to 5 F, where each alkyl, alkenyl, alkynyl, cycloalkyl, aryl, heteroaryl and heterocyclyl are substituted or unsubstituted;

$R_3$ is selected from hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, and heterocyclylalkyl, where each alkyl, alkenyl, alkynyl, cycloalkyl, aryl, heteroaryl and heterocyclyl is substituted or unsubstituted;

$R_4$ is selected from hydrogen or $C_1$-$C_6$ alkyl whereby alkyl may be substituted or unsubstituted; or $R_3$ and $R_4$ can be taken together with the atom to which they are attached to form a 4 to 10 membered heteroaryl or heterocyclic ring, each of which is substituted or unsubstituted;

$R_5$ is selected from hydrogen or $C_1$-$C_6$ alkyl whereby alkyl may be substituted or unsubstituted; or $R_4$ and $R_5$ can be taken together with the atom to which they are attached to form a 4 to 10 membered carbocyclic, heteroaryl or heterocyclic ring, each of which is substituted or unsubstituted;

$R_6$ is selected from trifluoromethyl; and $C_1$-$C_{10}$ alkyl, $C_3$-$C_{10}$ cycloalkyl, aryl, arylalkyl, heteroaryl, heteroarylalkyl, heterocyclyl, and heterocyclylalkyl, where each alkyl, cycloalkyl, aryl, heteroaryl and heterocyclyl substituted or unsubstituted;

W is selected from heteroaryl containing 1-4 heteroatoms or heterocyclyl containing 1-4 heteroatoms each of which is unsubstituted or substituted by 1 to 5 substituents $ZR_{15}$; or W is —$C(O)OR_{15}$, —$C(O)NR_4R_{15}$, —$C(O)NR_4OR_{15}$, —$C(O)(C_3$-$C_{10}$ cycloalkyl), —$C(O)(C_2$-$C_{10}$ alkyl), —$C(O)(aryl)$, —$C(O)(heteroaryl)$, —$C(O)(heterocyclyl)$, $S(O)_jNR_4R_{15}$, $S(O)_jNR_4OR_{15}$, —$S(O)_jNR_4C(O)R_{15}$, —$C(O)NR_4S(O)_jR_6$, —$C(O)NR_4NR_4R_{15}$, —$C(O)C(O)R_{15}$, —$C(O)CR'R''C(O)R_{15}$, —NR'R'', —NR'C(O)R', —NR'S(O)$_j$R', —NRC(O)NR'R'', NR'S(O)$_j$NR'R'', or —$C(O)NR_4NR_4C(O)R_{15}$;

Z is a bond, $NR_{16}$, O, $NR_{16}SO_2$ or S;

$R_{15}$ is independently selected from hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, and heterocyclylalkyl, where each alkyl, alkenyl, alkynyl, cycloalkyl, aryl, heteroaryl and heterocyclyl is substituted or unsubstituted;

$R_{16}$ is selected from hydrogen or $C_1$-$C_{10}$ alkyl, or $R_{15}$ and $R_{16}$ form together a 4 to 10 membered cyclic ring with 1 or 2 N atoms and optionally an O atom, said ring being substituted or unsubstituted;

X is N or N→O;

m is 0, 1, 2, 3, 4 or 5; and j is 1 or 2.

Preferred are compounds of Formula (II),

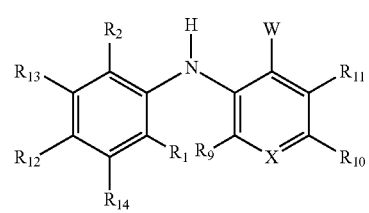

Formula (II)

a pharmaceutically acceptable salt, solvate or prodrug thereof,
wherein:
$R_1$, $R_2$, $R_9$, $R_{10}$, $R_{11}$ $R_{12}$, $R_{13}$ and $R_{14}$ are independently selected from hydrogen, halogen, cyano, nitro, azido, —$OR_3$, —$NR_4C(O)OR_6$, —$OC(O)R_3$, —$NR_4S(O)_jR_6$, —$S(O)_jNR_3R_4$, —$S(O)_jNR_4C(O)R_3$, —$C(O)NR_4S(O)_jR_6$, $S(O)_jR_6$, —$NR_4C(O)R_3$, —$C(O)NR_3R_4$, —$NR_5C(O)NR_3R_4$, —$NR_5C(NCN)NR_3R_4$, —$NR_3R_4$ and $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —$S(O)_j(C_1$-$C_6$ alkyl), —$S(O)_j(CR_4R_5)_m$-aryl, aryl, arylalkyl, heteroaryl, heteroarylalkyl, heterocyclyl, heterocyclylalkyl, —$O(CR_4R_5)_m$-aryl, —$NR_4(CR_4R_5)_m$-aryl, —$O(CR_4R_5)_m$-heteroaryl, —$NR_4(CR_4R_5)_m$, heteroaryl, —$O(CR_4R_5)_m$-heterocyclyl, —$NR_4(CR_4R_5)_m$-heterocyclyl, and —$S(C_1$-$C_2$ alkyl) substituted with 1 to 5 F, where each alkyl, alkenyl, alkynyl, cycloalkyl, aryl, heteroaryl and heterocyclyl are substituted or unsubstituted;

$R_3$ is selected from hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, arylalkyl, heteroaryl, heteroarylalkyl, heterocyclyl, and heterocyclylalkyl, where each alkyl, alkenyl, alkynyl, cycloalkyl, heteroaryl and heterocyclyl is substituted or unsubstituted; or aryl which is unsubstituted or substituted with 1 to 5 groups independently selected from oxo, halogen, nitro, $CF_3$, $CHF_2$, $CH_2F$, $OCF_3$, $OCHF_2$, $OCH_2F$, azido, $NR'SO_2R''''$, $SO_2NR''$, $C(O)R'$, $C(O)OR'$, $OC(O)R'$, $NR'C(O)OR''''$, $NR'C(O)R''$, $C(O)NR'R''$, $SR''''$, $S(O)R''''$, $SO_2R'$, $NR'R''$, $NR'C(O)NR''R'''$, $NR'C(NCN)NR''R'''$, $OR'$, aryl, heteroaryl, arylalkyl, heteroarylalkyl, heterocyclyl, and heterocyclylalkyl;

$R_4$ is selected from hydrogen or $C_1$-$C_6$ alkyl whereby alkyl may be substituted or unsubstituted; or $R_3$ and $R_4$ can be taken together with the atom to which they are attached to form a 4 to 10 membered heteroaryl or heterocyclic ring, each of which is substituted or unsubstituted;

$R_5$ is selected from hydrogen or $C_1$-$C_6$ alkyl whereby alkyl may be substituted or unsubstituted; or $R_4$ and $R_5$ can be taken together with the atom to which they are attached to form a 4 to 10 membered carbocyclic, heteroaryl or heterocyclic ring, each of which is substituted or unsubstituted;

$R_6$ is selected from trifluoromethyl; and $C_1$-$C_{10}$ alkyl, $C_3$-$C_{10}$ cycloalkyl, aryl, arylalkyl, heteroaryl, heteroarylalkyl, heterocyclyl, and heterocyclylalkyl, where each alkyl, cycloalkyl, aryl, heteroaryl and heterocyclyl substituted or unsubstituted;

R', R" and R'" are independently selected from hydrogen, $C_1$-$C_4$ alkyl, $C_2$-$C_4$ alkenyl, aryl and arylalkyl;

R"" is selected from $C_1$-$C_4$ alkyl, $C_1$-$C_4$ alkenyl, aryl and arylalkyl;

W is selected from heteroaryl containing 1-4 heteroatoms or heterocyclyl containing 1-4 heteroatoms each of which is unsubstituted or substituted by 1 to 5 substituents $ZR_{15}$; or W is —$C(O)OR_{15}$, —$C(O)NR_4R_{15}$, —$C(O)NR_4OR_{15}$, —$C(O)(C_3$-$C_{10}$ cycloalkyl), —$C(O)(heterocyclyl)$, $S(O)_j NR_4R_{15}$, $S(O)_jNR_4OR_{15}$, —$S(O)_jR_4C(O)R_{15}$, —$C(O) NR_4S(O)_jR_6$, —$C(O)NR_4NR_4R_{15}$, —$C(O)C(O)R_{15}$, —$C(O)CR'R''C(O)R_{15}$, —$NR'R''$, —$NR'C(O)R'$, —$NR'S(O)_jR'$, —$NRC(O)NR'R''$, $NR'S(O)_jNR'R''$, or —$C(O) NR_4NR_4C(O)R_{15}$;

and when W is $C(O)OH$, then $R_1$, $R_2$, $R_{12}$, $R_{13}$ and $R_{14}$ are independently selected from hydrogen, halogen, cyano, nitro, azido, —$NR_4C(O)OR_6$, —$OC(O)R_3$, —S—$C_1$-$C_2$ alkyl substituted with 1 to 5 F, —$NR_4S(O)_jR_6$, —$S(O)_j NR_3R_4$, —$S(O)_jNR_4C(O)R_3$, —$C(O)NR_4S(O)_jR_6$, $S(O)_j R_6$, —$NR_4C(O)R_3$, —$NR_5C(O)NR_3R_4$, —$NR_5C(NCN) NR_3R_4$ and $C_{1-10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —$S(O)_j(C_1$-$C_6$ alkyl), —$S(O)_j(CR_4R_5)_m$-aryl, aryl, arylalkyl, heteroaryl, heteroarylalkyl, heterocyclyl, heterocyclylalkyl, —$O(CR_4R_5)_m$-aryl, —$NR_4(CR_4R_5)_m$-aryl, —$O(CR_4 R_5)_m$-heteroaryl, —$NR_4(CR_4R_5)_m$-heteroaryl, —$O(CR_4R_5)_m$-heterocyclyl and —$NR_4(CR_4R_5)_m$-heterocyclyl, where each alkyl, alkenyl, alkynyl, cycloalkyl, aryl, heteroaryl and heterocyclyl are substituted or unsubstituted; —$NR_{33}R_{44}$, $C(O)NR_3R_{44}$, or $OR_{33}$, whereby $R_{33}$ is selected from hydrogen, $CF_3$, $CHF_2$, $CH_2F$, $C_2$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, arylalkyl, heteroaryl, heteroarylalkyl, heterocyclyl, and heterocyclylalkyl, where each alkyl, alkenyl, alkynyl, cycloalkyl, heteroaryl and heterocyclyl is substituted or unsubstituted, and $R_{44}$ is selected from hydrogen, $CF_3$, $CHF_2$, $CH_2F$ and $C_2$-$C_6$ alkyl;

Z is a bond, $NR_{16}$, O, $NR_{16}SO_2$ or S.

$R_{15}$ is independently selected from hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, and heterocyclylalkyl, where each alkyl, alkenyl, alkynyl, cycloalkyl, aryl, heteroaryl and heterocyclyl is substituted or unsubstituted;

$R_{16}$ is selected from hydrogen or $C_1$-$C_{10}$ alkyl, or $R_{15}$ and $R_{16}$ form together a 4 to 10 membered cyclic ring with 1 or 2 N atoms and optionally an O atom, said ring being substituted or unsubstituted;

X is N or N→O;

m is 0, 1, 2, 3, 4 or 5; and j is 1 or 2

In one embodiment the compounds as defined by Formula (II) do not include the following compounds:

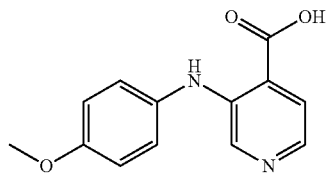 [SMILES: COc1ccc(Nc2cnccc2C(=O)O)cc1]

3-(4-Methoxy-phenylamino)-isonicotinic acid, that has been described as an intermediate in the synthesis of benzonaphthyridine derivatives as anti-malarial agents,

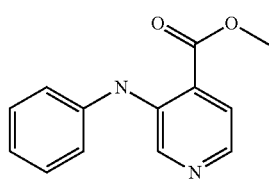 [SMILES: COC(=O)c1ccncc1Nc1ccccc1]

3-Phenylamino-isonicotinic acid methyl ester, that has been described as an anti-allergic agent (Sherlock et al., J. Med. Chem. 1988, 31, 2108-21);

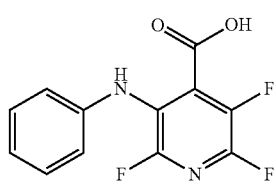 [SMILES: O=C(O)c1c(F)c(F)nc(F)c1Nc1ccccc1]

2,3,6-Trifluoro-5-phenylamino-isonicotinic acid, whose synthesis has been described (Orlova et al., lzvestiya Sibirskogo Otdeleniya Akademii Nauk SSSR, Seriya Khimicheskikh Nauk 1994, 6, 93-7; and

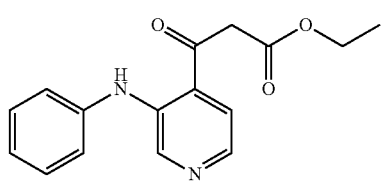 [SMILES: CCOC(=O)CC(=O)c1ccncc1Nc1ccccc1]

3-Oxo-3-(3-phenylamino-pyridin-4-yl)-propionic acid ethyl ester, that has been described as in intermediate in the synthesis of phenyl dihydro-naphthydrine derivatives for the treatment of diabetes and diabetes-related disorders.

In preferred embodiments, the variants have the following meanings:

$R_1$ is as defined above, preferably hydrogen, halo, $C_1$-$C_4$ alkyl, $C_3$-$C_4$ cycloalkyl, $C_2$-$C_4$ alkenyl, $C_2$-$C_4$ alkynyl, cyano, nitro, $OR_3$ or $NR_3R_4$; more preferably hydrogen, halo or $C_1$-$C_4$ alkyl, still more preferably hydrogen or halo, most preferably hydrogen or F. In one embodiment, $R_1$ is hydrogen.

$R_2$ is as defined above, preferably hydrogen, halo, $C_1$-$C_4$ alkyl, $C_3$-$C_4$ cycloalkyl, $C_2$-$C_4$ alkenyl, $C_2$-$C_4$ alkynyl, cyano, nitro, $OR_3$ or $NR_3R_4$; more preferably hydrogen, halo or $C_1$-$C_2$ alkyl, still more preferably halo or methyl, most preferably Cl, F or methyl. In one embodiment, $R_2$ is methyl. In another embodiment, methyl is preferably further substituted by 1, 2 or 3 fluorines, preferably 3 fluorines. Most preferably, $R_2$ is F.

$R_9$ is as defined above, preferably hydrogen, halo, $C_1$-$C_4$ alkyl, $C_3$-$C_4$ cycloalkyl, $C_2$-$C_4$ alkenyl, $C_2$-$C_4$ alkynyl, cyano, nitro, $OR_3$ or $NR_3R_4$; more preferably hydrogen, halo or $C_1$-$C_4$ alkyl, still more preferably hydrogen, methyl or halo, most preferably hydrogen, methyl, Cl or F. In one embodiment, $R_9$ is hydrogen.

$R_{10}$ is as defined above, preferably hydrogen, halo, $C_1$-$C_{10}$ alkyl, $C_3$-$C_{10}$ cycloalkyl, $C_2$-$C_{10}$ alkenyl, $C_2$-$C_{10}$ alkynyl, cyano, nitro, azido; $NR_4SO_2R_6$; $SO_2NR_3R_4$; $SO_2R_6$; $C(O)NR_3R_4$; $C(O)OR_3$; —$S(O)_jNR_4C(O)R_3$, —$C(O)NR_4S(O)_jR_6$, $OR_3$ or $NR_3R_4$, more preferably hydrogen, halo, nitro, $C_1$-$C_4$ alkyl, O—$C_1$-$C_4$ alkyl, $SO_2NR_3R_4$ or $C(O)NR_3R_4$, still more preferably hydrogen F, Cl, Br, nitro, methyl, O-methyl, $SO_2NR_3R_4$ or $C(O)NR_3R_4$, most preferably hydrogen, F, Cl, Br, methyl or O-methyl.

In one embodiment $R_{10}$ is hydrogen. In another embodiment, $R_{10}$ is methyl. In yet another embodiment, methyl is preferably further substituted by 1, 2 or 3 fluorines, preferably 3 fluorines. In preferred embodiments of $R_{10}$, $R_3$ and $R_4$ are independently $C_1$-$C_6$ alkyl, more preferably $C_1$-$C_4$ alkyl, optionally substituted by 1 or 2 alkyl amino, dialkyl amino, amino, O-alkyl, hydroxy, or $R_3$ and $R_4$ form together a cyclic ring with 1 or 2 N atoms and optionally an O atom, said ring being optionally substituted by 1 or 2 alkyl amino, amino, hydroxy or O-alkyl.

$R_{11}$ is as defined above, preferably hydrogen, halo, $C_1$-$C_4$ alkyl, $C_3$-$C_4$ cycloalkyl, $C_2$-$C_4$ alkenyl, $C_2$-$C_4$ alkynyl, cyano, nitro, $OR_3$ or $NR_3R_4$; more preferably hydrogen, halo or $C_1$-$C_4$ alkyl or O—$C_1$-$C_4$ alkyl, still more preferably hydrogen, methyl, O-methyl or halo, most preferably hydrogen, methyl, Cl, Br or F. In one embodiment, $R_{11}$ is hydrogen. In another embodiment, $R_{11}$ is methyl. In yet another embodiment, methyl is preferably further substituted by 1, 2 or 3 fluorines, preferably 3 fluorines.

$R_{12}$ is as defined above, preferably hydrogen, halo, $C_1$-$C_{10}$ alkyl, $C_3$-$C_{10}$ cycloalkyl, $C_2$-$C_{10}$ alkenyl, $C_2$-$C_{10}$ alkynyl, cyano, nitro, azido; $NR_4SO_2R_6$; $SO_2NR_3R_4$; $SO_2R_6$; $C(O)NR_3R_4$; $C(O)OR_3$; $OR_3$, $NR_3R_4$ or —$S(C_1$-$C_2$ alkyl) substituted with 1 to 5 F, more preferably hydrogen, halo, nitro, $C_1$-$C_4$ alkyl, O—$C_1$-$C_4$ alkyl, $SCF_3$, $SCHF_2$, $SCH_2F$, $SO_2NR_3R_4$ or $C(O)NR_3R_4$, still more preferably hydrogen, F, Cl, Br, nitro, methyl, O-methyl, $SCF_3$, $SCHF_2$, $SCH_2F$, $SO_2NR_3R_4$ or $C(O)NR_3R_4$, most preferably hydrogen I, Cl, Br, $SCF_3$, $SCHF_2$, $SCH_2F$, methyl or O-methyl. In one embodiment $R_{12}$ is hydrogen. In another embodiment, $R_{12}$ is methyl, $SCF_3$, $SCHF_2$, $SCH_2F$ or O-methyl, wherein methyl or O-methyl is preferably unsubstituted or further substituted by 1, 2 or 3 fluorines, preferably 2 or 3 fluorines. In preferred embodiments of $R_{12}$, $R_3$ and $R_4$ are independently $C_1$-$C_6$ alkyl, more preferably $C_1$-$C_4$ alkyl, optionally substituted by 1 or 2 alkyl amino, dialkyl amino, amino, O-alkyl, hydroxy, or $R_3$ and $R_4$ form together a cyclic ring with 1 or 2 N atoms and optionally an O atom, said ring being optionally substituted by 1 or 2 alkyl amino, amino, hydroxy or O-alkyl. Most preferably, $R_{12}$ is Br or I.

$R_{13}$ is as defined above, preferably hydrogen, halo, $C_1$-$C_4$ alkyl, $C_3$-$C_4$ cycloalkyl, $C_2$-$C_4$ alkenyl or $C_2$-$C_4$ alkynyl, more preferably hydrogen, F, Cl or methyl, most preferably hydrogen or F. in one embodiment, $R_{13}$ is hydrogen.

$R_{14}$ is as defined above, preferably hydrogen, halo, $C_1$-$C_4$ alkyl, $C_3$-$C_4$ cycloalkyl, $C_2$-$C_4$ alkenyl or $C_2$-$C_4$ alkynyl, more preferably hydrogen, F, Cl or methyl, most preferably hydrogen or F. In one embodiment, $R_{14}$ is hydrogen.

As set forth above, the variants of each of $R_1$, $R_2$ and $R_9$ to $R_{14}$ may be substituted. In this case they can be substituted with 1 to 5, preferably 1 to 3, more preferably 1 or 2 groups independently selected from oxo, halogen, cyano, nitro, $CF_3$, $CHF_2$, $CH_2F$, $OCF_3$, $OCHF_2$, $OCH_2F$, $SCF_3$, $SCHF_2$, $SCH_2F$, azido, $NR_4SO_2R_6$, $SO_2NR_3R_4$, $C(O)R_3$, $C(O)OR_3$, $OC(O)R_3$, $NR_4C(O)OR_6$, $NR_4C(O)R_3$, $C(O)NR_3R_4$, $NR_3R_4$, $NR_5C(O)NR_3R_4$, $NR_5C(NCN)NR_3R_4$, $OR_3$, aryl, heteroaryl, arylalkyl, heteroarylalkyl, heterocyclyl, and heterocyclylalkyl, preferably oxo, halogen, cyano, nitro, $CF_3$, $CHF_2$, $CH_2F$, $OCF_3$, $OCHF_2$, $OCH_2F$, $SCF_3$, $SCHF_2$, $SCH_2F$, azido, $NR_4SO_2R_6$, $SO_2NR_3R_4$, $C(O)R_3$, $C(O)OR_3$, $OC(O)R_3$, $OR_3$, more preferably oxo, halogen, cyano, nitro, trifluoromethyl, difluoromethoxy, trifluoromethoxy or azido, most preferably halogen, cyano, nitro, $CF_3$, $CHF_2$, $CH_2F$, $OCF_3$, $OCHF_2$, $OCH_2F$, $SCF_3$, $SCHF_2$, $SCH_2F$, OH, O-methyl, $NH_2$ or N(methyl)$_2$.

$R_3$ is as defined above, preferably hydrogen, trifluoromethyl, $C_1$-$C_4$ alkyl, $C_2$-$C_4$ alkenyl, $C_2$-$C_4$ alkynyl, $C_3$-$C_6$ cycloalkyl, $C_3$-$C_6$ cycloalkylalkyl, more preferably hydrogen or $C_1$-$C_4$ alkyl most preferably hydrogen, methyl or ethyl.

$R_4$ is as defined above, preferably hydrogen or $C_1$-$C_4$ alkyl, more preferably hydrogen, methyl or ethyl.

In one preferred embodiment, $R_3$ and $R_4$ can be taken together with the atom to which they are attached to form a 4 to 7, preferably 5 or 6, membered heteroaryl or heterocyclic ring.

$R_5$ is as defined above, preferably hydrogen or $C_1$-$C_4$ alkyl, more preferably hydrogen, methyl or ethyl.

In one embodiment, $R_4$ and $R_5$ can be taken together with the atom to which they are attached to form a 4 to 7, preferably 5 or 6, membered carbocyclic, heteroaryl or heterocyclic ring.

$R_6$ is as defined above, preferably trifluoromethyl, $C_1$-$C_4$ alkyl, $C_2$-$C_4$ alkenyl, $C_2$-$C_4$ alkynyl, $C_3$-$C_6$ cycloalkyl, $C_3$-$C_6$ cycloalkylalkyl, more preferably $C_1$-$C_4$ alkyl, most preferably methyl or ethyl.

As set forth above, the variants of each of $R_3$, $R_4$, $R_5$, $R_6$ or the rings formed by $R_3$ and $R_4$ and $R_4$ and $R_5$ may be substituted. In this case they can be substituted with 1 to 5, preferably 1 to 3, more preferably 1 or 2 groups independently selected from oxo, halogen, cyano, nitro, $CF_3$, $CHF_2$, $CH_2F$, $OCF_3$, $OCHF_2$, $OCH_2F$, azido, NR'SO$_2$R"", SO$_2$NR", C(O)R', C(O)OR', OC(O)R', NR'C(O)OR"", NR'C(O)R", C(O)NR'R", SR"", S(O)R"", SO$_2$R', NR'R", NR'C(O)NR"R'", NR'C(NCN)NR"R'", OR', aryl, heteroaryl, arylalkyl, heteroarylalkyl, heterocyclyl, and heterocyclylalkyl, preferably oxo, halogen, cyano, nitro, $CF_3$, $CHF_2$, $CH_2F$, $OCF_3$, $OCHF_2$, $OCH_2F$, azido, NR'SO$_2$R"", SO$_2$NR", C(O)R', C(O)OR', OC(O)R', NR'C(O)OR"", NR'C(O)R", C(O)NR'R", SR"", S(O)R"", SO$_2$R', NR'R", NR'C(O)NR"R'", NR'C(NCN)NR"R'" or OR', more preferably oxo, halogen, cyano, nitro, $CF_3$, $CHF_2$, $CH_2F$, $OCF_3$, $OCHF_2$, $OCH_2F$, azido, SR"", S(O)R"", SO$_2$R', NR'R" or OR', most preferably In one embodiment, $R_3$ is preferably oxo, halogen, nitro, trifluoromethyl, OH, O-methyl, $NH_2$ or $N(methyl)_2$.

R' is selected from hydrogen, $C_1$-$C_4$ alkyl, $C_2$-$C_4$ alkenyl, aryl and arylalkyl, preferably hydrogen or $C_1$-$C_4$ alkyl, more preferably hydrogen or methyl.

R'' is selected from hydrogen, $C_1$-$C_4$ alkyl, $C_2$-$C_4$ alkenyl, aryl and arylalkyl, preferably hydrogen or $C_1$-$C_4$ alkyl, more preferably hydrogen or methyl.

R''' is selected from hydrogen, $C_1$-$C_4$ alkyl, $C_2$-$C_4$ alkenyl, aryl and arylalkyl, preferably hydrogen or $C_1$-$C_4$ alkyl, more preferably hydrogen or methyl.

R'''' is selected from $C_1$-$C_4$ alkyl, $C_1$-$C_4$ alkenyl, aryl and arylalkyl, preferably $C_1$-$C_4$ alkyl, more preferably methyl.

Alternatively, any two of R', R'', R''' or R'''' can be taken together with the atom to which they are attached to form a 4 to 10 membered carbocyclic, heteroaryl or heterocyclic ring, each of which is optionally substituted with one to three groups independently selected from halogen, cyano; nitro, $CF_3$, $CHF_2$, $CH_2F$, $OCF_3$, $OCHF_2$, $OCH_2F$, azido, aryl, heteroaryl, arylalkyl, heteroarylalkyl, heterocyclyl, and heterocyclylalkyl, preferably halogen, cyano; nitro, trifluoromethyl, difluoromethoxy, trifluoromethoxy and azido.

W is as defined above, preferably heteroaryl containing 1, 2 or 3 heteroatoms, or heterocyclyl containing 1, 2, or 3 heteroatoms, more preferably heteroaryl, each of which is unsubstituted or substituted by 1 to 5, preferably 1 to 3, more preferably 1, substituents $ZR_{15}$, or W is —C(O)O$R_{15}$, —C(O)N$R_4R_{15}$, —C(O)N$R_4$O$R_{15}$, —O(O)(C$_3$-C$_{10}$ cycloalkyl), —C(O)(C$_2$-C$_{10}$ alkyl), —S(O)$_j$N$R_4$C(O)$R_{15}$, —C(O)N$R_4$S(O)$_j$R$_6$, S(O)$_j$N$R_4R_{15}$ or S(O)$_j$N$R_4$O$R_{15}$, more preferably W is heteroaryl containing 1, 2, or 3, specifically 2 or 3 N atoms, C(O)N$R_4$O$R_{15}$ or S(O)$_2$N$R_4$O$R_{15}$.

When W is heteroaryl, it is preferably

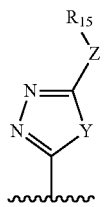

where Z and $R_{15}$ are as defined above, preferably Z is a bond, $NR_{16}$, $NR_{16}SO_2$ or O, more preferably $NR_{16}$, wherein $R_{16}$ is as defined above, preferably hydrogen or $C_1$-$C_4$ alkyl, more preferably hydrogen. $R_{15}$ is preferably selected from hydrogen, $C_1$-$C_4$ alkyl, $C_1$-$C_4$ alkenyl, $C_4$-$C_8$ cycloalkylalkyl, each may contain 1 N atom optionally an O atom, where alkyl, alkenyl or cycloalkylalkyl may be further substituted by 1 or 2 of OH, O—$C_1$-$C_4$ alkyl or NR'R'', where R' and R'' are independently hydrogen or $C_1$-$C_4$ alkyl where R' and R'' form a 3 to 7 membered ring with 1 or 2 N atoms and optionally an O atom. Alternatively, $R_{16}$ and $R_{15}$ may form together a 4 to 10 membered cyclic ring with 1 or 2 N atoms and optionally an O atom, said ring being optionally substituted by 1 or 2 alkyl amino, amino, hydroxy or O-alkyl. More preferably $R_{15}$ is $C_1$-$C_4$ alkyl or $C_1$-$C_4$ alkenyl optionally substituted with 1 substitutent OH, O-Me, $NH_2$, $N(methyl)_2$ or $N(ethyl)_2$.

Y is O or NR', preferably O.

Alternatively, W is preferably —C(O)O$R_{15}$, —C(O)NR$_4$R$_{15}$, —C(O)NR$_4$OR$_{15}$, S(O)$_j$NR$_4$R$_{15}$ or S(O)$_j$NR$_4$OR$_{15}$, more preferably —C(O)NR$_4$OR$_{15}$ or S(O)$_2$NR$_4$OR$_{15}$. In these cases $R_{15}$ is preferably as defined below.

According to Formula (II), when W is C(O)OH, then $R_1$, $R_2$, $R_{12}$, $R_{13}$ and $R_{14}$ are independently selected from hydrogen, halogen, cyano, nitro, azido, —NR$_4$C(O)OR$_6$, —OC(O)R$_3$, —NR$_4$S(O)$_j$R$_6$, —S(O)$_j$NR$_3$R$_4$, —S(O)$_j$NR$_4$C(O)R$_3$, —C(O)NR$_4$S(O)$_j$R$_6$, S(O)$_j$R$_6$, —NR$_4$C(O)R$_3$, —NR$_5$C(O)NR$_3$R$_4$, —NR$_5$C(NCN)NR$_3$R$_4$ and $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, —S(O)$_j$(C$_1$-$C_6$ alkyl), —S(O)$_j$(CR$_4$R$_5$)$_m$-aryl, aryl, arylalkyl, heteroaryl, heteroarylalkyl, heterocyclyl, heterocyclylalkyl, —O(CR$_4$R$_5$)$_m$-aryl, —NR$_4$(CR$_4$R$_5$)$_m$-aryl, —O(CR$_4$R$_5$)$_m$-heteroaryl, —NR$_4$(CR$_4$R$_5$)$_m$-heteroaryl, —O(CR$_4$R$_5$)$_m$-heterocyclyl, —NR$_4$(CR$_4$R$_5$)$_m$-heterocyclyl and —S(C$_1$-$C_2$ alkyl) substituted with 1 to 5 F, where each alkyl, alkenyl, alkynyl, cycloalkyl, aryl, heteroaryl and heterocyclyl are unsubstituted or substituted as set forth above; —NR$_{33}$R$_{44}$, C(O)NR$_3$R$_{44}$, or OR$_{33}$, whereby R$_{33}$ is selected from hydrogen, CF$_3$, CHF$_2$, CH$_2$F, $C_2$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, arylalkyl, heteroaryl, heteroarylalkyl, heterocyclyl, and heterocyclylalkyl, where each alkyl, alkenyl, alkynyl, cycloalkyl, heteroaryl and heterocyclyl is unsubstituted or substituted, and R$_{44}$ is selected from hydrogen, CF$_3$, CHF$_2$, CH$_2$F and $C_2$-$C_6$ alkyl. In this case, preferred embodiments of $R_1$, $R_2$, $R_{12}$, $R_{13}$ and $R_{14}$ are as described above, and R$_{33}$ is preferably selected from hydrogen, CF$_3$, CHF$_2$, CH$_2$F, $C_2$-$C_4$ alkyl and $C_2$-$C_{10}$ alkenyl, and R$_{44}$ is selected from hydrogen, CF$_3$, CHF$_2$, CH$_2$F and $C_2$-$C_4$ alkyl.

Z is as defined above, preferably a bond, NR$_{16}$, NR$_{16}$SO$_2$ or O, more preferably NR$_{16}$.

R$_{15}$ is as defined above, preferably hydrogen, $C_1$-$C_4$ alkyl, $C_1$-$C_4$ alkenyl, $C_4$-$C_6$ cycloalkylalkyl, more preferably $C_1$-$C_4$ alkyl or $C_1$-$C_4$ alkenyl, yet more preferably $C_1$-$C_4$ alkyl. Alkyl or alkenyl may be further substituted with 1 to 5, preferably 1, 2 or 3, more preferably 1 or 2, substituents selected from OR$_3$ or NR'R'' wherein R$_3$ is selected from hydrogen, $C_1$-$C_4$ alkyl or $C_1$-$C_4$ alkenyl, $C_4$-$C_6$ cycloalkylalkyl, more preferably hydrogen, methyl or ethyl, and where R' and R'' are independently hydrogen or $C_1$-$C_4$ alkyl, more preferably hydrogen, methyl or ethyl, still more preferably both R' and R'' are methyl. Yet more preferably, R$_{15}$ may be substituted by 1 or 2 of OH, O—$C_1$-$C_4$ alkyl or NR'R''.

Most preferably, R$_{15}$ is $C_1$-$C_4$ alkyl or $C_1$-$C_4$ alkenyl optionally substituted with 1 substitutent OH, O-Me, NH$_2$, N(methyl)$_2$ or N(ethyl)$_2$.

R$_{16}$ is as defined above, preferably hydrogen or $C_1$-$C_4$ alkyl, more preferably hydrogen.

Alternatively, R$_{16}$ and R$_{15}$ may form together a 4 to 10, preferably 5 to 6, membered cyclic ring with 1 or 2 N atoms and optionally an O atom, said ring being optionally substituted by 1 or 2 alkyl amino, amino, hydroxy or O-alkyl.

X is as defined above. In one embodiment X is N, in another embodiment X is N→O.

m is as defined above, preferably 0, 1, 2 or 3, more preferably 0, 1 or 2, most preferably 1.

j is as defined above, preferably 2.

In the above, any of the preferred definitions for each variant can be combined with the preferred definition of the other variants.

The combinations as set forth in the claims are particularly preferred.

In the above and the following, the employed terms have independently the meaning as described below:

Aryl is an aromatic mono- or polycyclic moiety with preferably 6 to 20 carbon atoms which is preferably selected from phenyl, biphenyl, naphthyl, tetrahydronaphthyl, fluorenyl, indenyl or phenanthrenyl, more preferably phenyl or naphthyl.

Heteroaryl is an aromatic moiety having 6 to 20 carbon atoms with at least one ring containing a heteroatom selected from O, N and/or S, or heteroaryl is an aromatic ring containing at least one heteroatom selected from O, N and/or S and 1 to 6 carbon atoms. Preferably, heteroaryl contains 1 to 4, more preferably 1, 2 or 3 heteroatoms selected from O and/or N and is preferably selected from pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition. Preferred heteroaryl include pyridinyl, imidazolyl, pyrimidinyl, pyrazolyl, triazolyl, pyrazinyl, tetrazolyl, isoxazolyl, oxazolyl, isothiazolyl, oxadiazolyl, triazolyl. Heteroaryl groups are optionally mono-, di-, or trisubstituted with, e.g., halogen, lower alkyl, lower alkoxy, haloalkyl, aryl, heteroaryl, and hydroxy.

Heterocyclyl is a saturated or unsaturated ring containing at least one heteroatom selected from O, N and/or S and 1 to 6 carbon atoms. Preferably, heterocyclyl contains 1 to 4, more preferably 1, 2 or 3 heteroatoms selected from O and/or N and is preferably selected from pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, azetidin-2-one-1-yl, pyrrolidin-2-one-1-yl, piperid-2-one-1-yl, azepan-2-one-1-yl, 3-azabicyclo[3.1.0]hexanyl, 3-azabicyclo[4.1.0]heptanyl, azabicyclo[2.2.2]hexanyl, 3H-indolyl and quinolizinyl. Spiromoieties are also included within the scope of this definition.

Carbocyclyl is a monocyclic or polycyclic ring system of 3 to 20 carbon atoms which may be saturated, unsaturated or aromatic.

Alkyl is a saturated hydrocarbon moiety, namely straight chain or branched alkyl having 1 to 10, preferably 1 to 8 carbon atoms, more preferably 1 to 4 carbon atoms, such as methyl, ethyl, n-propyl, isopropyl, n-butyl, isobutyl, tert-butyl, n-pentyl, isopentyl, neopentyl, hexyl or heptyl.

Cycloalkyl is an alkyl ring having 3 to 10, preferably 3 to 8 carbon atoms, more preferably 3 to 6 carbon atoms, such as cyclopropyl, cyclobutyl, cyclopentyl, cyclohexyl, cycloheptyl or cyclooctyl.

Alkenyl is an unsaturated hydrocarbon moiety with one or more double bonds, preferably one double bond, namely straight chain or branched alkenyl having 1 to 10, preferably 2 to 8 carbon atoms, more preferably 2 to 4 atoms, such as vinyl, allyl, methallyl, buten-2-yl, buten-3-yl, penten-2-yl, penten-3-yl, penten-4-yl, 3-methyl-but-3-enyl, 2-methyl-but-3-enyl, 1-methyl-but-3-enyl, hexenyl or heptenyl.

Alkynyl is an unsaturated hydrocarbon moiety with one or more triple bonds, preferably one triple bond, namely straight chain or branched alkynyl having 1 to 10, preferably 2 to 8 carbon atoms, more preferably 2 to 4 atoms, such as ethynyl, propynyl, butyn-2-yl, butyn-3-yl, pentyn-2-yl, pentyn-3-yl, pentyn-4-yl, 2-methyl-but-3-ynyl, 1-methyl-but-3-ynyl, hexynyl or heptynyl.

Halo or halogen is a halogen atom preferably selected from F, Cl, Br and I, preferably F, Cl, and Br.

In the definitions cycloalkylalkyl, arylalkyl, heretoarylalkyl and heterocyclylalkyl it is contemplated that cycloalkyl, aryl, heretoaryl and heterocyclyl are bonded via an alkylene moiety. This alkylene moiety may be a straight chain or branched chain group. Said alkylene moiety preferably has 1 to 6 carbon atoms. Examples thereof include methylene, ethylene, n-propylene, n-butylene, n-pentylene, n-hexylene, iso-propylene, sec.-butylene, tert.-butylene, 1,1-dimethyl propylene, 1,2-dimethyl propylene, 2,2-dimethyl propylene, 1,1-dimethyl butylene, 1,2-dimethyl butylene, 1,3-dimethyl butylene, 2,2-dimethyl butylene, 2,3-dimethyl butylene, 3,3-dimethyl butylene, 1-ethyl butylene, 2-ethyl butylene, 3-ethyl butylene, 1-n-propyl propylene, 2-n-propyl propylene, 1-iso-propyl propylene, 2-iso-propyl propylene, 1-methyl pentylene, 2-methyl pentylene, 3-methyl pentylene and 4-methyl pentylene. More preferably, said alkylene moiety has 1 to 3 carbon atoms, such as methylene, ethylene, n-propylene and iso-propylene. Most preferred is methylene.

"Carboxy refers to the group —C(O)OR, where R includes hydrogen or "$C_1$-$C_6$-alkyl".

"Acyl" refers to the group —C(O)R where R includes "$C_1$-$C_6$-alkyl", "aryl", "heteroaryl", "$C_3$-$C_8$-cycloalkyl", "$C_3$-$C_8$-heterocycloalkyl", "$C_1$-$C_6$-alkyl aryl" or "$C_1$-$C_6$-alkyl heteroaryl".

"Acyloxy" refers to the group —OC(O)R where R includes "$C_1$-$C_6$-alkyl", "aryl", "hetero-aryl", "$C_1$-$C_6$-alkyl aryl" or "$C_1$-$C_6$-alkyl heteroaryl".

"Aryl acyl" refers to aryl groups having an acyl substituent, including 2-acetylphenyl and the like.

"Heteroaryl acyl" refers to heteroaryl groups having an acyl substituent, including 2-acetylpyridyl and the like.

"Alkoxy" refers to the group —O—R where R includes "$C_1$-$C_6$-alkyl", "$C_2$-$C_6$-alkenyl", "$C_2$-$C_6$-alkynyl", "$C_3$-$C_8$-cycloalkyl", "Heterocycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl". Preferred alkoxy groups include by way of example, methoxy, ethoxy, phenoxy and the like.

"Alkoxycarbonyl" refers to the group —C(O)OR where R includes "$C_1$-$C_6$-alkyl" or "aryl" or "heteroaryl" or "$C_1$-$C_6$-alkyl aryl" or "$C_1$-$C_6$-alkyl heteroaryl".

"Alkoxycarbonylamino" refers to the group —NR'C(O)OR where R includes "$C_1$-$C_6$-alkyl" or "aryl" or "heteroaryl" or "$C_1$-$C_6$-alkyl aryl" or "$C_1$-$C_6$-alkyl heteroaryl" a and R' includes hydrogen or "$C_1$-$C_6$-alkyl "Aminocarbonyl" refers to the group —C(O)NRR' where each R, R' includes independently hydrogen or $C_1$-$C_6$-alkyl or aryl or heteroaryl or "$C_1$-$C_6$-alkyl aryl" or "$C_1$-$C_6$-alkyl hetero-aryl".

"Acylamino" refers to the group —NR(CO)R' where each R, R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl".

"Sulfonyloxy" refers to a group —OSO$_2$—R wherein R is selected from H, "$C_1$-$C_6$-alkyl", "$C_1$-$C_6$-alkyl" substituted with halogens, e.g., an —OSO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Sulfonyl" refers to group "—SO$_2$—R" wherein R is selected from H, "aryl", "heteroaryl", "$C_1$-$C_6$-alkyl", "$C_1$-$C_6$-alkyl" substituted with halogens, e.g., an —SO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$alkyl cycloalkyl", "$C_1$-$C_6$-alkyl heterocycloalkyl".

"Sulfinyl" refers to a group "—S(O)—R" wherein R is selected from H, "$C_1$-$C_6$-alkyl", "$C_1$-$C_6$-alkyl" substituted with halogens, e.g., an —SO—CF$_3$ group, "$C_2$-$C_6$-alkenyl", "$C_2$-$C_6$-alkynyl", "$C_3$-$C_8$-cycloalkyl", "Heterocycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Sulfanyl" refers to groups —S—R where R includes H, "$C_1$-$C_6$-alkyl", "$C_1$-$C_6$-alkyl" optionally substituted with halogens, e.g a —S—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl". Preferred sulfanyl groups include methylsulfanyl, ethylsulfanyl, and the like.

"Sulfonylamino" refers to a group —NRSO$_2$—R' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Aminosulfonyl" refers to a group —SO$_2$—NRR' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Amino" refers to the group —NRR' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "Heterocycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R and R', together with the nitrogen atom to which they are attached, can optionally form a 3-8-membered hetero-cycloalkyl ring.

"Substituted or unsubstituted": Unless otherwise constrained by the definition of the individual substituent, the above set out groups, like "alkyl", "alkenyl", "alkynyl", "alkoxy", "aryl" and "heteroaryl" etc. groups can optionally be independently substituted with from 1 to 5 substituents selected from the group consisting of "$C_1$-$C_6$-alkyl", "$C_1$-$C_6$-alkyl aryl", "$C_1$-$C_6$-alkyl heteroaryl", "$C_2$-$C_6$-alkenyl", "$C_2$-$C_6$-alkynyl", primary, secondary or tertiary amino groups or quaternary ammonium moieties, "acyl", "acyloxy", "acylamino", "aminocarbonyl", "alkoxycarbonylamino", "alkoxycarbonyl", "aryl", "aryloxy", "heteroaryl", "heteroaryloxy", carboxyl, cyano, halogen, hydroxy, nitro, sulfanyl, sulphoxy, sulphonyl, sulfonamide, alkoxy, thioalkoxy, trihalomethyl and the like. Within the framework of this invention, said "substitution" is meant to also comprise situations where neighboring substituents undergo ring closure, in particular when vicinal functional substituents are involved, thus forming e.g. lactams, lactons, cyclic anhydrides, but also acetals, thioacetals, aminals formed by ring closure for instance in an effort to obtain a protective group.

Compounds according to formula (I) include in particular those of the group consisting of:

Preferred embodiments of the compounds according to present invention are shown in scheme 1.

Scheme 1

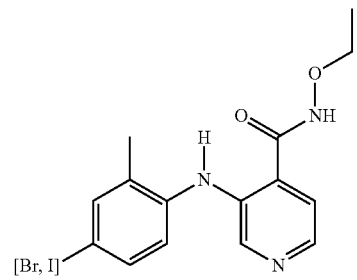

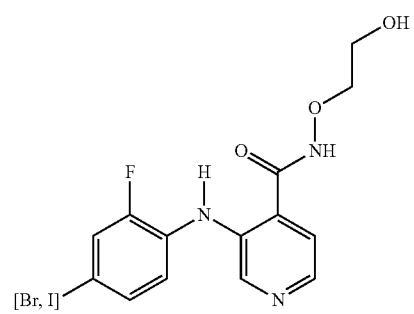

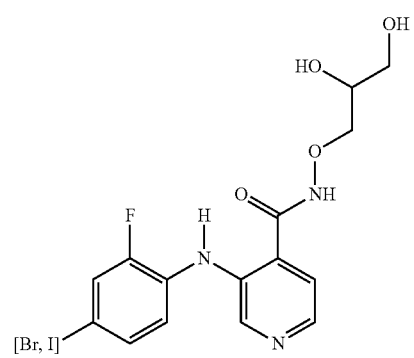

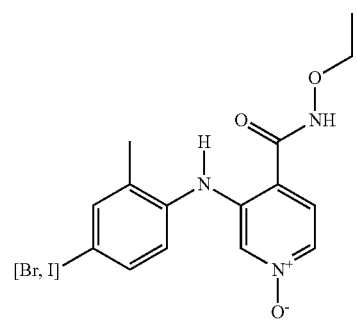

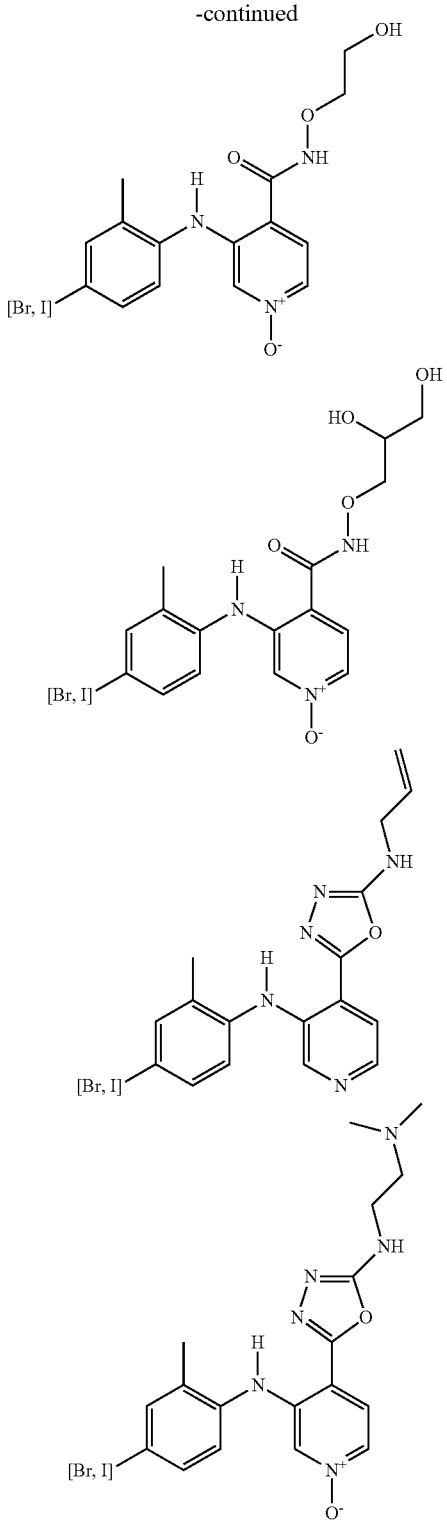

the present invention is acylated, alkylated or phosphorylated to form, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated. These compounds can be produced from compounds of the present invention according to well-known methods. Other examples of the prodrug are compounds, wherein the carboxylate in a compound of the present invention is for example converted into an alkyl-, aryl-, choline-, amino, acyloxymethylester, linolenoyl-ester.

Metabolites of compounds of the present invention are also within the scope of the present invention.

Where tautomerism, like e.g. keto-enol tautomerism, of compounds of the present invention or their prodrugs may occur, the individual forms, like e.g. the keto and enol form, are claimed separately and together as mixtures in any ratio. Same applies for stereoisomers, like e.g. enantiomers, cis/trans isomers, conformers and the like.

If desired, isomers can be separated by methods well known in the art, e.g. by liquid chromatography. Same applies for enantiomers by using e.g. chiral stationary phases. Additionally, enantiomers may be isolated by converting them into diastereomers, i.e. coupling with an enantiomerically pure auxiliary compound, subsequent separation of the resulting diastereomers and cleavage of the auxiliary residue. Alternatively, any enantiomer of a compound of the present invention may be obtained from stereoselective synthesis using optically pure starting materials.

The compounds of the present invention can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In case the compounds of the present invention contain one or more acidic or basic groups, the invention also comprises their corresponding pharmaceutically or toxicologically acceptable salts, in particular their pharmaceutically utilizable salts. Thus, the compounds of the of the present invention which contain acidic groups can be present on these groups and can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the present invention which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to the person skilled in the art like, for example by contacting these with an organic or inorganic The compounds of the present invention can be in the form of a prodrug compound. "Prodrug compound" means a derivative that is converted into a compound according to the present invention by a reaction with an enzyme, gastric acid or the like under a physiological condition in the living body, e.g. by oxidation, reduction, hydrolysis or the like, each of which is carried out enzymatically. Examples of the prodrug are compounds, wherein the amino group in a compound of acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

Furthermore, the present invention provides pharmaceutical compositions comprising a compound of the present invention, or a prodrug compound thereof, or a pharmaceutically acceptable salt or solvate thereof as active ingredient together with a pharmaceutically acceptable carrier.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

A pharmaceutical composition of the present invention may additionally comprise one or more other compounds as active ingredients like one or more additional compounds of the present invention, or a prodrug compound or other MEK inhibitors.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In one embodiment, said compounds and pharmaceutical composition are for the treatment of cancer such as brain, lung, squamous cell, bladder, gastic, pancreatic, breast, head, neck, renal, kidney, ovarian, prostate, colorectal, oesohageal, testicular, gynecological or thyroid cancer. In another embodiment, said pharmaceutical composition is for the treatment of a noncancerous hyperproliferative disorder such as benign hyperplasia of the skin (e.g., psoriasis), restenosis, or prostate (e.g. benign prostatic hypertrophy (BPH)).

The invention also relates to the use of compounds according to formula (I) or formula (II) for the preparation of a medicament for the treatment of hyperproliferative diseases related to the hyperactivity of MEK as well as diseases modulated by the MEK cascade in mammals, or disorders mediated by aberrant proliferation, such as cancer.

The invention also relates to a compound or pharmaceutical composition for the treatment of pancreatitis or kidney disease (including proliferative glomerulonephtitis and diabetes induced renal disease) or pain in a mammal which comprises a therapeutically effective amount of a compound of the present invention, or a pharmaceutically acceptable salt, prodrug or hydrate thereof, and a pharmaceutically acceptable carrier. The invention also relates to a compound or pharmaceutical composition for the prevention of blastocyte implantation in a mammal which comprises a therapeutically effective amount of a compound of the present invention, or a pharmaceutically acceptable salt, prodrug or hydrate thereof, and a pharmaceutically acceptable carrier. The invention also relates to a compound or pharmaceutical composition for treating a disease related to vasculogenesis or angiogenesis in a mammal which comprises a therapeutically effective amount of a compound of the present invention, or a pharmaceutically acceptable salt, prodrug or hydrate thereof, and a pharmaceutically acceptable carrier.

In one embodiment, said compound or pharmaceutical composition is for treating a disease selected from the group consisting of tumor angiogenesis, chronic inflammatory disease such as rheumatoid arthritis, inflammatory bowel disease, atherosclerosis, skin diseases such as psoriasis, excema, and sclerodema, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to of the use for treating a hyperproliferative disorder in a mammal that comprises administering to said mammal a therapeutically effective amount of a compound of the present invention, or a pharmaceutically acceptable salt, prodrug or hydrate thereof. In one embodiment, said use relates to the treatment of cancer such as brain, lung, squamous cell, bladder, gastic, pancreatic, breast, head, neck, renal, kidney, ovarian, prostate, colorectal, oesohageal, testicular, gynecological or thyroid cancer. In another embodiment, said use relates to the treatment of a non-cancerous hyperproliferative disorder such as benign hyperplasia of the skin (e.g., psoriasis), restenosis, or prostate (e.g., benign prostatic hypertrophy (BPH)).

The invention also relates to a use for the treatment of a hyperproliferative disorder in a mammal that comprises administering to said mammal a therapeutically effective amount of a compound of the present invention, or a pharmaceutically acceptable salt, prodrug or hydrate thereof, in combination with an anti-tumor agent selected from the group consisting of mitotic inhibitors, alkylating agents, antimetabolites, intercalating antibiotics, growth factor inhibitors, cell cycle inhibitors, enzyme inhibitors, topoisomerase inhibitors, biological response modifiers, antihormones, angiogenesis inhibitors, and anti-androgens.

The invention also relates to a use of treating pancreatitis or kidney disease or pain in a mammal that comprises administering to said mammal a therapeutically effective amount of a compound of the present invention, or a pharmaceutically acceptable salt, prodrug or hydrate thereof. The invention also relates to a use of preventing blastocyte implantation in a mammal that comprises administering to said mammal a therapeutically effective amount of a compound of the present invention, or a pharmaceutically acceptable salt, prodrug or hydrate thereof.

The invention also relates to a use of treating diseases related to vasculogenesis or angiogenesis in a mammal that comprises administering to said mammal a therapeutically effective amount of a compound of the present invention, or a pharmaceutically acceptable salt, prodrug or hydrate thereof. In one embodiment, said method is for treating a disease selected from the group consisting of tumor angiogenesis, chronic inflammatory disease such as rheumatoid arthritis, atherosclerosis, inflammatory bowel disease, skin diseases such as psoriasis, excema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer. Patients that can be treated with compounds of the present invention, or pharmaceutically acceptable salts, prodrugs and hydrates of said compounds, according to the methods of this invention include, for example, patients that have been diagnosed as having psoriasis, restenosis, atherosclerosis, BPH, lung cancer, bone cancer, CMML, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, testicular, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

This invention also relates to a compound or pharmaceutical composition for inhibiting abnormal cell growth in a mammal which comprises an amount of a compound of the present invention, or a pharmaceutically acceptable salt or solvate or prodrug thereof, in combination with an amount of a chemotherapeutic, wherein the amounts of the compound, salt, solvate, or prodrug, and of the chemotherapeutic are together effective in inhibiting abnormal cell growth. Many chemotherapeutics are presently known in the art. In one embodiment, the chemotherapeutic is selected from the group consisting of mitotic inhibitors, alkylating agents, antimetabolites, intercalating antibiotics, growth factor inhibitors, cell cycle inhibitors, enzymes, topoisomerase inhibitors, biological response modifiers, anti-hormones, angiogenesis inhibitors, and anti-androgens. This invention further relates to a method for inhibiting abnormal cell growth in a mammal or treating a hyperproliferative disorder which method comprises administering to the mammal an amount of a compound of the present invention, or a pharmaceutically acceptable salt or solvate or prodrug thereof, in combination with radiation therapy, wherein the amounts of the compound, salt, solvate, or prodrug, is in combination with the radiation therapy effective in inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein. It is believed that the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of the present invention or pharmaceutically acceptable salt or solvate or prodrug thereof, which amount is effective is sensitizing abnormal cells to treatment with radiation. The amount of the compound, salt, or solvate in this method can be determined according to the means for ascertaining effective amounts of such compounds described herein. The invention also relates to a method of and to a pharmaceutical composition of inhibiting abnormal cell growth in a mammal which comprises an amount of a compound of the present invention, or a pharmaceutically acceptable salt or solvate thereof, a prodrug thereof, or an isotopically-labeled derivative thereof, and an amount of one or more substances selected from anti-angiogenesis agents, signal transduction inhibitors, and antiproliferative agents.

In practical use, the compounds of the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing cancer, inflammation or other proliferative diseases for which compounds of the present invention are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligram to about 50 milligrams. In the case of a 70 kg adult human, the total daily dose will generally be from about 7 milligrams to about 350 milligrams. This dosage regimen may be adjusted to provide the optimal therapeutic response.

Some abbreviations that may appear in this application are as follows.
Abbreviations
Designation
b Broad peak
CDI N,N-Carbonyldiimidazole
d Doublet
DCM Dichloromethane
dd double doublet
DIPEA N-Ethyldiisopropylamine
DMF N,N-Dimethylformamide
EDC 1-(3-Dimethylaminopropyl)-3-ethylcarbodiimide hydrochloride
HPLC High pressure liquid chromatography
LiHMDS. Lithium hexamethyldisilazide
MCPBA 3-Chloroperoxybenzoic acid
NMR Nuclear Magnetic Resonance
PG Protecting group
PyBOP Benzotriazole-1-yl-oxy-trispyrrolidinophosphonium hexafluorophosphate
q Quartett
rt Retention time
s Singlet
tert Tertiary-butyl
TFA Trifluoroacetic acid
THF Tetrahydrofurane
TLC Thin Layer Chromatography The compounds of the present invention can be prepared according to the procedures of the following Schemes and Examples, using appropriate materials and are further exemplified by the following specific examples. Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described above. The amine-free bases corresponding to the isolated salts can be generated by neutralization with a suitable base, such as aqueous sodium hydrogencarbonate, sodium carbonate, sodium hydroxide and potassium hydroxide, and extraction of the liberated amine-free base into an organic solvent, followed by evaporation. The amine-free base, isolated in this manner, can be further converted into another pharmaceutically acceptable salt by dissolution in an organic solvent, followed by addition of the appropriate acid and subsequent evaporation, precipitation or crystallization.

An illustration of the preparation of compounds of the present invention is shown in schemes 2 and 3. Unless otherwise indicated in the schemes, the variables have the same meaning as described above.

The examples presented below are intended to illustrate particular embodiments of the invention.

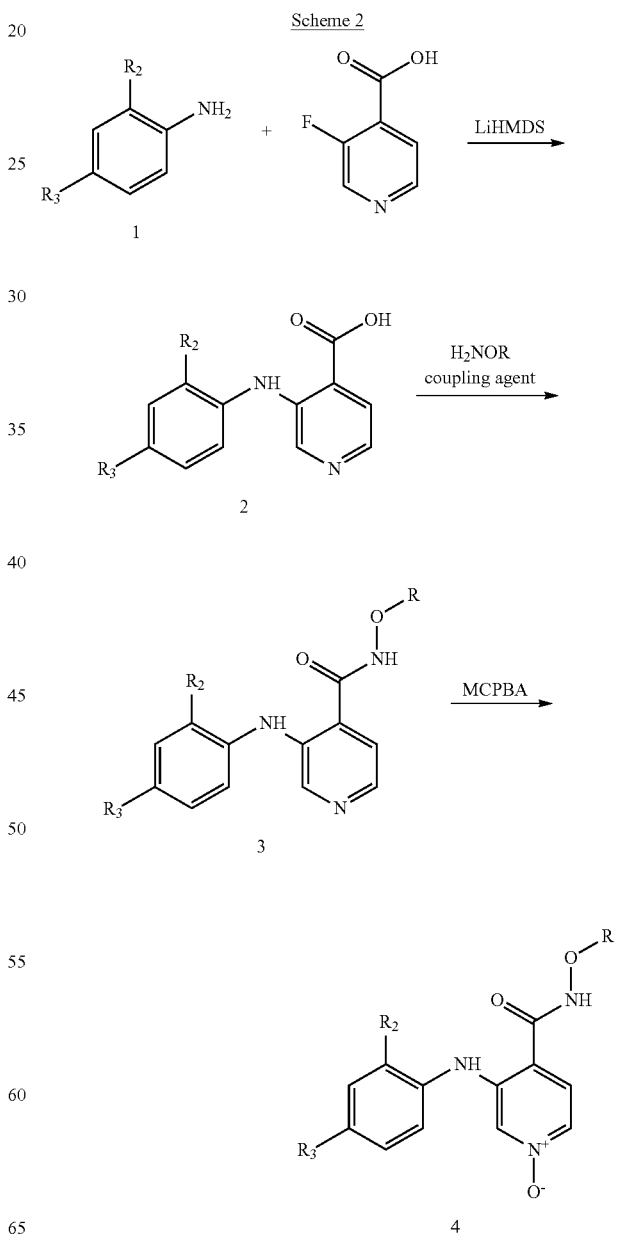

Scheme 3

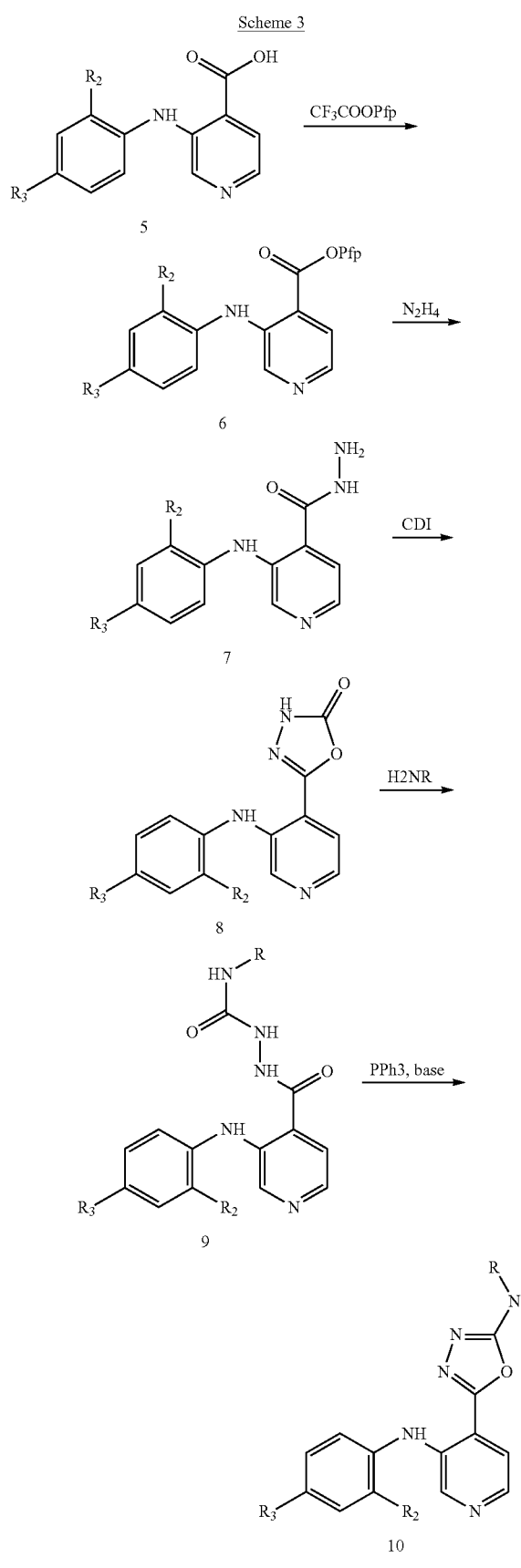

Scheme 2 illustrates the synthesis of compounds in the present invention. In step 1 the aniline 1 is reacted with 3-fluoro isonicotinic acid in an inert solvent, preferable THF, by addition of a base, preferably but not limited to LiHMDS. In step 2 the 3-anilino isonicotinic acid 2 is coupled with an O-alkyl hydroxalamine using an appropriate coupling reagent including but not limited to PyBOP; EDC or DCC in a suitable organic solvents like for example DMF, THF or DCM to yield hydroxamate 3. Compound 3 is then converted into the corresponding pyridine N-oxide 4 by using oxidation reagents as for example MCPBA or peracetic acid in a suitable solvent like for example THF or DCM.

Suitable anilines and isonicotinic acid derivatives are commercially available from Sigma-Aldrich Chemie GmbH, Munich, Germany or from Acros Organics, Belgium or from Fisher Scientific GmbH, 58239 Schwerte, Germany or can be routinely prepared by procedures described in "March's Advanced Organic Chemistry: Reactions, Mechanisms, and Structure", 5th Edition; John Wiley & Sons. Scheme 3 illustrates the preparation of compounds of the present invention where W is heterocyclic. In step 1 the 3-anilino isonicotinic acid derivative 5 is reacted with pentafluorophenyl trifluoroacetate and a base, for example pyridine, to give the active ester 6 which is further converted in step 2 to hydrazide 7 by reacting it with hydrazine or hydrazine hydrate in an inert solvent such as DCM, DMF or THF. Reaction of 7 with CDI or any suitable carbonate equivalent in a preferred solvent such as DMF or DCM for example then gives Oxadiazolone 8, which forms N-substituted hydrazinecarboxamides 9 when treated with a substituted amine in ethanol. Cyclization is achieved by addition of triphenylphosphine and a base such as triethylamine or DIPEA in an inert solvent like $CCl_4$ for example to give compound 10.

Compounds with other variants in the position of W can be prepared by derivatizing the COOH group appropriately as known to the person skilled in the art as described in Theophil Eicher, Siegfried Hauptmann "The Chemistry of Heterocycles; Structures, Reactions, Synthesis and Application", $2^{nd}$ edition, Wiley-VCH 2003. The introduction of alternative heterocyclic or heteroaryl groups is exemplified e.g. in WO 03/077855 and WO 01/05391.

Unless otherwise noted, all non-aqueous reactions were carried out either under an argon or nitrogen atmosphere with commercial dry solvents. Compounds were purified using flash column chromatography using Merck silica gel 60 (230-400 mesh), or by reverse phase preparative HPLC using a Reprosil-Pur ODS3, 5 μm, 20×125 mm column with Shimadzu LC8A-Pump and SPD-10Avp UV/Vis diode array detector. The $^1$H-NMR spectra were recorded on a Varian VXR-S (300 MHz for $^1$H-NMR) using $d_6$-dimethylsulfoxide or $d_4$-methanol as solvent; chemical shifts are reported in ppm relative to tetramethylsilane. Analytical LC/MS was performed using Reprosil-Pur ODS3, 5 μM, 1×60 mm columns at a flow rate of 250 μl/min, sample loop 2.5 μl; retention times are given in minutes. Methods are: (I) runs on a LC10Advp-Pump (Shimadzu) with SPD-M10Avp UVN is diode array detector and QP2010 MS-detector in ESI+ modus with UV-detection at 214, 254 and 275 nm with a gradient of 15-95% acetonitrile (B) in water (A) (0.1% formic acid), 5 min. linear gradient; (II) idem but linear gradient 8 min 1-30% B; (III) idem but linear gradient 8 min 10-60% B; (IV) idem but linear gradient 8 min 15-99% B; (V) idem but linear gradient 5 min 10-90% B; (VI) idem but linear gradient 5 min 5-95% B.

EXAMPLES

The examples presented below are intended to illustrate particular embodiments of the invention, and are not intended to limit the scope of the specification or the claims in any way.

Example 1

3-[(2,4-Dichlorophenyl)amino]isonicotinic acid (2a)

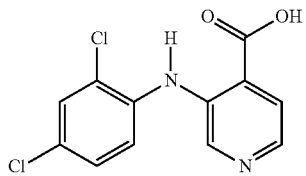 [SMILES: O=C(O)c1ccncc1Nc1ccc(Cl)cc1Cl]

2,4-Dichloraniline (162 mg, 1.00 mmol) and 3-fluoropyridine-4-carboxylic acid (141 mg, 1.00 mmol) were dissolved in dry THF (6.0 ml) under argon and the mixture was cooled to −78° C. A solution of LiHMDS (1.0M in THF, 3.5 ml) was added and the reaction mixture was allowed to warm to ambient temperature. After 18 h the reaction was quenched by adding a solution of HCl in dioxane (4.0M, 2.0 ml). The volatiles were removed in vacuo and the crude material was purified by flash chromatography using silica gel and a gradient of 0-10% methanol in DCM as eluent to give 204 mg (721 μmol; 72% yield) of pure desired product.

LC-MS (method I): rt=2.98 min; m/z [M+I-1]$^+$ 282.9; $^1$H-NMR (300 MHz, DMSO-d$_6$): δ=7.72 (1H, dd, J=2.2 Hz, J=8.8 Hz); 7.48 (1H, d, J=8.8 Hz); 7.53 (1H, d, J=2.9 Hz); 7.71 (1H, d, J=4.4 Hz); 7.99 (1H, d, J=5.1 Hz); 8.46 (1H, s); 11.3 (1H, b).

Example 2

3-[(4-Bromo-2-methylphenyl)amino]isonicotinic acid (2b)

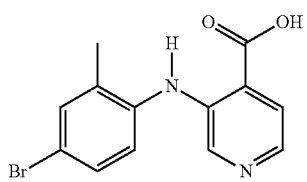

4-Bromo-2-methylaniline (186 mg, 1.00 mmol) and 3-fluoropyridine-4-carboxylic acid (141 mg, 1.00 mmol) were dissolved in dry THF (6.0 ml) under argon and the mixture was cooled to −78° C. A solution of LiHMDS (1.0M in THF, 3.5 ml) was added and the reaction mixture was allowed to warm to ambient temperature. After 24 h the reaction was quenched by adding a solution of HCl in dioxane (4.0M, 2.0 ml). The volatiles were removed in vacuo and the crude material was purified by flash chromatography using silica gel and a gradient of 0-10% methanol in DCM as eluent to give 215 mg (701 μmol; 70% yield) of pure desired product.

LC-MS (method I): rt 1.57 min; m/z [M+H]$^+$ 306.7; $^1$H-NMR (300 MHz, DMSO-d$_6$): δ=2.23 (3H, s); 3.62 (1H, b); 7.27 (2H, s); 7.38 (1H, s); 7.65 (1H, d, J=4.1 Hz); 7.91 (1H, d, J=7.9 Hz); 8.45 (1H, s).

Example 3

3-[(4-Iodo-2-methylphenyl)amino]isonicotinic acid (2c)

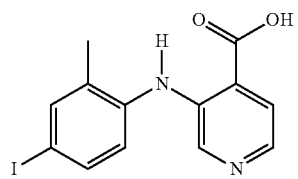 [SMILES: Cc1cc(I)ccc1Nc1cnccc1C(=O)O]

4-Iodo-2-methylaniline (233 mg, 1.00 mmol) and 3-fluoropyridine-4-carboxylic acid (141 mg, 1.00 mmol) were dissolved in dry THF (6.0 ml) under argon and the mixture was cooled to −78° C. A solution of LiHMDS (1.0M in THF, 3.5 ml) was added and the reaction mixture was allowed to warm to ambient temperature. After 36 h the reaction was quenched by adding solid NH$_4$Cl. After filtration the volatiles were removed in vacuo and the crude material was purified by flash chromatography using silica gel and a gradient of 0-10% methanol in DCM as eluent to give 208 mg (588 μmol; 59% yield) of pure desired product.

LC-MS (method I): rt 1.69 min; m/z [M+H]$^+$ 395.8; $^1$H-NMR (300 MHz, DMSO-d$_6$): δ=2.20 (3H, s); 3.80 (1H, b); 7.15 (1H, d, J=8.8 Hz); 7.20 (1H, b); 7.48 (1H, dd, J=8.1 Hz, J=2.2 Hz); 7.61 (1H, d, J=1.5 Hz); 7.66 (1H, d, J=5.1 Hz); 7.97 (1H, d, J=4.4 Hz); 8.30 (1H, s).

Example 4

3-[(4-Bromo-2-methylphenyl)amino]-N-ethoxyisonicotinamide (3b)

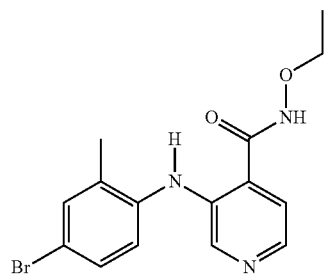 [SMILES: CCONC(=O)c1ccncc1Nc1ccc(Br)cc1C]

3-[(4-Bromo-2-methylphenyl)amino]isonicotinic acid 2b (320 mg, 1.04 mmol) was dissolved in 15 ml dry DMF followed by the addition of DIPEA (2.08 mmol, 373 μl), ByBOP (1.25 mmol, 651 mg) and O-ethylhydroxylamine hydrochloride (2.08 mmol, 203 mg). The mixture was stirred for 2 h and the volatiles were removed in vacuo. The crude material was purified by flash chromatography using silica gel and a gradient of 0-5% methanol in DCM as eluent to give 280 mg (800 μmol; 77% yield) of pure desired product.

LC-MS (method I): rt 1.90 min; m/z [M+H]$^+$ 351.9; $^1$H-NMR (300 MHz, DMSO-d$_6$): δ=1.20 (3H, t, J=6.6 Hz); 2.21 (3H, s); 3.91 (2H, q, J=6.6 Hz); 7.20 (1H, d, J=8.8 Hz);

7.34 (1H, dd, J=8.8 Hz, J=2.2 Hz); 7.42 (1H, d, J=5.1 Hz); 7.47 (1H, d, J=2.2 Hz); 8.08 (1H, d, J=5.1 Hz); 8.35 (1H, s); 8.70 (1H, b).

Example 5

N-Ethoxy-3-[(4-iodo-2-methylphenyl)amino]isonicotinamide (3c)

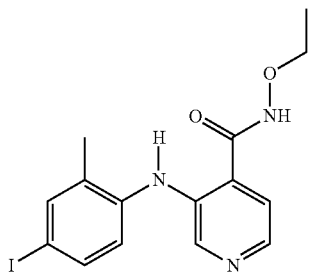 [SMILES: CCONC(=O)c1ccncc1Nc1ccc(I)cc1C]

3-[(4-iodo-2-methylphenyl)amino]isonicotinic acid 2c (60 mg, 0.17 mmol) was dissolved in 6 ml dry DMF followed by the addition of DIPEA (0.20 mmol, 37 µl), ByBOP (0.20 mmol, 107 mg) and O-ethylhydroxylamine hydrochloride (0.34 mmol, 34 mg). The mixture was stirred for 4 h and the volatiles were removed in vacuo. The crude material was purified by preparative reversed phase HPLC to give 36 mg (91 µmol; 53% yield) of pure desired product.

LC-MS (method I): rt 2.14 min; m/z [M+H]$^+$ 397.9; $^1$H-NMR (300 MHz, DMSO-d$_6$): δ=1.20 (3H, t, J=7.3 Hz); 2.19 (3H, s); 3.40 (b); 3.90 (2H, q, J=7.3 Hz); 7.07 (1H, d, J=8.8 Hz); 7.42 (1H, d, J=5.1 Hz); 7.48 (1H, 2, J=7.3 Hz); 8.08 (1H, d, J=4.4 Hz); 8.37 (1H, s); 8.71 (1H, b).

Example 6

3-[(4-Bromo-2-methylphenyl)amino]-N-ethoxyisonicotinamide 1-oxide (4b)

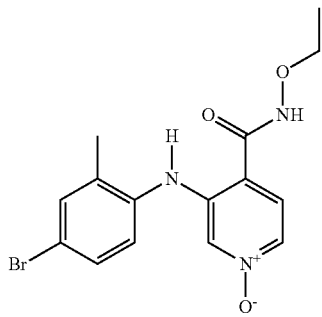 [SMILES: CCONC(=O)c1cc[n+]([O-])cc1Nc1ccc(Br)cc1C]

3-[(4-Bromo-2-methylphenyl)amino]-N-ethoxyisonicotinamide 3b (80.0 mg, 0.228 mmol) was dissolved in 4 ml dry DCM and 3-chloroperbenzoic acid (73% pure, 60 mg) was added at ambient temperature. After 2 h the solvent was removed in vacuo and the crude material was purified by flash chromatography using silica gel and a gradient of 0-10% methanol in DCM as eluent to give 37 mg (101 µmol; 44% yield) of pure desired product.

LC-MS (method III): rt 4.47 min; m/z [M+H]$^+$ 366.0; $^1$H-NMR (300 MHz, DMSO-d$_6$): δ=1.22 (3H, t, J=7.3 Hz); 2.21 (3H, s); 3.94 (2H, q, J=7.3 Hz); 7.27 (1H, d, J=8.8 Hz); 7.41 (1H, dd, J=8.8 Hz, J=2.2 Hz); 7.51 (1H, d, J=6.6 Hz); 7.55 (1H, dd, J=10.3 Hz, J=2.2 Hz); 7.68 (1H, dd, J=6.6 Hz, J=2.2 Hz); 9.31 (1H, b).

General Method 1:

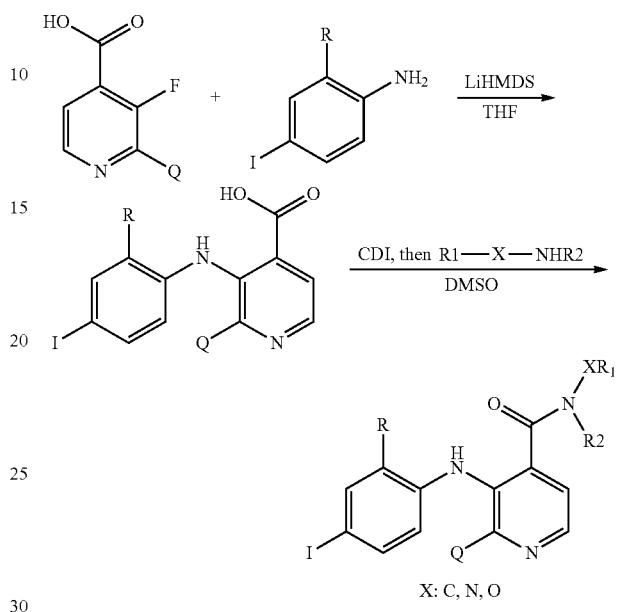

Q examples: Cl, Me
R examples: F, Cl, Me, H etc.

General Method 1 starts with the reaction of various 3-halogenated isonicotonic acids with substituted anilines in the presence of base. The resulting acids were further derivatized by reaction with 1,1 carbonyldiimidazole in DMSO followed by addition of the desired nucleophile.

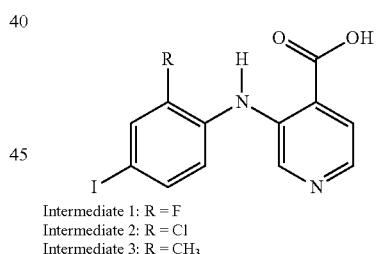

Intermediate 1: R = F
Intermediate 2: R = Cl
Intermediate 3: R = CH$_3$

Intermediate 1

3-[(2-fluoro-4-iodophenyl)amino]isonicotinic acid (R=fluoro)

A mixture of 2-fluoro-4-iodoaniline (20.0 g, 84.38 mmol) in dry THF (80 mL) was cooled to −67° C. (dry ice/IPA bath) under nitrogen, prior to slow addition of 1.0 M lithium bis(trimethylsilyl)amide (255 mL, 255 mmol) via addition funnel, at a rate that kept the internal temp below −59° C. (~2 h). After final addition, the yellow-green slurry was stirred for 30 min and then treated with 2-fluoroisonicotinic acid (8.0 g, 56.69 mmol). The bath was not removed, but the contents were allowed to slowly warm to room temp. After 4 days, the dark slurry was poured into a biphasic mixture of aqueous 2.0 N sodium hydroxide (1000 mL) and ethyl acetate (150 mL).

The aqueous layer was separated and the organics were again extracted with base (1000 mL). The pH of the two aqueous layers was adjusted to ~2 with concentrated hydrochloric acid. A yellow solid precipitated, which was filtered. The resultant yellow cake was washed with water (2×400 mL) and dried under high vacuum at 40° C. (17-19 g). LC/MS [(5.2 min; 359 (M+1)].

Intermediate 2

3-[(2-chloro-4-iodophenyl)amino]isonicotinic acid (R=chloro) :synthesized as intermediate 1 by reacting 15.7 mmol of 2-chloro-4-iodoaniline with 23.55 mmol 2-fluoroisonicotinic acid. LC/MS [(5.9 min; 376 (M+1)].

Intermediate 3

3-[(2-methyl-4-iodophenyl)amino]isonicotinic acid (R=methyl) :synthesized as intermediate 1 by reacting 4.7 mmol of 2-methyl-4-iodoaniline with 7.0 mmol 2-fluoroisonicotinic acid. LC/MS [(5.3 min; 355 (M+1)]. See detailed procedure in Example 3.

Synthesis of MEK Inhibitors; General Procedure for carboxylic acid Derivatization of 3-phenylamino-isonicotinic acids

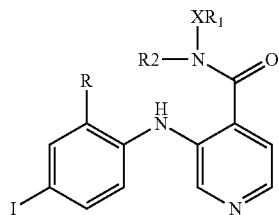

The carboxylic acid (see intermediates 1-3) (0.2-8 mmol) and CDI (1,1 carbonyldiimidazole) (1.3 eq) in dry DMSO (10-20 volumes) was stirred at room temp (13-18 h). The dark-yellow solution was then treated with a substituted amine, substituted hydrazine or O-substituted hydroxylamine (1-2 eq). The contents were stirred at room temp for 4-18 h and the resultant dark-yellow solution was poured into ethyl acetate, washed with brine and concentrated.

Method for the Synthesis of 3-phenylamino-1-oxy-isonicotinic acid Derivatives

General Method 2:

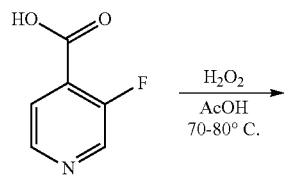

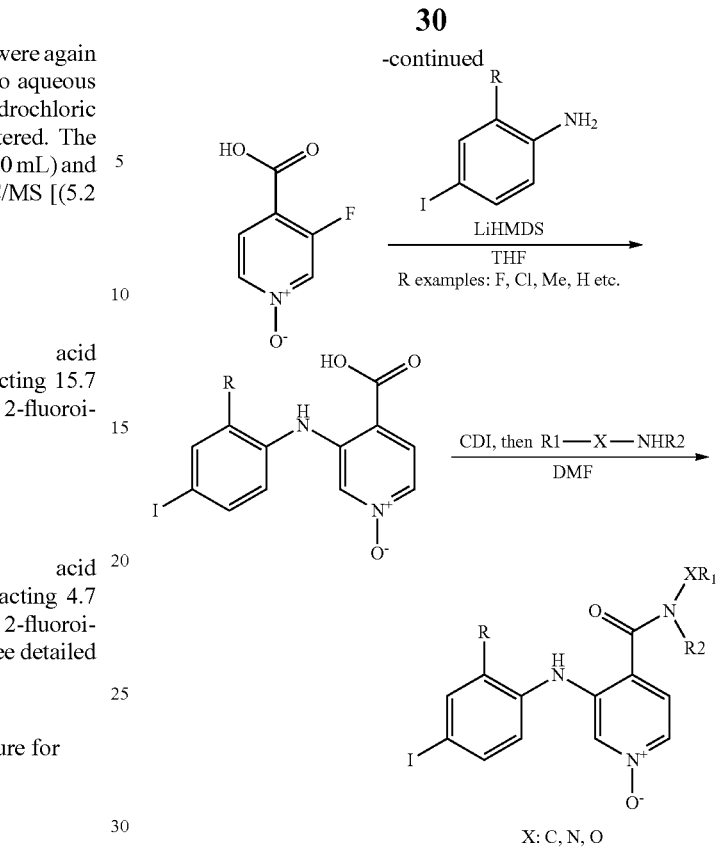

1-oxy derivatives were synthesized in a similar manner. First step in this synthesis was the N-oxidation of 3-fluoroisonicotinic acid. The subsequent steps were performed as previously described under General Method 1. Procedural details for this synthesis are as following:

3-fluoroisonicotinic acid 1-oxide

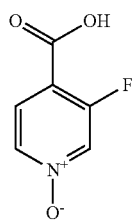 [SMILES: O=C(O)c1cc[n+]([O-])cc1F]

To a solution of 3-fluoroisonicotinic acid (5.0 g, 35.33 mmol) in acetic acid (25 ml) was added hydrogen peroxide (6 ml). The reaction mixture was stirred at 70-80° C. overnight. The solvent was removed to obtain 5.5 g of 3-fluoroisonicotinic acid 1-oxide in quantitative yield.

3-(2-Fluoro-4-iodo-phenylamino)-1-oxy-isonicotinic acid

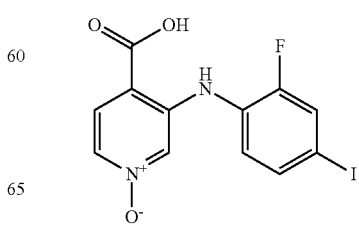

Lithium 1,1,1,3,3,3-hexamethyldisilazan-2-ide (62 ml, 62.0 mmol) was added to a solution of 2-fluoro-4-iodoaniline (7.24 g, 30.55 mmol) in THF at −78° C. The mixture was stirred for 90 min at −78° C., then another 1.2 equiv. of lithium 1,1,1,3,3,3-hexamethyldisilazan-2-ide (3r1 ml, 31.0 mmol) was added, following by 3-fluoroisonicotinic acid 1-oxide (4.0 g, 25.46 mmol). The reaction mixture was warmed to room temperature and stirred overnight. The solvent was evaporated, and water was added (50 ml). The pH of the aqueous layer was adjusted to <3, and washed with ether (20 ml×2). The product precipitated as a yellow solid. It was filtered, and dried to get 3.50 g of material. (36%) of 3-(2-Fluoro-4-iodophenylamino)-1-oxy-isonicotinic acid. LC/MS: [7.32 min; 374 (M+1)]

3-[(2-fluoro-4-iodophenyl)amino]isonicotinamide 1-oxide

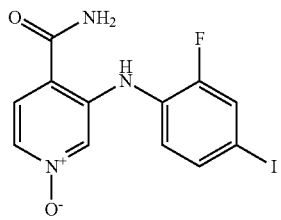 [SMILES: NC(=O)c1cc[n+]([O-])cc1Nc1ccc(I)cc1F]

3-(2-Fluoro-4-iodo-phenylamino)-1-oxy-isonicotinamide was synthesized according to the general procedure of Method 1 as, outlined above, starting with 110 mg (0.29 mmol) of 3-[(2-fluoro-4-iodophenyl)amino]isonicotinic acid 1-oxide and 56 mg (0.74 mmol) of ammonium acetate LC/MS: [7.32 min; 375 (M+1)]

Method for the Synthesis of 2-bromo-3-phenylamino-isonicotinic acid Derivatives

General Method 3:

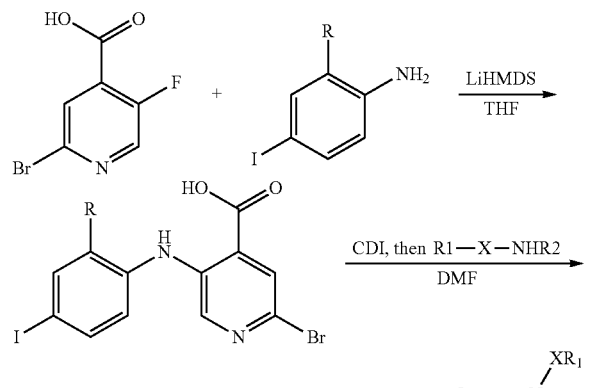

R examples: F, Cl, Me, H etc.
X: C, N, O

2-Bromo-3-phenylamino-isonicotinic acid derivatives were synthesized in a similar manner. A typical procedure for the synthesis of such analogs follows below:

2-Bromo-5-(2-fluoro-4-iodo-phenylamino)-isonicotinic acid

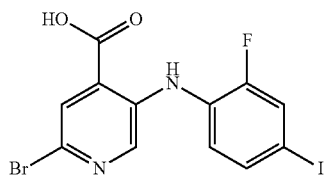 [SMILES: O=C(O)c1cc(Br)ncc1Nc1ccc(I)cc1F]

Lithium 1,1,1,3,3,3-hexamethyldisilazan-2-ide (11.9 ml, 1.00 M, 11.82 mmol) was added to a solution of 2-fluoro-4-iodoaniline (1.40 g, 5.91 mmol) at −78° C. The pale green colored solution was stirred for 1½ h at −78° C. Then, lithium 1,1,1,3,3,3-hexamethyldisilazan-2-ide (5.45 ml, 1.00 M, 5.45 mmol) was added followed by 2-bromo-5-fluoroisonicotinic acid (1.00 g, 4.55 mmol) in THF (5 ml). The dark colored homogeneous mixture was warmed to room temperature and stirred overnight. The crude was diluted with EtOAc (300 ml). Then, it washed with dilute HCl solution (20 ml), H$_2$O (20 ml), dried and purified on Flashmaster II using a 100 g cartridge to obtain 1.18 g (59%) of 2-Bromo-5-(2-fluoro-4-iodo-phenylamino)-isonicotinic acid. LC/MS: 7.43 min, 438 (M+1)

2-Bromo-5-(2-fluoro-4-iodo-phenylamino)-isonicotinamide

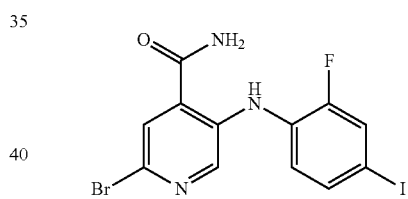

To a solution of 2-bromo-5-[(2-fluoro-4-iodophenyl)amino]isonicotinic acid (145.0 mg, 0.33 mmol) in N,N-dimethylformamide (1.50 ml), 1,1'-carbonylbis(1H-imidazole) (60 mg, 0.36 mmol) was added, and the mixture was stirred at room temperature for 7 hours to obtain a homogeneous solution. Ammonium acetate (65 mg, 0.83 mmol) was added, and stirred for 2 h. Water (10 ml) was added, and the precipitated solid was filtered, washed with hot methanol to obtain 2-Bromo-5-(2-fluoro-4-iodo-phenylamino)-isonicotinamide as an yellow solid (85 mg, 58%) LC/MS: [9.59 min; 436, 438]

Method for the Synthesis of 2-alkyl-3-phenylamino-isonicotinic acid Derivatives

General Method 4:

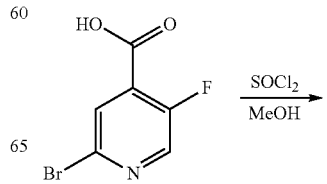

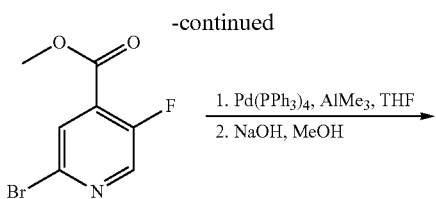

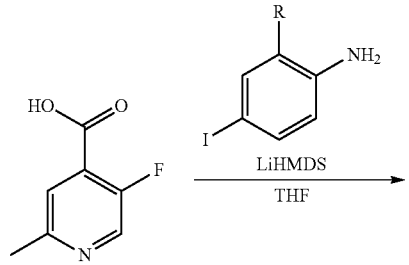

R examples: F, Cl, Me, H etc.

A typical procedure for the synthesis of 2-alkyl-3-phenylamino-isonicotinic acid derivatives:

Methyl 2-bromo-5-fluoroisonicotinate

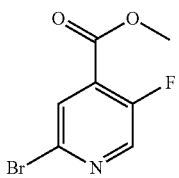

To a solution of 2-bromo-5-fluoroisonicotinic acid (1.5 g, 6.82 mmol) in methanol (75 ml), thionyl dichloride (2.5 ml, 34.09 mmol) was added drop-wise. The reaction mixture was stirred overnight. The solvent was removed under high vacuum. The residual solid was distilled at 90° C. under vacuum to get 1.3 g (81%) of pure methyl 2-bromo-5-fluoroisonicotinate:

Methyl 5-fluoro-2-methylisonicotinate

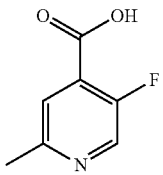

To a solution of methyl 2-bromo-5-fluoroisonicotinate (1.0 g, 4.27 mmol) in tetrahydrofuran (25 ml) tetrakis(triphenylphosphine)palladium (495.0 mg, 0.43 mmol) was added. The mixture was stirred for 10 min, and then trimethylaluminum (5.13 ml, 1.00 M in heptane, 5.13 mmol) was added. The mixture was refluxed for 4 h, and the reaction was monitored by TLC (10% EtOAc-Hexane). Then, the reaction was diluted with EtOAc (75 ml) and a few drops of saturated. ammonium chloride were added.

The mixture was filtered through a small silica gel pad, followed by removal of the solvent. The crude product was re-dissolved in 5N NaOH solution in water and stirred at room temperature for 2 hours. The crude product was purified on Flashmaster II to afford 250 mg of 5-fluoro-2-methylisonicotinic acid.

5-[(2-fluoro-4-iodophenyl)amino]-2-methylisonicotinic acid

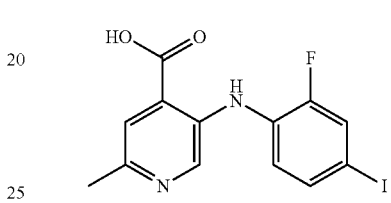

5-[(2-fluoro-4-iodophenyl)amino]-2-methylisonicotinic acid was synthesized according to the general procedure of Method 1 as, outlined above, starting with 200 mg (1.29 mmol) of 5-fluoro-2-methylisonicotinic acid, 370 mg (1.55 mmol) of 2-fluoro-4-iodoaniline and two portions of lithium bis(trimethylsilyl)amide (3.35 ml, 3.35 mmol), and (1.55 ml, 1.55 mmol). Yield: 30 mg, 6%, LC/MS [5.5 min; 473 (M+1)]

Method for the Synthesis of 2-aryl-3-phenylamino-isonicotinic acid Derivatives

General Method 5:

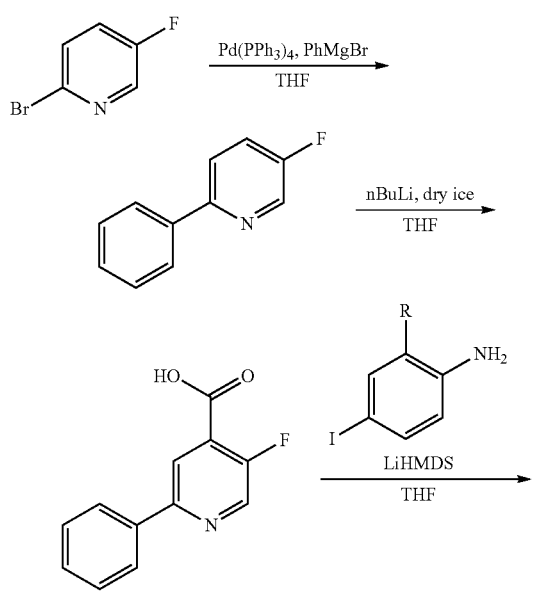

5-[(2-fluoro-4-iodophenyl)amino]-2-phenylisonicotinic acid

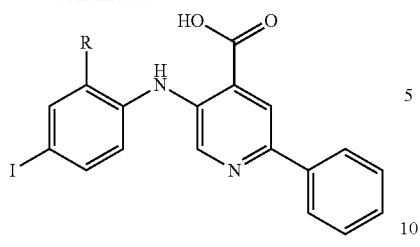

R examples: F, Cl, Me, H etc.

A typical procedure for the synthesis of 2-alkyl-3-phenylamino-isonicotinic acid derivatives:

5-fluoro-2-phenylpyridine

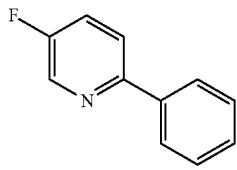

To a solution of 2-bromo-5-fluoropyridine (10.0 g, 56.82 mmol, Aldrich) in tetrahydrofuran (100 ml) was added tetrakis(triphenylphosphine)Pd complex and stirred for 10 min. Then, phenylmagnesium bromide (68.2 ml, 1.00 M in THF, 68.19 mmol) was added drop-wise at 0° C. The mixture was stirred overnight. Then the reaction was diluted with EtOAc (600 ml), and filtered. The filtrate was concentrated and purified by flash chromatography by eluting with 2% EtOAc-Hexane to obtain 6.8 g (69%) of 5-fluoro-2-phenylpyridine.

5-fluoro-2-phenylisonicotinic acid

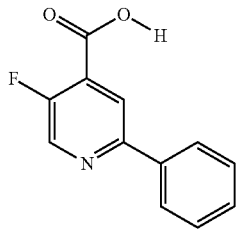 [SMILES: O=C(O)c1cc(-c2ccccc2)ncc1F]

To a solution of 5-fluoro-2-phenylpyridine (760.0 mg, 4.39 mmol) in tetrahydrofuran (15.0 ml) was added n-butyllithium (2.11 ml, 2.50 M in THF, 5.27 mmol) at −45° C. The mixture was stirred for 1 h at −45° C., then poured into THF containing dry ice. Stirred for 1 h, then MeOH (2 ml) was added. The solution was concentrated, and purified on Flashmaster II to get 560 mg (58%) of 5-fluoro-2-phenylisonicotinic acid.

5-[(2-fluoro-4-iodophenyl)amino]-2-phenylisonicotinic acid

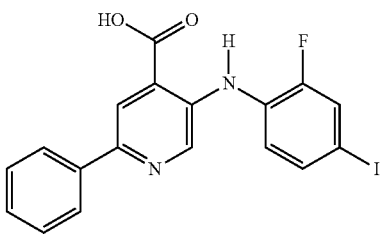 [SMILES: O=C(O)c1cc(-c2ccccc2)ncc1Nc1ccc(I)cc1F]

Lithium bis(trimethylsilyl)amide (2.8 ml, 1.0 M in THF, 2.76 mmol) was added to a suspension of 5-fluoro-2-phenylisonicotinic acid (500 mg, 2.30 mmol) in THF (10 ml) at −78° C. The dark colored suspension was stirred for 30 min. In another flask, 2-fluoro-4-iodoaniline (709.30 mg, 2.99 mmol, 1.30 eq) was dissolved in (15 ml) THF and cooled to −78° C. To this solution lithium bis(trimethylsilyl)amide (5 ml, 1.00 M, 5.06 mmol, 2.20 eq) was added and the mixture was stirred for 1 h. The reaction mixture became very viscous. To this, the homogeneous solution of acid-LiHMDS mixture was added via syringe. The mixture was warmed to room temperature and stirred overnight. Diluted with EtOAc (300 ml), washed with dilute HCl (20 ml), water (20 ml), and then dried and concentrated. Purified on Flashmaster using 100 g cartridge to obtain 565 mg of 5-[(2-fluoro-4-iodophenyl)amino]-2-phenylisonicotinic acid. LC/MS: [8.59 min; 435 (M+1)]

Example 7

N-{[(2R)-2,3-dihydroxypropyl]oxy}-3-[(2-fluoro-4-iodophenyl)-amino]isonicotin-amide

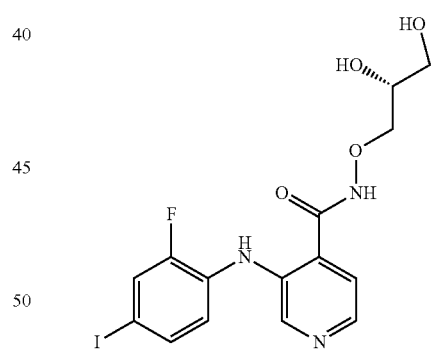

A suspension of N-{[(4R)-2,2-dimethyl-1,3-dioxolan-4-yl]methoxy}-3-[(2-fluoro-4-iodophenyl)amino]isonicotinamide (synthesis described below) (3.0 g, 6.16 mmol) in dichloromethane (20 mL) was treated with trifluoroacetic acid (20 mL) and the clear-yellow solution was stirred at room temp. After stirring for 8 h, the contents were concentrated to a yellow oil, which was dissolved in ethyl acetate (100 mL) and poured into water (150 mL). The pH of the biphasic mixture was adjusted between 6 and 7 with 2.0 N aqueous sodium hydroxide and the layers were separated. The organics were dried over sodium sulfate, concentrated to a yellow oil and placed under high vacuum at 40° C. The resultant yellow, solid foam weighed 2.39 g (5.34 mmol, 87%) after drying for 18 h. LC/MS [5.22 min; 448 (M+1)]

N-{[(2R)-2,3-dihydroxypropyl]oxy}-3-[(2-fluoro-4-iodophenyl)-amino]isonicotin-amide hydrochloride The diol from the previous entry (2.09 g, 4.67 mmol) was suspended in water (20 mL) and treated with aqueous 1.0 N HCl (4.7 mL). Complete dissolution occurred and the solution was placed on the lyophilizer. After 18 h, the yellow solid weighed 2.23 g (4.61 mmol, 99%). LC/MS [5.22 min; 448 (M+1)]

Example 7a

N-{[(4R)-2,2-dimethyl-1,3-dioxolan-4-yl]methoxy}-3-[(2-fluoro-4-iodophenyl)amino]isonicotinamide

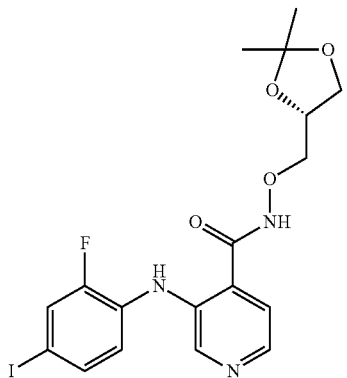 [SMILES: CC1(C)OC[C@H](CONC(=O)c2ccncc2Nc2ccc(I)cc2F)O1]

A mixture of the carboxylic acid Intermediate 1 (3.00 g, 8.38 mmol) and CDI (1.70 g, 10.48 mmol) was suspended in dry DMSO (40 mL) and the contents were stirred at room temp for 15 h. At that time, the dark-yellow solution was treated with the amine (2.05 g, 13.93 mmol) and the contents were stirred at room temp for 5 h and then poured into brine (250 mL) and extracted with ethyl acetate (250 mL). The organics were washed with brine (2×250 mL), dried over sodium sulfate and concentrated to a solid (3.06 g, 75%). LC/MS [6.03 min; 488 (M+1)]

3-[(2-chloro-4-iodophenyl)amino]isonicotinic acid

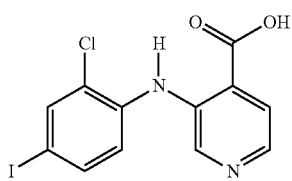 [SMILES: O=C(O)c1ccncc1Nc1ccc(I)cc1Cl]

To suspension of 3-fluoroisonicotinic acid (2.00 g, 14.17 mmol, in tetrahydrofuran (50 ml) at −78° C. was added lithium bis(trimethylsilyl)amide (14.3 ml, 17.01 mmol). The dark colored suspension was stirred for 15 min. In another flask, to a solution of 2-chloro-4-iodoaniline (4.7 g, 18.43 mmol) in THF (50 ml) was added lithium bis(trimethylsilyl) amide (24.9 ml, 29.77 mmol) at −78° C. under $N_2$. The resulting green colored solution was stirred for 15 min. To this green colored solution the lithiated acid solution was added. The cold bath was removed, allowed to warm to room temperature, and stirred overnight. The mixture was filtered, and the crude was diluted with EtOAc (400 ml). It was then washed with dilute HCl (25 ml), $H_2O$ (25 ml), and dried. During concentration of the solvent, 3-[(2-chloro-4-iodophenyl)amino]isonicotinic acid was separated out as an yellow solid. (1.3 g, 24%)

Example 7b

3-[(2-chloro-4-iodophenyl)amino]-N-{[(4R)-2,2-dimethyl-1,3-dioxolan-4-yl]methoxy}isonicotinamide

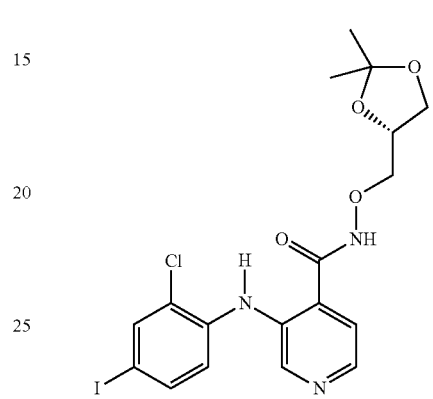

From the previous reaction 3-[(2-chloro-4-iodophenyl)amino]isonicotinic (120.00 mg, 0.32 mmol) acid was suspended in dichloromethane (5 ml). Pyridine (50.68 mg, 0.64 mmol) and N,N-Diisopropylethylamine (82.81 mg, 0.64 mmol) (DIEA helps to obtain a homogeneous solution) were added. To this mixture was added oxalyl chloride (121.99 mg, 0.96 mmol) and stirred for 1 h at room temperature. The mixture was concentrated, and the residue was dried under vacuum. The crude acid chloride was dissolved in DCM (5 ml) and DIEA was added (83 mg, 0.64 mmol,) followed by O-{[(4R)-2,2-dimethyl-1,3-dioxolan-4-yl]methyl}hydroxylamine (142 mg, 0.96 mmol,). The reaction mixture was stirred for 3 h, it concentrated, and purified on Flashmaster II to get 125 mg of 3-[(2-chloro-4-iodophenyl)amino]-N-{[(4R)-2,2-dimethyl-1,3-dioxolan-4-yl]methoxy}isonicotinamide in 77% yield.

Example 8

3-[(2-chloro-4-iodophenyl)amino]-N-{[(2R)-2,3-dihydroxypropyl]oxy}-isonicotinamide

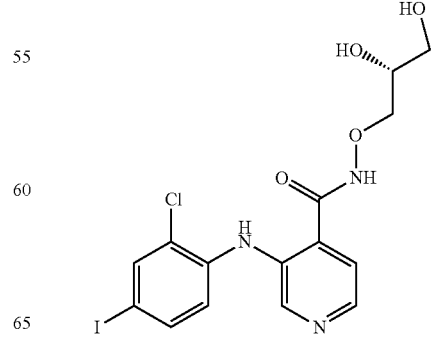

3-[(2-chloro-4-iodophenyl)amino]-N-{[(4R)-2,2-dimethyl-1,3-dioxolan-4-yl]methoxy}isonicotinamide (100.00 mg, 0.198 mmol.) from the reaction described above was dissolved in acetic acid (1 ml) was heated at 90° C. for 2 h. The reaction was monitored by HPLC. After completion, acetic acid was removed and the crude was purified on Flashmaster II to obtain 40 mg (43%) of 3-[(2-chloro-4-iodophenyl)amino]-N-{[(2R)-2,3-dihydroxypropyl]oxy}isonicotinamide. LC/MS: [7.97 min; 464, 466 (M+1)]

Example 9

3-[(2-methyl-4-iodophenyl)amino]-N-{[(2R)-2,3-dihydroxypropyl]oxy}-isonicotinamide

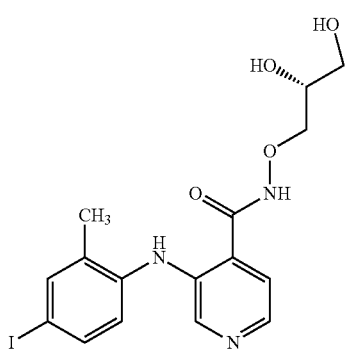 [SMILES: Cc1cc(I)ccc1Nc1cnccc1C(=O)NOC[C@H](O)CO]

3-[(2-methyl-4-iodophenyl)amino]-N-{[(2R)-2,3-dihydroxypropyl]oxy}isonicotinamide was synthesized as 3-[(2-chloro-4-iodophenyl)amino]-N-{[(2R)-2,3-dihydroxypropyl]oxy}isonicotinamide using Intermediate 3 instead of intermediate 2. LC/MS: [7.36 min; 464, 445 (M+1)]

Example 10

Methyl 3-[(2-chloro-4-iodophenyl)amino]isonicotinate

Carboxylic acid Intermediate 2 (0.200 g, 0.534 mmol) and CDI (0.095 g, 0.586 mmol) in dry DMSO (5 mL) was stirred at room temp for 18 h. The clear-yellow solution was then treated with dry methanol (0.5 mL) and 1,8-diazabicyclo[5.4.0]undec-7-ene (0.090 g. 0.591 mmol) and the contents were warmed to 50° C. After 2 days, the dark-yellow solution was poured into water and ethyl acetate. The layers were separated and the organics were washed with brine dried and concentrated to a yellow solid (0.207 g, 100%). LC/MS [8.20 min; 389 (M+1)]

Example 11

3-[(2-chloro-4-iodophenyl)amino]isonicotinamide

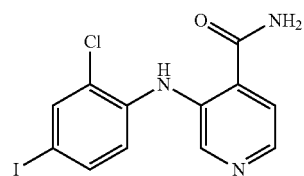 [SMILES: NC(=O)c1ccncc1Nc1ccc(I)cc1Cl]

3-[(2-chloro-4-iodophenyl)amino]isonicotinamide was synthesized according to the procedure for General Method 1, outlined above, starting with 6 mmol of 3-[(2-chloro-4-iodophenyl)amino]isonicotinic acid (intermediate 2) and 12 mmol of. ammonium acetate. LC/MS [8.29 min; 374 (M+1)]

3-[(2-chloro-4-iodophenyl)amino]isonicotinamide hydrochloride

The amide form the previous entry (4.5 mmol) was suspended in water (10 mL) and treated with aqueous 1.0 N HCl (9 mL). The contents were stirred for 15 min, cooled to 3° C. and filtered. The yellow-green solid was dried under high vacuum at 40° C.

LC/MS [8.29 min; 374 (free base, M+1)]

Example 12

3-[(2-fluoro-4-iodophenyl)amino]isonicotinamide

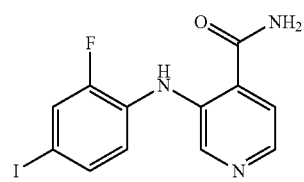 [SMILES: NC(=O)c1ccncc1Nc1ccc(I)cc1F]

3-[(2-fluoro-4-iodophenyl)amino]isonicotinamide was synthesized according to the procedure for General Method 1, outlined above, starting with 8 mmol of 3-[(2-fluoro-4-iodophenyl)amino]isonicotinic acid (intermediate 1) and 16 mmol of. ammonium acetate. LC/MS [7.27 min; 358 (M+1)].

3-[(2-fluoro-4-iodophenyl)amino]isonicotinamide hydrochloride

The amide form the previous entry (4 mmol) was suspended in water (12 mL) and treated with aqueous 1.0 N HCl (8 mL). The contents were stirred for 15 min, cooled to 3° C. and filtered. The yellow-green solid was dried under high vacuum at 40° C.

LC/MS [7.26 min; 358 (free base, M+1)]

Example 13

3-(2-Fluoro-4-iodo-phenylamino)-N-(2-morpholin-4-yl-ethyl)-isonicotinamide

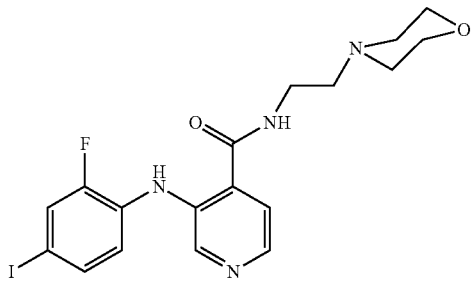 [SMILES: O=C(NCCN1CCOCC1)c1ccncc1Nc1ccc(I)cc1F]

3-(2-Fluoro-4-iodo-phenylamino)-N-(2-morpholin-4-yl-ethyl)-isonicotinamide was synthesized according to the procedure for General Method 1, outlined above, starting with 0.35 mmol of 3-[(2-fluoro-4-iodophenyl)amino]isonicotinic acid (intermediate 1) and 0.50 mmol of. 2-morpholin-4-yl-ethylamine LC/MS [1.74 min; 471 (M+1)].

Example 14

3-[(2-fluoro-4-iodophenyl)amino]-N-(2-hydroxypropyl)-isonicotinamide

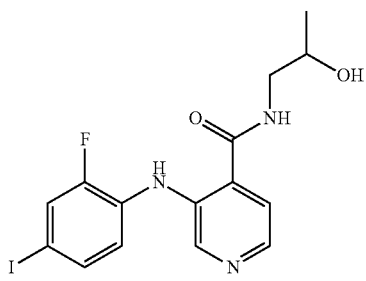 [SMILES: CC(O)CNC(=O)c1ccncc1Nc1ccc(I)cc1F]

3-[(2-fluoro-4-iodophenyl)amino]-N-(2-hydroxypropyl) isonicotinamide was synthesized according to the procedure for General Method 1, outlined above, starting with 0.45 mmol of 3-[(2-fluoro-4-iodophenyl)amino]isonicotinic acid (intermediate 1) and 0.62 mmol of 2-amino-isopropanol. LC/MS [5.11 min; 416 (M+1)]

Example 15

3-(2-Fluoro-4-iodo-phenylamino)-N-(2-hydroxy-ethyl)-isonicotinamide

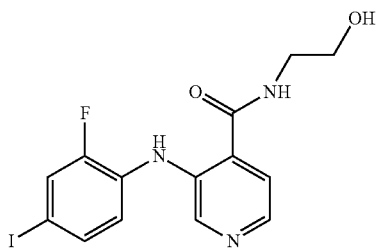 [SMILES: O=C(NCCO)c1ccncc1Nc1ccc(I)cc1F]

3-(2-Fluoro-4-iodo-phenylamino)-N-(2-hydroxy-ethyl)-isonicotinamide was synthesized according to the procedure for General Method 1, outlined above, starting with 0.39 mmol of 3-[(2-fluoro-4-iodophenyl)amino]isonicotinic acid (intermediate 1) and 0.50 mmol of ethanolamine. LC/MS [3.42 min; 402 (M+1)]

Example 16

3-(2-Fluoro-4-iodo-phenylamino)-N-(2-methoxy-ethyl)-isonicotinamide

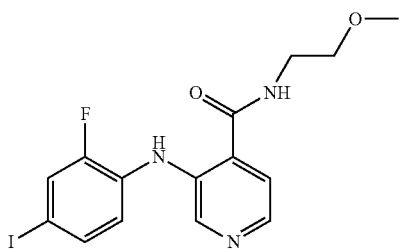 [SMILES: COCCNC(=O)c1ccncc1Nc1ccc(I)cc1F]

3-(2-Fluoro-4-iodo-phenylamino)-N-(2-hydroxy-ethyl)-isonicotinamide was synthesized according to the procedure for General Method 1, outlined above, starting with 0.45 mmol of 3-[(2-fluoro-4-iodophenyl)amino]isonicotinic acid (intermediate 1) and 0.60 mmol of 2-methoxy-ethylamine. LC/MS [3.42 min; 402 (M+1)]

Example 17

[3-(2-Fluoro-4-iodo-phenylamino)-pyridin-4-yl]-morpholin-4-yl-methanone

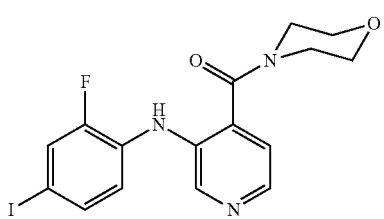 [SMILES: O=C(c1ccncc1Nc1ccc(I)cc1F)N1CCOCC1]

3-(2-Fluoro-4-iodo-phenylamino)-pyridin-4-yl]-morpholin-4-yl-methanone was synthesized according to the procedure for General Method 1, outlined above, starting with 0.36 mmol of 3-[(2-fluoro-4-iodophenyl)amino]isonicotinic acid (intermediate 1) and 0.47 mmol of morpholine. LC/MS [7.67 min; 428 (M+1)].

Example 18

N-ethyl-3-[(2-fluoro-4-iodophenyl)amino]isonicotinamide

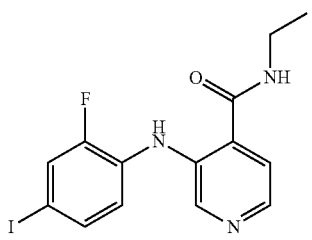 [SMILES: CCNC(=O)c1ccncc1Nc1ccc(I)cc1F]

N-ethyl-3-[(2-fluoro-4-iodophenyl)amino]isonicotinamide was synthesized according to the procedure for General Method 1, outlined above, starting with 0.34 mmol of 3-[(2-fluoro-4-iodophenyl)amino]isonicotinic acid (intermediate 1) and 0.48 mmol of monoethylamine. LC/MS [5.96 min; 386 (M+1)]

Example 19

3-[(2-fluoro-4-iodophenyl)amino]-N-piperidin-1-ylisonicotinamide

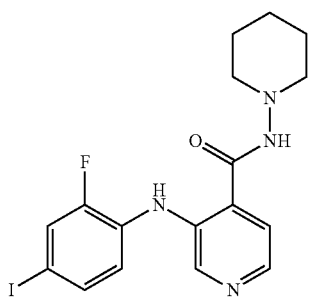 [SMILES: O=C(NN1CCCCC1)c1ccncc1Nc1ccc(I)cc1F]

3-[(2-fluoro-4-iodophenyl)amino]-N-piperidin-1-ylisonicotinamide was synthesized according to the procedure for General Method 1, outlined above, starting with 0.30 mmol of 3-[(2-fluoro-4-iodophenyl)amino]isonicotinic acid (intermediate 1) and 0.47 mmol of piperidin-1-ylamine LC/MS [8.81 min; 441 (M+1)]

Example 20

3-[(2-fluoro-4-iodophenyl)amino]-N-[3-(1H-imidazol-1yl)propyl]-isonicotinamide

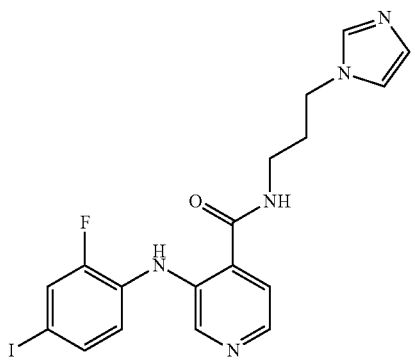 [SMILES: O=C(NCCCn1ccnc1)c1ccncc1Nc1ccc(I)cc1F]

3-[(2-fluoro-4-iodophenyl)amino]-N-[3-(1H-imidazol-1-yl)propyl]isonicotinamide was synthesized according to the procedure for General Method 1, outlined above, starting with 0.40 mmol of 3-[(2-fluoro-4-iodophenyl)amino]isonicotinic acid (intermediate 1) and 0.60 mmol of 3-imidazol-1-yl-propylamine. LC/MS [4.82 min; 466 (M+1)]

Example 21

N-benzyl-3-[(2-fluoro-4-iodophenyl)amino]isonicotinamide

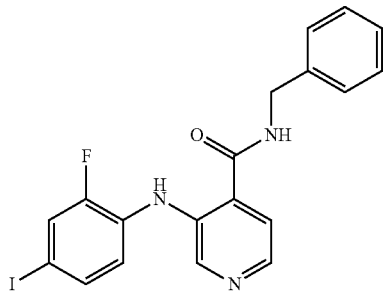 [SMILES: O=C(NCc1ccccc1)c1ccncc1Nc1ccc(I)cc1F]

N-benzyl-3-[(2-fluoro-4-iodophenyl)amino]isonicotinamide was synthesized according to the procedure for General Method 1, outlined above, starting with 0.3 mmol 3-[(2-fluoro-4-iodophenyl)amino]isonicotinic acid (intermediate 1) and 0.45 mmol of benzylamine. LC/MS [7.55 min; 448 (M+1)]

Example 22

3-[(2-chloro-4-iodophenyl)amino]-N-methylisonicotinamide

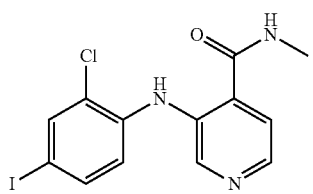 [SMILES: CNC(=O)c1ccncc1Nc1ccc(I)cc1Cl]

3-[(2-chloro-4-iodophenyl)amino]-N-methylisonicotinamide was synthesized according to the procedure for General Method 1, outlined above, starting with 0.32 mmol of 3-[(2-chloro-4-iodophenyl)amino]isonicotinic acid (intermediate 2) and 0.43 mmol of monomethylamine LC/MS [9.23 min; 389 (M+1)]

Example 23

3-[(2-chloro-4-iodophenyl)amino]-N-dimethylisonicotinamide

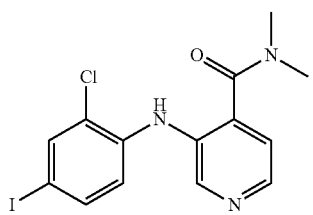 [SMILES: CN(C)C(=O)c1ccncc1Nc1ccc(I)cc1Cl]

3-[(2-chloro-4-iodophenyl)amino]-N-dimethylisonicotinamide was synthesized according to the procedure for General Method 1, outlined above, starting with 0.30 mmol of 3-[(2-chloro-4-iodophenyl)amino]isonicotinic acid (intermediate 2) and 0.40 mmol of dimethylamine LC/MS [8.38 min; 402.7 (M+1)]

Example 24

3-[(2-fluoro-4-iodophenyl)amino]-N-(2-methoxy-ethyl)-N-methyl-isonicotinamide

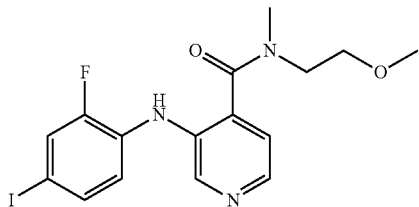 [SMILES: COCCN(C)C(=O)c1ccncc1Nc1ccc(I)cc1F]

3-[(2-fluoro-4-iodophenyl)amino]-N-(2-methoxyethyl)-N-methylisonicotinamide was synthesized according to the procedure for General Method 1, outlined above, starting with 0.42 mmol of 3-[(2-fluoro-4-iodophenyl)amino]isonicotinic acid (intermediate 1) and 0.57 mmol of (2-methoxyethyl)-dimethyl-amine LC/MS [7.84 min; 430 (M+1)]

Example 25

3-[(2-fluoro-4-iodophenyl)amino]-N-morpholin-4-ylisonicotin-amide

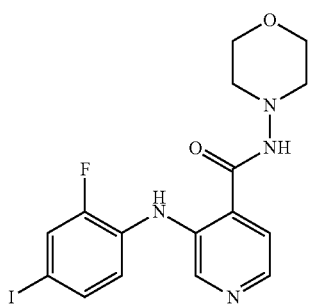 [SMILES: O=C(NN1CCOCC1)c1ccncc1Nc1ccc(I)cc1F]

3-[(2-fluoro-4-iodophenyl)amino]-N-morpholin-4-yl-isonicotinamide was synthesized according to the procedure for General Method 1, outlined above, starting with 0.5 mmol of 3-[(2-fluoro-4-iodophenyl)amino]isonicotinic acid (intermediate 1) and 0.81 mmol of morpholin-4-ylamine LC/MS [8.25 min; 443 (M+1)]

Example 26

3-[(2-fluoro-4-iodophenyl)amino]-N-(2-phenoxy-ethyl)-isonicotinamide

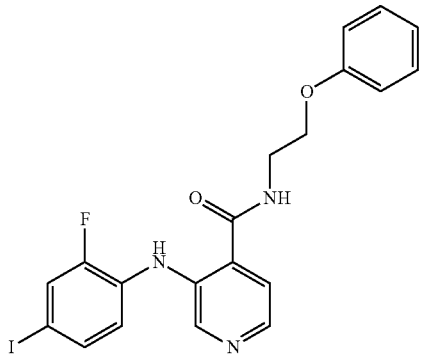 [SMILES: O=C(NCCOc1ccccc1)c1ccncc1Nc1ccc(I)cc1F]

3-[(2-fluoro-4-iodophenyl)amino]-N-(2-phenoxyethyl)isonicotinamide was synthesized according to the procedure for General Method 1, outlined above, starting with 0.32 mmol of 3-[(2-fluoro-4-iodophenyl)amino]isonicotinic acid (intermediate 1) and 0.45 mmol of 2-phenoxyethylamine. LC/MS [10.10 min; 478 (M+1)]

Example 27

3-[(2-fluoro-4-iodophenyl)amino]-N-[2-(2-methoxyphenyl)-ethyl]isonicotinamide

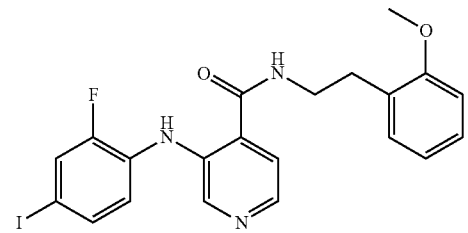 [SMILES: COc1ccccc1CCNC(=O)c1ccncc1Nc1ccc(I)cc1F]

3-[(2-fluoro-4-iodophenyl)amino]-N-[2-(2-methoxyphenyl)ethyl]isonicotinamide was synthesized according to the procedure for General Method 1, outlined above, starting with 0.54 mmol of 3-[(2-fluoro-4-iodophenyl)amino]isonicotinic acid (intermediate 1) and 0.81 mmol of 2-(2-methoxyphenyl)-ethylamine. LC/MS [10.19 min; 492 (M+1)]

Example 28

N'-{3-[(2-fluoro-4-iodophenyl)amino]isonicotinoyl}-1H-indazole-3-carbohydrazide

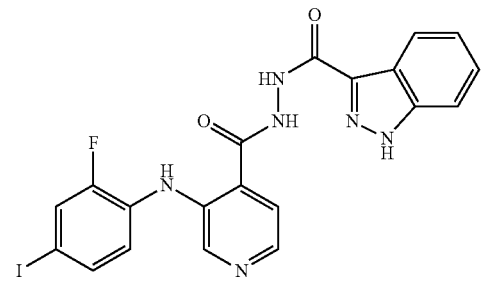 [SMILES: O=C(NNC(=O)c1n[nH]c2ccccc12)c1ccncc1Nc1ccc(I)cc1F]

N'-{3-[(2-fluoro-4-iodophenyl)amino]isonicotinoyl}-1H-indazole-3-carbohydrazide was synthesized according to the procedure for General Method 1, outlined above, starting with 0.32 mmol of 3-[(2-fluoro-4-iodophenyl)amino]isonicotinic acid (intermediate 1) and 0.47 mmol of 1H-indazole-3-carboxylic acid hydrazide. LC/MS [9.14 min; 517 (M+1)]

Example 29

N-[2-(3-chlorophenyl)ethyl]-3-[(2-fluoro-4-iodophenyl)-amino]isonicotinamide

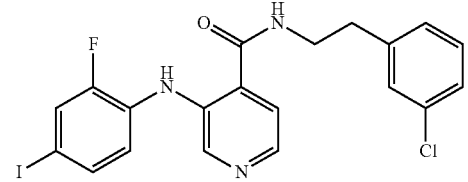 [SMILES: O=C(NCCc1cccc(Cl)c1)c1ccncc1Nc1ccc(I)cc1F]

N-[2-(3-chlorophenyl)ethyl]-3-[(2-fluoro-4-iodophenyl)amino]isonicotinamide was synthesized according to the procedure for General Method 1, outlined above, starting with 0.5 mmol of 3-[(2-fluoro-4-iodophenyl)amino]isonicotinic acid (intermediate 1) and 0.75 mmol of 2-(3-chlorophenyl)ethylamine. LC/MS [10.47 min; 496 (M+1)]

Example 30

3-[(2-fluoro-4-iodophenyl)amino]-N-[3-(2-oxopyrrolidin-1-yl)propyl]isonicotinamide

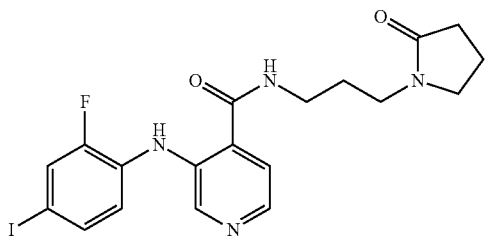 [SMILES: O=C(NCCCN1CCCC1=O)c1ccncc1Nc1ccc(I)cc1F]

3-[(2-fluoro-4-iodophenyl)amino]-N-[3-(2-oxopyrrolidin-1-yl)propyl]isonicotinamide was synthesized according to the procedure for General Method 1, outlined above, starting with 0.6 mmol of 3-[(2-fluoro-4-iodophenyl)amino]isonicotinic acid (intermediate 1) and 0.85 mmol of 1-(3-amino-propyl)-pyrrolidin-2-one LC/MS [8.70 min; 483 (M+1)].

Example 31

2-Chloro-3-(2-fluoro-4-iodo-phenylamino)-isonicotinamide

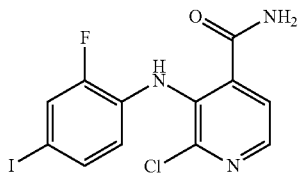 [SMILES: NC(=O)c1ccnc(Cl)c1Nc1ccc(I)cc1F]

2-Chloro-3-(2-fluoro-4-iodo-phenylamino)-isonicotinamide was synthesized according to the procedure for General Method 1, outlined above, starting with 0.2 mmol of 2-Chloro-3-(2-fluoro-4-iodo-phenylamino)-isonicotinic acid and 0.5 mmol of ammonium acetate. LC/MS [8.61 min; 392 (M+1)].

Example 32

3-[(2-fluoro-4-iodophenyl)amino]-N'-phenylisonicotinohydrazide

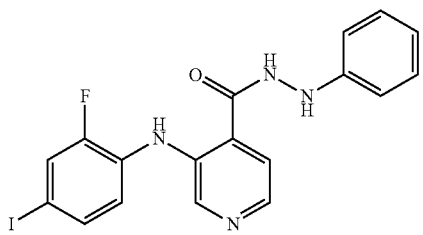

3-[(2-fluoro-4-iodophenyl)amino]-N'-phenylisonicotinohydrazide was synthesized according to the procedure for General Method 1, outlined above, starting with 0.45 mmol of 3-[(2-fluoro-4-iodophenyl)amino]isonicotinic acid (intermediate 1) and 0.7 mmol of phenylhydrazine. LC/MS [9.52 min; 449 (M+1)]

Example 33

3-[(2-fluoro-4-iodophenyl)amino]-N-(2-piperidin-1-ylethyl)-isonicotinamide

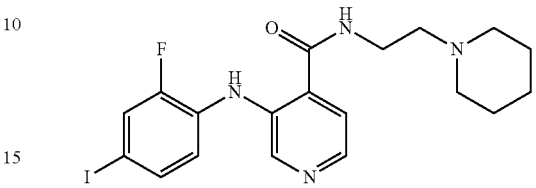

3-[(2-fluoro-4-iodophenyl)amino]-N-(2-piperidin-1-ylethyl)isonicotinamide was synthesized according to the procedure for General Method 1, outlined above, starting with 2.5 mmol of 3-[(2-fluoro-4-iodophenyl)amino]isonicotinic acid (intermediate 1) and 4.0 mmol of 2-piperidin-1-ylethylamine. LC/MS [5.40 min; 469 (M+1)]

Example 34 tert-butyl(1-{3-[(2-fluoro-4-iodophenyl)amino]isonicotinoyl}-piperidin-4-yl)carbamate

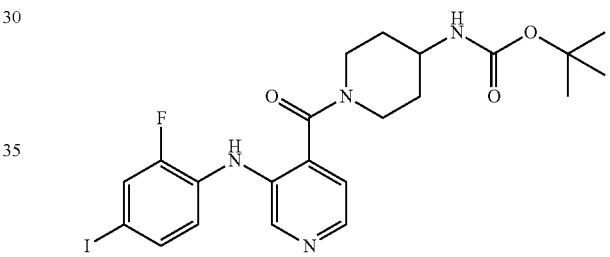

tert-butyl(1-{3-[(2-fluoro-4-iodophenyl)amino]isonicotinoyl}piperidin-4-yl)carbamate was synthesized according to the procedure for General Method 1, outlined above, starting with 2.4 mmol of 3-[(2-fluoro-4-iodophenyl)amino]isonicotinic acid (intermediate 1) and 4.0 mmol of piperidin-4-yl-carbamic acid tert-butyl ester. LC/MS [9.47 min; 541 (M+1)]

Example 35

3-[(2-fluoro-4-iodophenyl)amino]-N-(3-morpholin-4-ylpropyl)-isonicotinamide

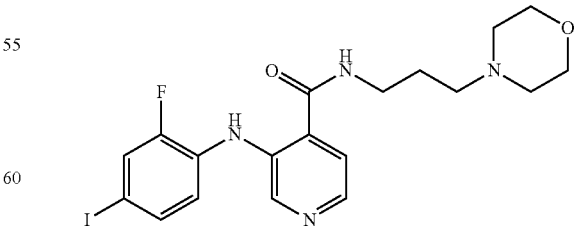

3-[(2-fluoro-4-iodophenyl)amino]-N-(3-morpholin-4-ylpropyl)isonicotinamide was synthesized according to the procedure for General Method 1, outlined above, starting with 1.0 mmol of 3-[(2-fluoro-4-iodophenyl)amino]isonicotinic acid (intermediate 1) and 1.6 mmol of 3-morpholin-4-yl-propylamine. LC/MS [4.66 min; 485 (M+1)]

Example 36

3-(2-Chloro-4-iodo-phenylamino)-N-(5-hydroxy-pentyl)-isonicotinamide

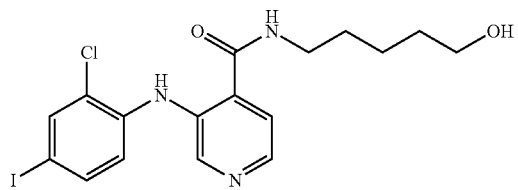 [SMILES: O=C(NCCCCCO)c1ccncc1Nc1ccc(I)cc1Cl]

3-(2-Chloro-4-iodo-phenylamino)-N-(5-hydroxy-pentyl)-isonicotinamide was synthesized according to the procedure for General Method 1, outlined above, starting with 0.30 mmol of 3-[(2-chloro-4-iodophenyl)amino]isonicotinic acid (intermediate 2) and 0.40 mmol of 5-amino-pentan-1-ol. LC/MS [9.33 min; 461 (M+1)]

Example 37

3-[(2-fluoro-4-iodophenyl)amino]-N-(2-hydroxyethylmethyl-isonicotinamide

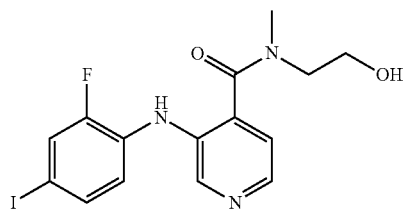 [SMILES: CN(CCO)C(=O)c1ccncc1Nc1ccc(I)cc1F]

3-[(2-fluoro-4-iodophenyl)amino]-N-(2-hydroxyethylmethylisonicotinamide was synthesized according to the procedure for General Method 1, outlined above, starting with 0.4 mmol of 3-[(2-fluoro-4-iodophenyl)amino]isonicotinic acid (intermediate 1) and 0.6 mmol of 2-methylamino-ethanol. LC/MS [6.47 min; 416 (M+1)]

Example 38

2-Chloro-N-{[(4R)-2,2-dimethyl-1,3-dioxolan-4-yl]methoxy}-3-(2-fluoro-4-iodo-phenylamino)-isonicotinamide

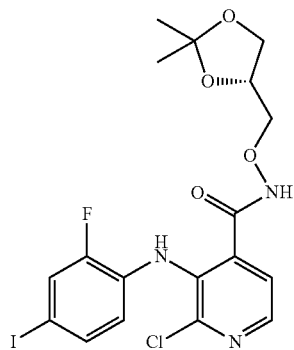 [SMILES: CC1(C)OC[C@H](CONC(=O)c2ccnc(Cl)c2Nc2ccc(I)cc2F)O1]

2-Chloro-N-{[(4R)-2,2-dimethyl-1,3-dioxolan-4-yl]methoxy}-3-(2-fluoro-4-iodo-phenylamino)-isonicotinamide was synthesized according to the procedure for General Method 1, outlined above, starting with 0.2 mmol of 2-chloro-3-(2-fluoro-4-iodo-phenylamino)-isonicotinic acid and 0.3 mmol of O-{[(4R)-2,2-dimethyl-1,3-dioxolan-4-yl]methyl}-hydroxylamine LC/MS [9.19 min; 522 (M+1)].

Example 39

3-[(2-fluoro-4-iodophenyl)amino]-N-(4-hydroxybutyl)-isonicotinamide

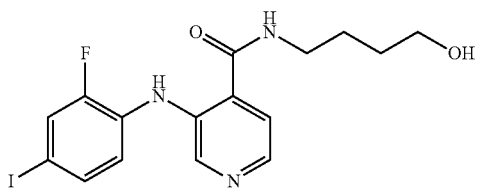 [SMILES: O=C(NCCCCO)c1ccncc1Nc1ccc(I)cc1F]

3-[(2-fluoro-4-iodophenyl)amino]-N-(4-hydroxybutyl)isonicotinamide was synthesized according to the procedure for General Method 1, outlined above, starting with 0.5 mmol of 3-[(2-fluoro-4-iodophenyl)amino]isonicotinic acid (intermediate 1) and 0.63 mmol of 4-hydroxy-butylamine. LC/MS [8.42 min; 430 (M+1)]

Example 40

3-[(2-fluoro-4-iodophenyl)amino]-N-(pyridin-2-ylmethyl)-isonicotinamide

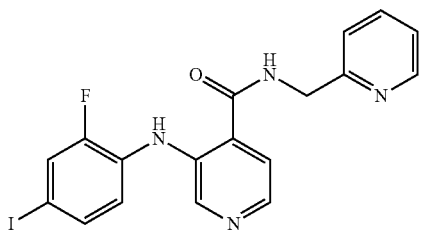 [SMILES: O=C(NCc1ccccn1)c1ccncc1Nc1ccc(I)cc1F]

3-[(2-fluoro-4-iodophenyl)amino]-N-(pyridin-2-ylmethyl)isonicotinamide was synthesized according to the procedure for General Method 1, outlined above, starting with 0.46 mmol of 3-[(2-fluoro-4-iodophenyl)amino]isonicotinic acid (intermediate 1) and 0.78 mmol of pyridine-2-methylamine. LC/MS [8.33 min; 449 (M+1)]

Example 41

3-[(2-fluoro-4-iodophenyl)amino]-N-[(2S)-2-hydroxypropyl]-isonicotinamide

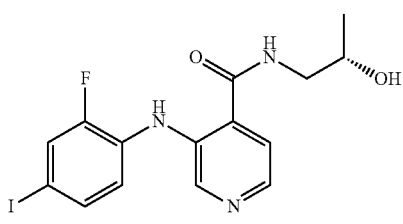 [SMILES: C[C@H](O)CNC(=O)c1ccncc1Nc1ccc(I)cc1F]

3-[(2-fluoro-4-iodophenyl)amino]-N-[(2S)-2-hydroxypropyl]isonicotinamide was synthesized according to the procedure for General Method 1, outlined above, starting with 0.3 mmol of 3-[(2-fluoro-4-iodophenyl)amino]isonicotinic acid (intermediate 1) and 0.4 mmol of 2-(R)-hydroxypropylamine. LC/MS [8.40 min; 416 (M+1)]

Example 42

N-azepan-1-yl-3-[(2-fluoro-4-iodophenyl)amino]isonicotinamide

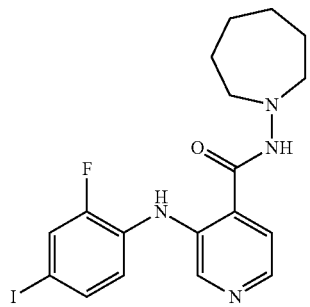 [SMILES: O=C(NN1CCCCCC1)c1ccncc1Nc1ccc(I)cc1F]

N-azepan-1-yl-3-[(2-fluoro-4-iodophenyl)amino]isonicotinamide was synthesized according to the procedure for General Method 1, outlined above, starting with 0.45 mmol of 3-[(2-fluoro-4-iodophenyl)amino]isonicotinic acid (intermediate 1) and 6.2 mmol of azepan-1-ylamine. LC/MS [8.99 min; 455 (M+1)]

Example 43

2-Chloro-N-[(2R)-2,3-dihydroxy-propoxy]-3-(2-fluoro-4-iodo-phenylamino)-isonicotinamide

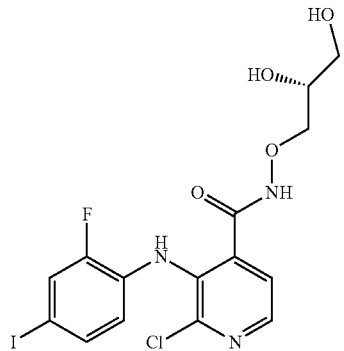 [SMILES: O=C(NOC[C@H](O)CO)c1ccnc(Cl)c1Nc1ccc(I)cc1F]

Deprotection of 2-Chloro-N-{[(4R)-2,2-dimethyl-1,3-dioxolan-4-yl]methoxy}-3-(2-fluoro-4-iodo-phenylamino)-isonicotinamide with 50:50 mixture of TFA/dichloromethane at room temperature for 30 minutes afforded the desired product. Purification by reverse phase LC/MS [7.94 min; 482 (M+1)].

Example 44

4-[(4-aminopiperidin-1-yl)carbonyl]-N-(2-fluoro-4-iodophenyl)pyridin-3-amine hydrochloride

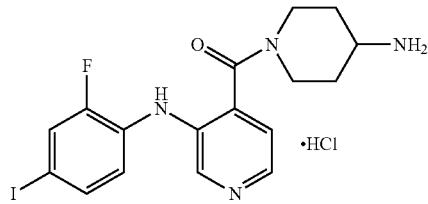 [SMILES: NC1CCN(C(=O)c2ccncc2Nc2ccc(I)cc2F)CC1 ; Cl]

4-[(4-aminopiperidin-1-yl)carbonyl]-N-(2-fluoro-4-iodophenyl)pyridin-3-amine was synthesized from tert-butyl (1-{3-[(2-fluoro-4-iodophenyl)amino]isonicotinoyl}piperidin-4-yl)carbamate (described below) by deprotection of the Boc group with TFA/DCM: 0.33 mmol of tert-butyl(1-{3-[(2-fluoro-4-iodophenyl)amino]isonicotinoyl}piperidin-4-yl)carbamate was dissolved in 4 ml of 50:50 mixture of TFA/dichloromethane. After 2 hours of stirring at room temperature the volatiles were stripped and the residue was re-dissolved in 2 ml of methanol. 1.0N HCl in diethylether was added and the product precipitated. LC/MS [2.01 min; 441 (free base, M+1)]

Example 45 tert-butyl 2-{3-[(2-fluoro-4-iodophenyl)amino]-isonicotinoyl}hydrazine-carboxylate

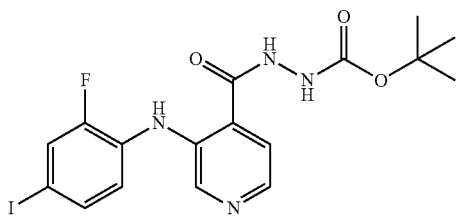 [SMILES: CC(C)(C)OC(=O)NNC(=O)c1ccncc1Nc1ccc(I)cc1F]

tert-butyl 2-{3-[(2-fluoro-4-iodophenyl)amino]isonicotinoyl}hydrazine-carboxylate was synthesized according to the procedure for General Method 1, outlined above, starting with 3 mmol of 3-[(2-fluoro-4-iodophenyl)amino]isonicotinic acid (intermediate 1) and 5 mmol of hydrazinecarboxylic acid tert-butylester. LC/MS [9.37 min; 473 (M+1)]

Example 46

4-[({3-[(2-fluoro-4-iodophenyl)amino]isonicotinoyl}-amino)methyl]benzoic acid

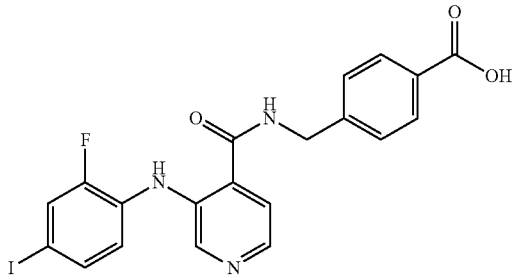 [SMILES: O=C(O)c1ccc(CNC(=O)c2ccncc2Nc2ccc(I)cc2F)cc1]

4-[({3-[(2-fluoro-4-iodophenyl)amino]isonicotinoyl}amino)methyl]benzoic acid was synthesized according to the procedure for General Method 1, outlined above, starting with 0.3 mmol of 3-[(2-fluoro-4-iodophenyl)amino]isonicotinic acid (intermediate 1) and 0.45 mmol of 4-aminomethylbenzoic acid. LC/MS [9.25 min; 492 (M+1)]

Example 47

N-cyclopropyl-3-[(2-fluoro-4-iodophenyl)amino]isonicotinamide

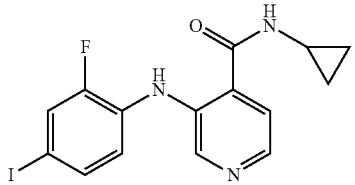 [SMILES: O=C(NC1CC1)c1ccncc1Nc1ccc(I)cc1F]

N-cyclopropyl-3-[(2-fluoro-4-iodophenyl)amino]isonicotinamide was synthesized according to the procedure for General Method 1, outlined above, starting with 0.2 mmol of 3-[(2-fluoro-4-iodophenyl)amino]isonicotinic acid (intermediate 1) and 0.23 mmol of cyclopropylamine. LC/MS [8.78 min; 398 (M+1)]

Example 48

3-[(2-fluoro-4-iodophenyl)amino]-N-[(2R)-2-hydroxypropyl]-isonicotinamide

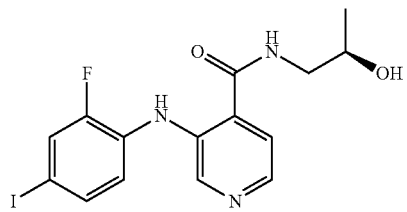 [SMILES: C[C@@H](O)CNC(=O)c1ccncc1Nc1ccc(I)cc1F]

3-[(2-fluoro-4-iodophenyl)amino]-N-[(2R)-2-hydroxypropyl]isonicotinamide was synthesized according to the procedure for General Method 1, outlined above, starting with 2 mmol of 3-[(2-fluoro-4-iodophenyl)amino]isonicotinic acid (intermediate 1) and 3 mmol of 2-(R)-hydroxypropylamine LC/MS [8.33 min; 416 (M+1)]

Example 49

3-[(2-fluoro-4-iodophenyl)amino]-N'-pyridin-2-yl-isonicotino-hydrazide

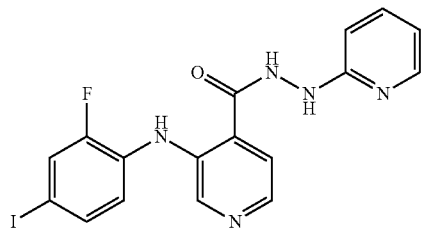 [SMILES: O=C(NNc1ccccn1)c1ccncc1Nc1ccc(I)cc1F]

3-[(2-fluoro-4-iodophenyl)amino]-N'-pyridin-2-ylisonicotinohydrazide was synthesized according to the procedure for General Method 1, outlined above, starting with 0.5 mmol of 3-[(2-fluoro-4-iodophenyl)amino]isonicotinic acid (intermediate 1) and 0.8 mmol of pyridin-2-yl-hydrazine. LC/MS [6.90 min; 450 (M+1)]

Example 50

3-[(2-fluoro-4-iodophenyl)amino]-N'-[4-(trifluoromethyl)pyrimidin-2-yl]isonicotinohydrazide

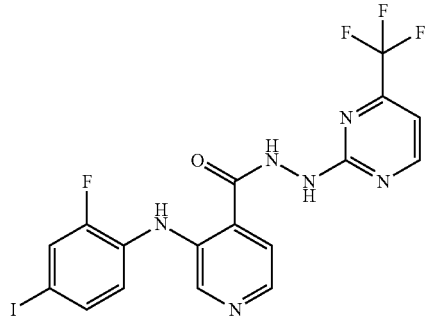 [SMILES: O=C(NNc1nccc(C(F)(F)F)n1)c1ccncc1Nc1ccc(I)cc1F]

3-[(2-fluoro-4-iodophenyl)amino]-N'-[4-(trifluoromethyl)pyrimidin-2-yl]isonicotinohydrazide was synthesized according to the procedure for General Method 1, outlined above, starting with 0.4 mmol of 3-[(2-fluoro-4-iodophenyl)amino]isonicotinic acid (intermediate 1) and 0.6 mmol of 4-trifluoromethyl-pyrimidin-2-yl)-hydrazine. LC/MS [9.38 min; 519 (M+1)]

Example 51

3-[(2-fluoro-4-iodophenyl)amino]isonicotinohydrazide

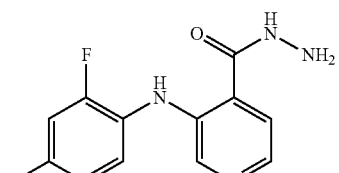

3-[(2-fluoro-4-iodophenyl)amino]isonicotinohydrazide hydrochloride was synthesized from tert-butyl 2-{3-[(2-fluoro-4-iodophenyl)amino]isonicotinoyl}hydrazine-carboxylate (described earlier) by deprotection of the Boc group under acidic conditions (50:50 TFA/DCM). LC/MS [7.11 min; 373 (free base, M+1)]

Example 52

5-[(2-fluoro-4-iodophenyl)amino]-2-(4-methoxyphenyl)isonicotinic acid

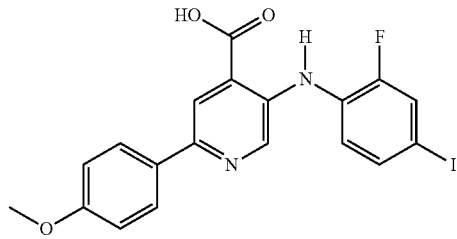 [SMILES: COc1ccc(-c2cc(C(=O)O)c(Nc3ccc(I)cc3F)cn2)cc1]

5-[(2-fluoro-4-iodophenyl)amino]-2-(4-methoxyphenyl)isonicotinic acid was synthesized according to the General method 5, outlined above. First 5-Fluoro-2-(4-methoxyphenyl)pyridine was synthesized starting with 1.0 g (5.68 mmol) of 2-bromo-5-fluoropyridine and p-methoxy phenylmagnesium bromide (13.7 ml, 0.5 M in THF, 6.82 mmol) in the presence of 0.66 g (0.57 mmol) of tetrakis(triphenylphosphine)Pd complex. Yield: 766 mg, 66%. Then 5-fluoro-2-(4-methoxyphenyl)isonicotinic acid was synthesized from 765 mg (3.76 mmol) of 5-fluoro-2-(4-methoxyphenyl)pyridine, butyllithium (1.8 ml, 2.50 M in THF, 4.52 mmol) and dry ice. Yield: 450 mg, 48%. 5-[(2-fluoro-4-iodophenyl)amino]-2-(4-methoxyphenyl)isonicotinic acid was then synthesized with 2.37 mmol of 2-fluoro-4-iodoaniline and by 1.82 mmol of 5-fluoro-2-(4-methoxyphenyl)isonicotinic acid as described in General Method 5. LC/MS. [9.52 min, 465 (M+1)]

Example 53

N-(cyclopropylmethyl)-3-[(2-fluoro-4-iodophenyl)amino]-isonicotinamide

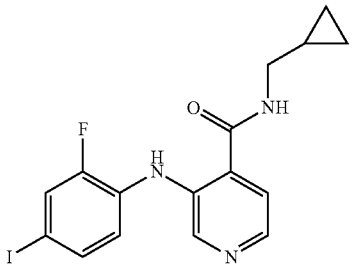 [SMILES: O=C(NCC1CC1)c1ccncc1Nc1ccc(I)cc1F]

N-(cyclopropylmethyl)-3-[(2-fluoro-4-iodophenyl)amino]isonicotinamide was synthesized according to the procedure for General Method 1, outlined above, starting with 0.2 mmol of 3-[(2-fluoro-4-iodophenyl)amino]isonicotinic acid (intermediate 1) and 0.23 mmol of cyclopropylmethylamine. LC/MS [9.79 min; 412 (M+1)]

Example 54

3-(2-Chloro-4-ethynyl-phenylamino)-N-(2,3-dihydroxy-propoxy)-isonicotinamide

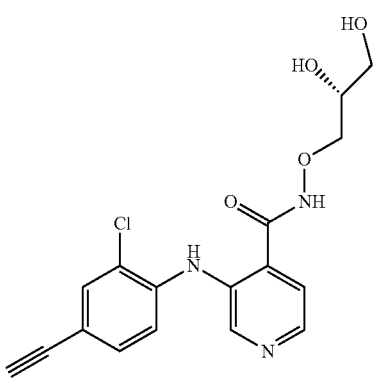 [SMILES: C#Cc1ccc(Nc2cnccc2C(=O)NOC[C@H](O)CO)c(Cl)c1]

0.43 mmol of 3-[(2-chloro-4-iodophenyl)amino]-N-{[(2R)-2,3-dihydroxypropyl]oxy}isonicotinamide (synthesis described above), 0.02 mmol of dichlorobis(triphenylphosphine)palladium(II), and 0.03 mmol of copper (I) iodide were dissolved and DMF and TEA. 0.93 mmol of trimethylsilylacetylene was added to the stirring solution and the resultant orange mixture was vigorously stirred for 18 h at ambient temperature. The solvent was then removed under reduced pressure and the residue was diluted with EtOAc, washed with water (2×) and saturated brine (2×). The organics were dried over Na$_2$SO$_4$, filtered, and then concentrated under reduced pressure to give a brown solid, which was then dissolved in methanol. 3.10 mmol of CsF was added and the mixture was stirred at ambient temperature. After stirring for 16 h, the solution was concentrated, taken up in EtOAc, and then the organic phase was washed with water, brine, dried over Na$_2$SO$_4$, filtered, and concentrated under reduced pressure. The residue was subjected to column chromatography (Flashmaster) on silica gel using EtOAc/MeOH (0-100%) to afford the desired product LC/MS [5.29 min; 362 (M+1)]

Example 55

3-[(2-fluoro-4-iodophenyl)amino]-N'-(3-methoxybenzoyl)-isonicotinohydrazide

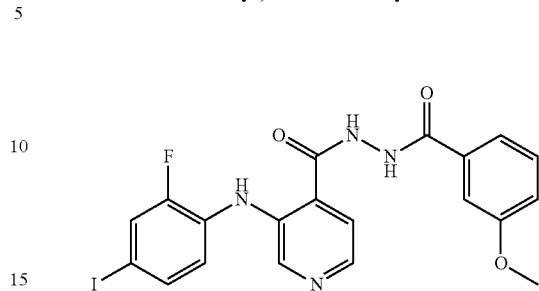

3-[(2-fluoro-4-iodophenyl)amino]-N'-(3-methoxybenzoyl)isonicotinohydrazide was synthesized according to the procedure for General Method 1, outlined above, starting with 0.4 mmol of 3-[(2-fluoro-4-iodophenyl)amino]isonicotinic acid (intermediate 1) and 0.55 mmol of 3-methoxybenzohydrazide. LC/MS [9.23 min; 507 (M+1)]

Example 56

N'-(7-chloroquinolin-4-yl)-3-[(2-fluoro-4-iodophenyl)amino]-isonicotino-hydrazide

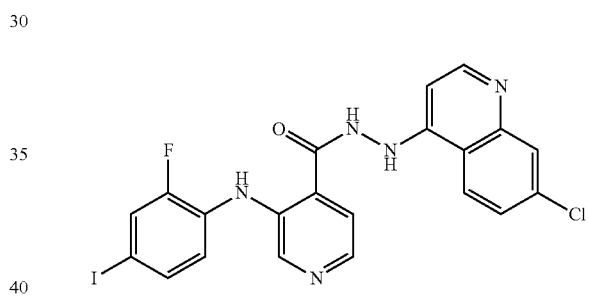

N'-(7-chloroquinolin-4-yl)-3-[(2-fluoro-4-iodophenyl)amino]isonicotino-hydrazide was synthesized according to the procedure for General Method 1, outlined above, starting with 0.33 mmol of 3-[(2-fluoro-4-iodophenyl)amino]isonicotinic acid (intermediate 1) and 0.50 mmol of 7-chloroquinolin-4-yl-hydrazine. LC/MS [7.69 min; 534 (M+1)]

Example 57

2-[4-(dimethylamino)phenyl]-5-[(2-fluoro-4-iodophenyl)amino]-isonicotinic acid

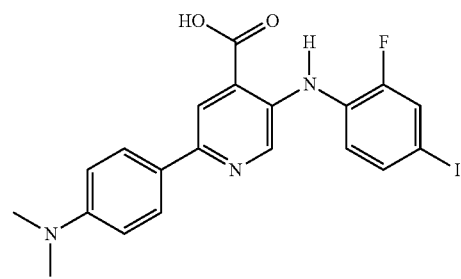 [SMILES: CN(C)c1ccc(-c2cc(C(=O)O)c(Nc3ccc(I)cc3F)cn2)cc1]

2-[4-(dimethylamino)phenyl]-5-[(2-fluoro-4-iodophenyl) amino]isonicotinic acid was synthesized according to the General Method 5, outlined above. First 4-(5-fluoropyridin-2-yl)-N,N-dimethylaniline was synthesized starting with 5.68 mmol of 2-bromo-5-fluoropyridine and 4-(N,N-dimethyl)anilinemagnesium bromide (6.82 mmol) in the presence of 0.66 g (0.57 mmol) of tetrakis(triphenylphosphine)Pd complex. Yield: 650 mg, 59%. Then 2-[4-(dimethylamino) phenyl]-5-fluoroisonicotinic acid was synthesized from 2.66 mmol of 4-(5-fluoropyridin-2-yl)-N,N-dimethylaniline, butyllithium (17.3 mmol) and dry ice. Yield: 460 mg, 66%. 5-[(2-fluoro-4-iodophenyl)amino]-2-(4-methoxyphenyl) isonicotinic acid was then synthesized with 1.25 mmol of 2-fluoro-4-iodoaniline and by 0.96 mmol of 2-[4-(dimethylamino)phenyl]-5-fluoroisonicotinic acid as described in General Method 5. LC/MS: [8.86 min, 478 (M+1)]

Example 58

N-cyclobutyl-3-[(2-fluoro-4-iodophenyl)amino] isonicotinamide

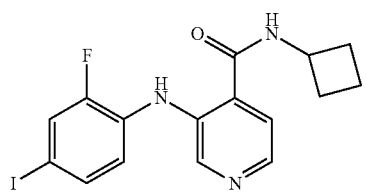 [SMILES: O=C(NC1CCC1)c1ccncc1Nc1ccc(I)cc1F]

N-(cyclobutyl)-3-[(2-fluoro-4-iodophenyl)amino]isonicotinamide was synthesized according to the procedure for General Method 1, outlined above, starting with 0.34 mmol of 3-[(2-fluoro-4-iodophenyl)amino]isonicotinic acid (intermediate 1) and 0.42 mmol of cyclobutylamine. LC/MS [9.86 min; 412 (M+1)]

Example 59

N-(2,3-dihydro-1H-inden-1-yl)-3-[(2-fluoro-4-iodophenyl)amino]-isonicotinamide

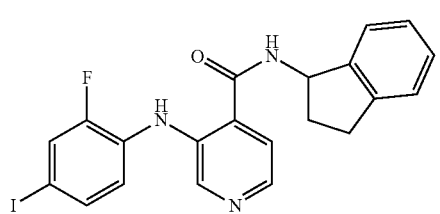 [SMILES: O=C(NC1CCc2ccccc21)c1ccncc1Nc1ccc(I)cc1F]

N-(2,3-dihydro-1H-inden-1-yl)-3-[(2-fluoro-4-iodophenyl)amino]isonicotinamide was synthesized according to the procedure for General Method 1, outlined above, starting with 0.43 mmol of 3-[(2-fluoro-4-iodophenyl)amino]isonicotinic acid (intermediate 1) and 0.57 mmol of indanylamine. LC/MS [10.69 min; 474 (M+1)]

Example 60

N-cyclopentyl-3-[(2-fluoro-4-iodophenyl)amino] isonicotinamide

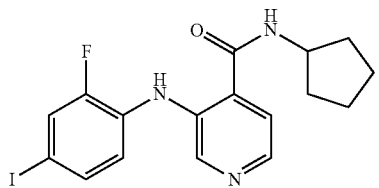 [SMILES: O=C(NC1CCCC1)c1ccncc1Nc1ccc(I)cc1F]

N-cyclopentyl-3-[(2-fluoro-4-iodophenyl)amino]isonicotinamide was synthesized according to the procedure for General Method 1, outlined above, starting with 0.45 mmol of 3-[(2-fluoro-4-iodophenyl)amino]isonicotinic acid (intermediate 1) and 0.57 mmol of cyclopentylamine. LC/MS [9.55 min; 426 (M+1)]

Example 61

N-cyclohexyl-3-[(2-fluoro-4-iodophenyl)amino] isonicotinamide

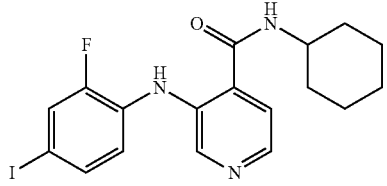 [SMILES: O=C(NC1CCCCC1)c1ccncc1Nc1ccc(I)cc1F]

N-cyclohexyl-3-[(2-fluoro-4-iodophenyl)amino]isonicotinamide was synthesized according to the procedure for General Method 1, outlined above, starting with 0.33 mmol of 3-[(2-fluoro-4-iodophenyl)amino]isonicotinic acid (intermediate 1) and 0.42 mmol of cyclohexylamine. LC/MS [10.52 min; 440 (M+1)]

Example 62

N-(1,2-dimethylpropyl)-3-[(2-fluoro-4-iodophenyl) amino]-isonicotinamide

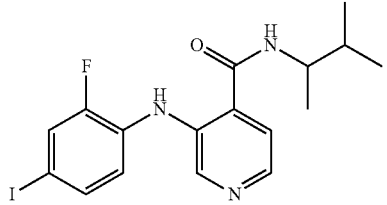 [SMILES: CC(C)C(C)NC(=O)c1ccncc1Nc1ccc(I)cc1F]

N-(1,2-dimethylpropyl)-3-[(2-fluoro-4-iodophenyl) amino]isonicotinamide was synthesized according to the procedure for General Method 1, outlined above, starting with 0.4 mmol of 3-[(2-fluoro-4-iodophenyl)amino]isonicotinic acid (intermediate 1) and 0.6 mmol of 2,3,dimethyl butylamine LC/MS [10.32 min; 428 (M+1)]

Example 63

N-{[(4S)-2,2-dimethyl-1,3-dioxolan-4-yl]methoxy}-3-[(2-fluoro-4-iodophenyl)amino]isonicotinamide

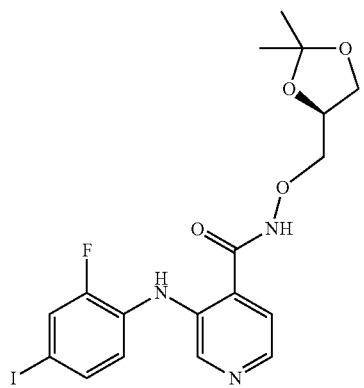 [SMILES: CC1(C)OC[C@@H](CONC(=O)c2ccncc2Nc2ccc(I)cc2F)O1]

N-{[(4S)-2,2-dimethyl-1,3-dioxolan-4-yl]methoxy}-3-[(2-fluoro-4-iodophenyl)amino]isonicotinamide was synthesized as its isomer N-{[(4R)-2,2-dimethyl-1,3-dioxolan-4-yl]methoxy}-3-[(2-fluoro-4-iodophenyl)amino] isonicotinamide LC/MS. [8.94 min; 488 (M+1)]

Example 64

N-(2-Acetylamino-ethyl)-3-(2-chloro-4-iodo-phenylamino)-isonicotinamide

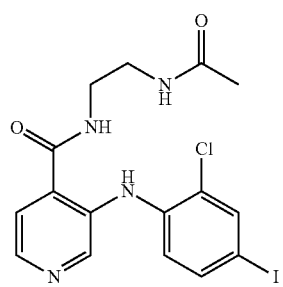 [SMILES: CC(=O)NCCNC(=O)c1ccncc1Nc1ccc(I)cc1Cl]

N-(2-Acetylamino-ethyl)-3-(2-chloro-4-iodo-phenylamino)-isonicotinamide was synthesized according to the procedure for General Method 1, outlined above, starting with 0.32 mmol of 3-[(2-chloro-4-iodophenyl)amino]isonicotinic acid (intermediate 2) and 0.44 mmol N-(2-aminoethyl)-acetamide LC/MS [8.38 min; 4.59 (M+1)]

Example 65

3-(2-Chloro-4-iodo-phenylamino)-pyridine-4-carbonyl]-carbamic acid tert-butyl ester

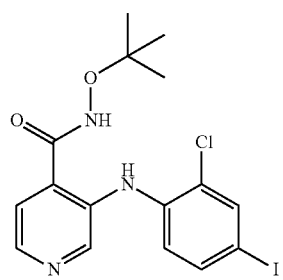 [SMILES: CC(C)(C)ONC(=O)c1ccncc1Nc1ccc(I)cc1Cl]

3-(2-Chloro-4-iodo-phenylamino)-pyridine-4-carbonyl] carbamic acid tert-butyl ester was synthesized according to the procedure for General Method 1, outlined above, starting with 0.6 mmol of 3-[(2-chloro-4-iodophenyl)amino]isonicotinic acid (intermediate 2) and 0.8 mmol of carbamic acid tert-butyl ester. LC/MS [9.69 min; 445.8 (M+1)]

Example 66

3-[(2-fluoro-4-iodophenyl)amino]-N-hydroxyisonicotinamide

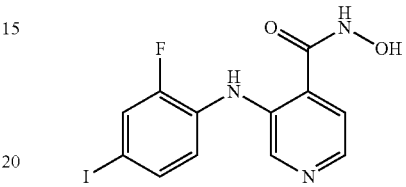

3-[(2-fluoro-4-iodophenyl)amino]-N-hydroxyisonicotinamide was synthesized according to the procedure for General Method 1, outlined above, starting with 0.31 mmol of 3-[(2-fluoro-4-iodophenyl)amino]isonicotinic acid (intermediate 1) and 0.6 mmol of hydroxylamine. LC/MS [7.37 min; 374 (M+1)]

Example 67

3-(4-iodo-phenylamino)-isonicotinamide

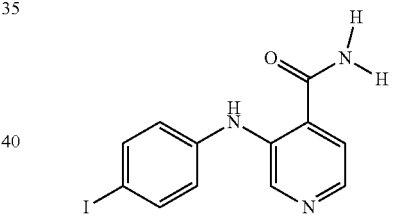

3-(4-iodo-phenylamino)-isonicotinamide was synthesized according to the procedure for General Method 1, outlined above, starting with 0.2 mmol of 3-(4-iodophenyl)amino-isonicotinic acid and 0.4 mmol of ammonium acetate. LC/MS [5.03 min; 340 (M+1)]

Example 68

2-Bromo-5-(2-fluoro-4-iodo-phenylamino)-isonicotinamide

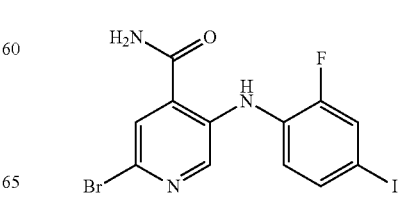

The synthesis of 2-Bromo-5-(2-fluoro-4-iodo-phenylamino)-isonicotinamide was described under General Method 3.

Example 69

2-bromo-N-{[(4R)-2,2-dimethyl-1,3-dioxolan-4-yl]methoxy}-5[(2-fluoro-4-iodophenyl)amino]isonicotinamide

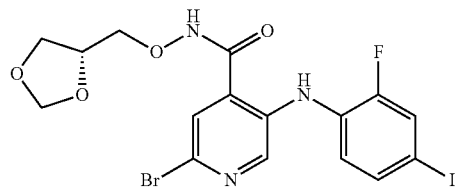 [SMILES: O=C(NOC[C@H]1COCO1)c1cc(Br)ncc1Nc1ccc(I)cc1F]

2-bromo-N-{[(4R)-2,2-dimethyl-1,3-dioxolan-4-yl]methoxy}-5-[(2-fluoro-4-iodophenyl)amino]isonicotinamide was synthesized as described in General Method 3: to a solution of 2-bromo-5-[(2-fluoro-4-iodophenyl)amino]isonicotinic acid (145.0 mg, 0.33 mmol) in DMF (1.5 ml) was added 1,1'-carbonylbis(1H-imidazole) (60 mg, 0.36 mmol). The reaction mixture was stirred at room temperature under argon for 6 hrs. Then, O-[(2,2-dimethyl-1,3-dioxolan-4-yl)methyl]hydroxylamine (125 mg, 0.83 mmol) was added, and stirred overnight. The reaction mixture was poured into water (10 ml). Extracted with EtOAc (3×15 ml), the combined organic layer was washed with brine (2×15 ml), and dried over MgSO₄. The solvent was evaporated, and the residue was purified on silica gel column (Hex:EtOAc=3:1) to obtain 104 mg (55%) of 2-bromo-N-{[(4R)-2,2-dimethyl-1,3-dioxolan-4-yl]methoxy}-5-[(2-fluoro-4-iodophenyl)-amino]isonicotinamide. LC/MS: 10.43 min, 566, 568.

Example 70

2-Bromo-5-(2-fluoro-4-iodo-phenylamine)-N-(3-hydroxy-propyl)-isonicotinamide

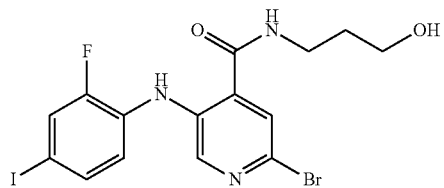 [SMILES: O=C(NCCCO)c1cc(Br)ncc1Nc1ccc(I)cc1F]

2-Bromo-5-(2-fluoro-4-iodo-phenylamino)-N-(3-hydroxy-propyl)-isonicotinamide was synthesized according to General method 3, starting with 145 mg (0.33 mmol) of 2-bromo-5-[(2-fluoro-4-iodophenyl)amino]isonicotinic acid and 62 mg (0.82 mmol) of 3-Amino-propan-1-ol. LC/MS: [9.15 min, 494, 496]

Example 71

2-Bromo-N-(2,4-dihydroxy-butoxy)-5-(2-fluoro-4-iodo-phenylamino)-isonicotinamide

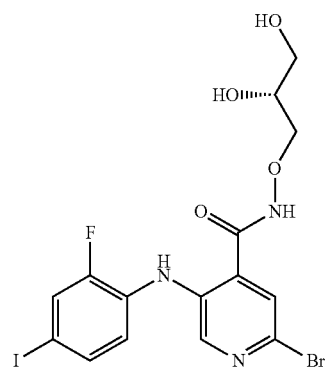 [SMILES: O=C(NOC[C@H](O)CO)c1cc(Br)ncc1Nc1ccc(I)cc1F]

2-Bromo-N-(2,4-dihydroxy-butoxy)-5-(2-fluoro-4-iodo-phenylamino)-isonicotinamide was synthesized as described in General method 3: To a solution of 2-bromo-N-{[(4R)-2,2-dimethyl-1,3-dioxolan-4-yl]methoxy}-5-[(2-fluoro-4-iodophenyl)amino]-isonicotinamide (100.0 mg, 0.18 mmol) in dichloromethane (1 ml) was added trifluoroacetic acid (1 ml) at RT. The reaction mixture was stirred at RT for 30 min, and monitored by TLC (Hex:EtOAc=1:1 and contain TEA). Upon completion, the volatiles were evaporated, and the residue was dissolved in dichloromethane, washed with 5% aq. NaHCO₃ to get a precipitate. The residue was filtered, washed with water, and dried to get 53 mg (56%) of 2-Bromo-N-(2,4-dihydroxy-butoxy)-5-(2-fluoro-4-iodo-phenylamino)-isonicotinamide. LC/MS: [8.76 min, 541 (M+1)]

Example 72

2-Bromo-5-(2-fluoro-4-iodo-phenylamino)-N-(3-imidazol-1-yl-propyl)-isonicotinamide

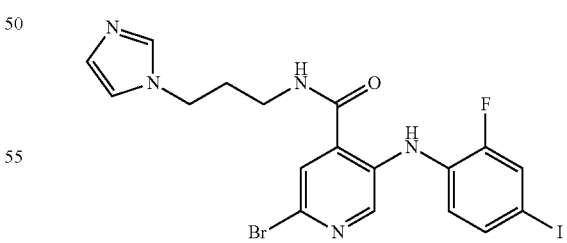

2-Bromo-5-(2-fluoro-4-iodo-phenylamino)-N-(3-imidazol-1-yl-propyl)-isonicotinamide was synthesized according to the General Method 3, starting with 145 mg (0.33 mmol) of 2-bromo-5-[(2-fluoro-4-iodophenyl)amino]isonicotinic acid and 103 mg (0.83 mmol) of 3-Imidazol-1-yl-propylamine. Yield: 55 mg, 30%, LC/MS: [7.31 min, 545 (M+1)]

Example 73

3-(4-iodo-phenylamino)-isonicotinic acid

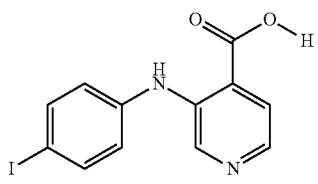 [SMILES: O=C(O)c1ccncc1Nc1ccc(I)cc1]

3-(4-iodo-phenylamino)-isonicotinic acid was synthesized according to the procedure for General Method 1 and as Intermediate 1 by reacting 1.4 mmol of 4-iodoaniline with 2.8 mmol of 2-fluoro-isonicotinic acid LC/MS [6.29 min; 341 (M+1)].

Example 74

2-Bromo-5-(2-fluoro-4-iodo-phenylamino)-N-(2-hydroxy-ethyl)-isonicotinamide

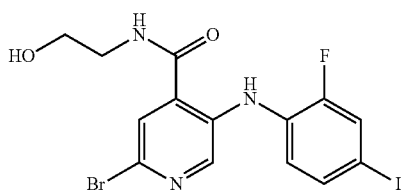 [SMILES: O=C(NCCO)c1cc(Br)ncc1Nc1ccc(I)cc1F]

2-Bromo-5-(2-fluoro-4-iodo-phenylamino)-N-(2-hydroxy-ethyl)-isonicotinamide was synthesized according to General Method 3, starting with 145 mg (0.33 mmol) of 2-bromo-5-[(2-fluoro-4-iodophenyl)amino]isonicotinic acid 51 mg (0.83 mmol) of 2-amino-ethanol. LC/MS: [8.98 min, 480, 482]

Example 75

N-{[(2S)-2,3-dihydroxypropyl]oxy}-3-[(2-fluoro-4-iodophenyl)amino]isonicotin-amide

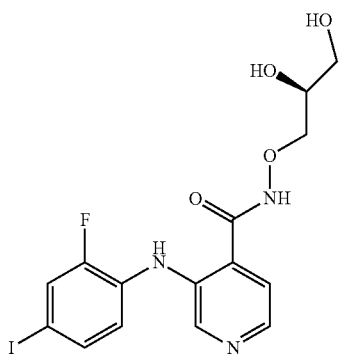 [SMILES: O=C(NOC[C@@H](O)CO)c1ccncc1Nc1ccc(I)cc1F]

N-{[(4S)-2,2-dimethyl-1,3-dioxolan-4-yl]methoxy}-3-[(2-fluoro-4-iodophenyl)amino]isonicotinamide (0.162 g, 0.332 mmol) was suspended in dichloromethane (4 mL) and then treated with trifluoroacetic acid (4 mL). The dark-yellow solution was stirred at room temp for 24 h, concentrated, re-dissolved in methanol (10 mL) and concentrated again. The residue was then placed in ethyl acetate (15 mL) and brine (20 mL) and the pH was adjusted between 6 and 7 with aqueous 2 N NaOH. The layers were separated and the organics were washed with brine (25 mL), concentrated to a yellow oil and placed under high vacuum for 3 h to afford the diol as a yellow semi-solid (0.118 g, 80%). LC/MS [7.11 min; 448 (M+1)]

Example 76

N-ethoxy-3-(4-iodo-phenylamino)-isonicotinamide

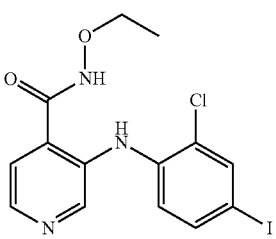 [SMILES: CCONC(=O)c1ccncc1Nc1ccc(I)cc1Cl]

N-ethoxy-3-(4-iodo-phenylamino)-isonicotinamide was synthesized according to the procedure for General Method 1, outlined above, starting with 0.30 mmol of 3-[(2-chloro-4-iodophenyl)amino]isonicotinic acid (intermediate 2) and 0.40 mmol of O-ethyl-hydroxylamine LC/MS [9.14 min; 418 (M+1)]

Example 77

N-allyloxy-3-(2-chloro-4-iodo-phenylamino)-isonicotinamide

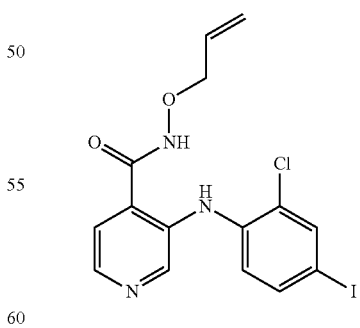

N-allyloxy-3-(2-chloro-4-iodo-phenylamino)-isonicotinamide was synthesized according to the procedure for General Method 1, outlined above, starting with 0.20 mmol of 3-[(2-chloro-4-iodophenyl)amino]isonicotinic acid (intermediate 2) and 0.36 mmol of O-allyl-hydroxylamine. LC/MS [9.30 min; 430 (M+1)]

Example 78

N-isopropoxy-3-(2-chloro-4-iodo-phenylamino)-isonicotinamide

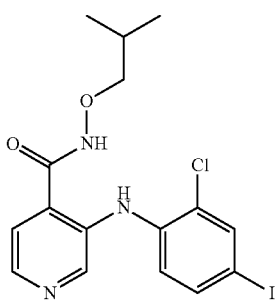 [SMILES: CC(C)CONC(=O)c1ccncc1Nc1ccc(I)cc1Cl]

N-isopropoxy-3-(2-chloro-4-iodo-phenylamino)-isonicotinamide was synthesized according to the procedure for General Method 1, outlined above, starting with 0.30 mmol of 3-[(2-chloro-4-iodophenyl)amino]isonicotinic acid (intermediate 2) and 0.42 mmol of O-Isobutyl-hydroxylamine. LC/MS [10.06 min; 446 (M+1)]

Example 79

N-(3-chloropropyl)-3-[(2-fluoro-4-iodophenyl)-amino]isonicotinamide

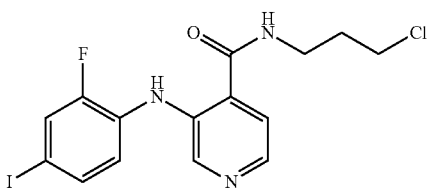 [SMILES: O=C(NCCCCl)c1ccncc1Nc1ccc(I)cc1F]

N-(3-chloropropyl)-3-[(2-fluoro-4-iodophenyl)amino]isonicotinamide was synthesized according to the procedure for General Method 1, outlined above, starting with 1 mmol of 3-[(2-fluoro-4-iodophenyl)amino]isonicotinic acid (intermediate 1) and 1.3 mmol of 3-chloropropylamine. LC/MS [9.24 min; 434 (M+1)]

Example 80

N-methoxy-3-(2-chloro-4-iodo-phenylamino)-isonicotinamide

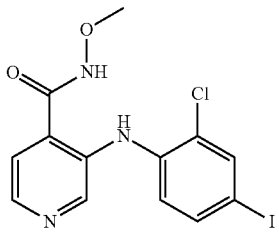 [SMILES: CONC(=O)c1ccncc1Nc1ccc(I)cc1Cl]

N-methoxy-3-(2-chloro-4-iodo-phenylamino)-isonicotinamide was synthesized according to the procedure for General Method 1, outlined above, starting with 0.30 mmol of 3-[(2-chloro-4-iodophenyl)amino]isonicotinic acid (intermediate 2) and 0.42 mmol of O-methyl-hydroxylamine. LC/MS [8.75 min; 404 (M+1)]

Example 81

N-Benzyloxy-3-(2-chloro-4-iodo-phenylamino)-isonicotinamide

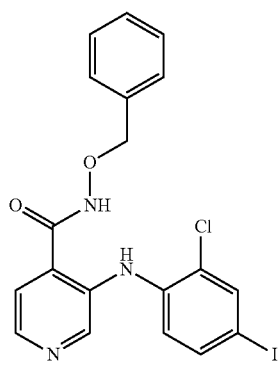 [SMILES: O=C(NOCc1ccccc1)c1ccncc1Nc1ccc(I)cc1Cl]

N-Benzyloxy-3-(2-chloro-4-iodo-phenylamino)-isonicotinamide was synthesized according to the procedure for General Method 1, outlined above, starting with 0.25 mmol of 3-[(2-chloro-4-iodophenyl)amino]isonicotinic acid (intermediate 2) and 0.36 mmol of O-methyl-hydroxylamine. LC/MS [10.01 min; 480 (M+1)]

Example 82

N-bicyclo[2.2.1]hept-2-yl-3-[(2-fluoro-4-iodophenyl)amino]-isonicotinamide

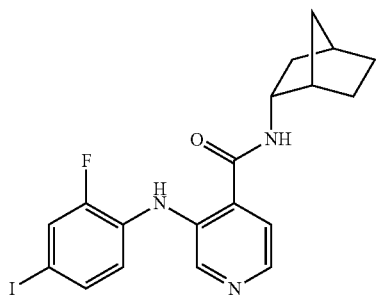 [SMILES: O=C(NC1CC2CCC1C2)c1ccncc1Nc1ccc(I)cc1F]

N-bicyclo[2.2.1]hept-2-yl-3-[(2-fluoro-4-iodophenyl)amino]isonicotinamide was synthesized according to the procedure for General Method 1, outlined above, starting with 0.31 mmol of 3-[(2-fluoro-4-iodophenyl)amino]isonicotinic acid (intermediate 1) and 0.45 mmol of bicyclo[2.2.1]hept-2-ylamine. LC/MS [10.01 min; 452 (M+1)]

Example 83

3-[(2-fluoro-4-iodophenyl)amino]-N-(2-hydroxyphenoxypropyl)-isonicotinamide

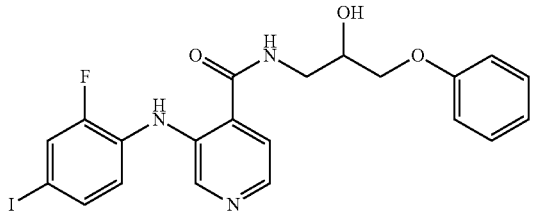 [SMILES: O=C(NCC(O)COc1ccccc1)c1ccncc1Nc1ccc(I)cc1F]

3-[(2-fluoro-4-iodophenyl)amino]-N-(2-hydroxyphenoxypropyl)isonicotinamide was synthesized according to the procedure for General Method 1, outlined above, starting with 0.34 mmol of 3-[(2-fluoro-4-iodophenyl)amino]isonicotinic acid (intermediate 1) and 0.45 mmol of 2-hydroxyphenoxypropylamine. LC/MS [9.53 min; 508 (M+1)]

Example 84

3-[(2-fluoro-4-iodophenyl)amino]-N-(tetrahydro-2H-pyran-2-yloxy)-isonicotin-amide

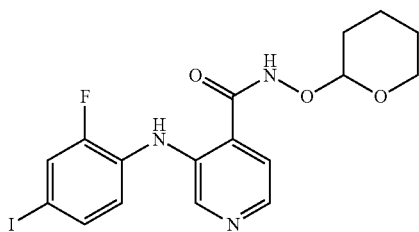 [SMILES: O=C(NOC1CCCCO1)c1ccncc1Nc1ccc(I)cc1F]

3-[(2-fluoro-4-iodophenyl)amino]-N-(tetrahydro-2H-pyran-2-yloxy)isonicotin-amide was synthesized according to the procedure for General Method 1, outlined above, starting with 0.4 mmol of 3-[(2-fluoro-4-iodophenyl)amino]isonicotinic acid (intermediate 1) and 0.52 mmol of O-(tetrahydropyran-2-yl)-hydroxylamine. LC/MS [9.07 min; 458 (M+1)]

Example 85

3-[(2-fluoro-4-iodophenyl)amino]-N-[2-(4-methylphenyl)-ethyl]isonicotinamide

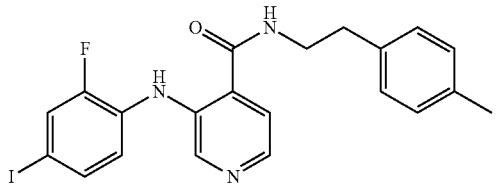 [SMILES: Cc1ccc(CCNC(=O)c2ccncc2Nc2ccc(I)cc2F)cc1]

3-[(2-fluoro-4-iodophenyl)amino]-N-[2-(4-methylphenyl)ethyl]isonicotinamide was synthesized according to the procedure for General Method 1, outlined above, starting with 0.54 mmol of 3-[(2-fluoro-4-iodophenyl)amino]isonicotinic acid (intermediate 1) and 0.62 mmol of 2-(4-methylphenyl)ethylamine. LC/MS [10.25 min; 476 (M+1)]

Example 86

N-(1-{3-[(2-fluoro-4-iodophenyl)amino]isonicotinoyl}piperidin-4-yl)-2-(4-methylphenyl)acetamide

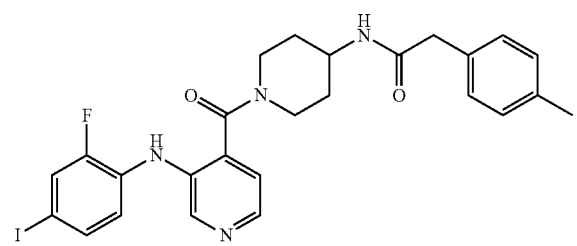 [SMILES: Cc1ccc(CC(=O)NC2CCN(C(=O)c3ccncc3Nc3ccc(I)cc3F)CC2)cc1]

A mixture of p-tolyl acetic acid (0.027 g, 0.180 mmol) and CDI (0.036 g, 0.222 mmol) in dry DMSO (2 mL) was heated to 50° C. for 2 h prior to addition of 4-[(4-aminopiperidin-1-yl)carbonyl]-N-(2-fluoro-4-iodophenyl)pyridin-3-amine hydrochloride (described above) (0.052 g, 0.109 mmol). The contents were then stirred at room temp. After 6 h, HPLC indicated near-complete reaction. The contents were poured into water (30 mL) and extracted with ethyl acetate (30 mL). The organics were washed with brine (2×30 mL), dried over sodium sulfate and concentrated to a yellow oil. The oil was further dried under high vacuum for 2 h at 40° C. to provide the desired product as a yellow semi-solid (0.068 g, 0.119 mmol, 66%). LC/MS [8.92 min; 573 (M+1)]

Example 87

2-Bromo-5-(2-fluoro-4-iodo-phenylamino)-N-(2-methoxy-ethyl)-isonicotinamide

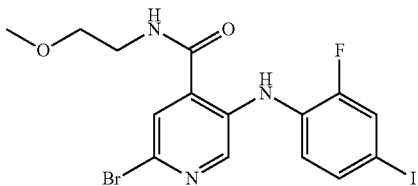 [SMILES: COCCNC(=O)c1cc(Br)ncc1Nc1ccc(I)cc1F]

2-Bromo-5-(2-fluoro-4-iodo-phenylamino)-N-(2-methoxy-ethyl)-isonicotinamide was synthesized according to the General method 3, starting with 145 mg (0.33 mmol) of 2-bromo-5-[(2-fluoro-4-iodophenyl)amino]isonicotinic acid and 51 mg (0.83 mmol) of 2-amino-ethanol. Yield: 88 mg, 55%, LC/MS: [9.55 min, m/z: 495 (M+1)]

Example 88

2-Bromo-5-(2-fluoro-4-iodo-phenylamino)-N-(2-morpholin-4-yl-ethyl)-isonicotinamide

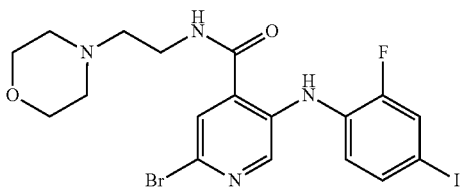 [SMILES: O=C(NCCN1CCOCC1)c1cc(Br)ncc1Nc1ccc(I)cc1F]

2-Bromo-5-(2-fluoro-4-iodo-phenylamino)-N-(2-morpholin-4-yl-ethyl)-isonicotinamide was synthesized according to the General Method 3 starting with 145 mg (0.33 mmol) of 2-bromo-5-[(2-fluoro-4-iodophenyl)amino]isonicotinic acid and 108 mg (0.83 mmol) of 2-morpholin-4-yl-ethylamine. Yield: 95 mg, 52%. LC/MS: [7.08 min, 550, 552 (M+1)]

Example 89

N-(2,2-Dimethyl-[1,3]dioxolan-4-ylmethoxy)-3-(2-fluoro-4-iodo-phenylamino)-1-oxy-isonicotinamide

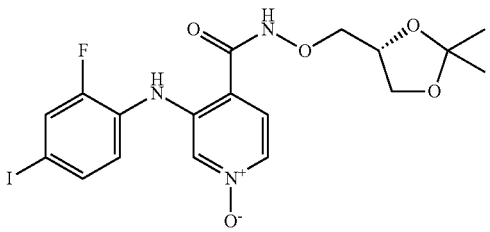 [SMILES: CC1(C)OC[C@H](CONC(=O)c2cc[n+]([O-])cc2Nc2ccc(I)cc2F)O1]

N-(2,2-Dimethyl-[1,3]dioxolan-4-ylmethoxy)-3-(2-fluoro-4-iodo-phenylamino)-1-oxy-isonicotinamide was synthesized as described in General Method 2: to a solution of 3-(2-Fluoro-4-iodo-phenylamino)-1-oxy-isonicotinic acid (110 mg, 0.29 mmol) in DMF (1.2 ml) was added 1,1'-carbonylbis(1H-imidazole) (52.45 mg, 0.32 mmol). The reaction mixture was stirred at RT under argon for 6 hrs. Then, O-[(2,2-dimethyl-1,3-dioxolan-4-yl)methyl]hydroxylamine (109 mg, 0.74 mmol) was added, and the mixture stirred overnight. Then, it was poured into water (10 ml), extracted with EtOAc (3×15 ml), and the combined organic layers were washed with brine (2×15 ml), and dried over MgSO$_4$. The solvent was evaporated, and the residue was purified on silica gel column to obtain 75 mg (51%) of N-(2,2-Dimethyl-[1,3]dioxolan-4-ylmethoxy)-3-(2-fluoro-4-iodo-phenylamino)-1-oxy-isonicotinamide. LC/MS: [8.54 min, 504 (M+1)]

Example 90

3-[(2-fluoro-4-iodophenyl)amino]-N'-(3-methylphenyl)isonicotino-hydrazide

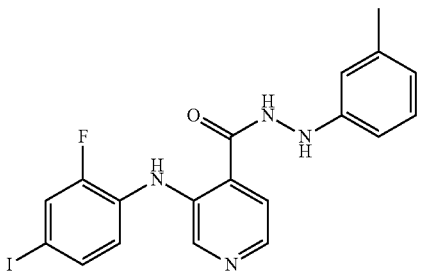 [SMILES: Cc1cccc(NNC(=O)c2ccncc2Nc2ccc(I)cc2F)c1]

3-[(2-fluoro-4-iodophenyl)amino]-N'-(3-methylphenyl)isonicotinohydrazide: was synthesized according to the procedure for General Method 1, outlined above, starting with 0.44 mmol of 3-[(2-fluoro-4-iodophenyl)amino]isonicotinic acid (intermediate 1) and 0.63 mmol of 3-methyl-phenylhydrazine. LC/MS [6.05 min; 463 (M+1)]

Example 91

N-(benzyloxy)-3-[(2-fluoro-4-iodophenyl)amino]isonicotinamide

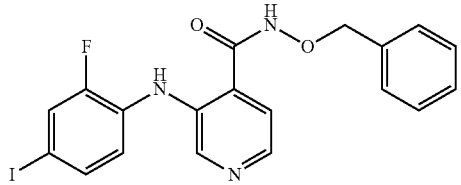 [SMILES: O=C(NOCc1ccccc1)c1ccncc1Nc1ccc(I)cc1F]

N-(benzyloxy)-3-[(2-fluoro-4-iodophenyl)amino]isonicotinamide was synthesized according to the procedure for General Method 1, outlined above, starting with 0.5 mmol of 3-[(2-fluoro-4-iodophenyl)amino]isonicotinic acid (intermediate 1) and 0.72 mmol of O-benzyl-hydroxylamine. LC/MS [9.50 min; 464 (M+1)]

Example 92

[({3-[(2-fluoro-4-iodophenyl)amino]isonicotinoyl}amino)oxy]acetic acid

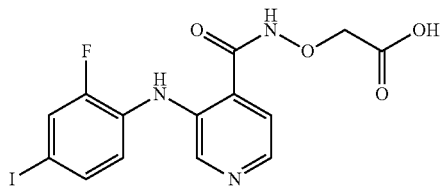 [SMILES: O=C(O)CONC(=O)c1ccncc1Nc1ccc(I)cc1F]

[({3-[(2-fluoro-4-iodophenyl)amino]isonicotinoyl}amino)oxy]acetic acid was synthesized according to the procedure for General Method 1, outlined above, starting with 0.3 mmol of 3-[(2-fluoro-4-iodophenyl)amino]isonicotinic acid (intermediate 1) and 0.51 mmol of aminoxy-acetic acid. LC/MS [5.21 min; 432 (M+1)]

Example 93

N-(2,4-difluorobenzyl)-3-[(2-fluoro-4-iodophenyl)amino]-isonicotinamide

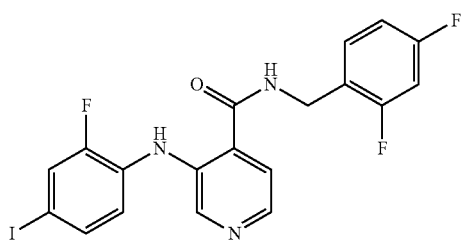 [SMILES: O=C(NCc1ccc(F)cc1F)c1ccncc1Nc1ccc(I)cc1F]

N-(2,4-difluorobenzyl)-3-[(2-fluoro-4-iodophenyl)amino]isonicotinamide was synthesized according to the procedure for General Method 1, outlined above, starting with 0.33 mmol of 3-[(2-fluoro-4-iodophenyl)amino]isonicotinic acid (intermediate 1) and 0.49 mmol of 2,4-difluorobenzylamine. LC/MS [6.28 min; 484 (M+1)]

Example 94

3-[(2-fluoro-4-iodophenyl)amino]-N-(3-iodobenzyl)isonicotin-amide

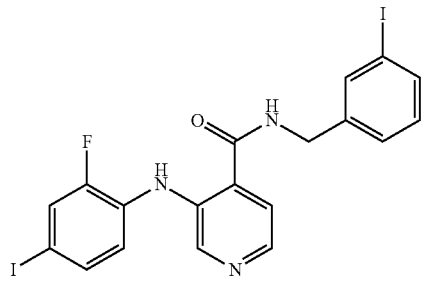 [SMILES: O=C(NCc1cccc(I)c1)c1ccncc1Nc1ccc(I)cc1F]

3-[(2-fluoro-4-iodophenyl)amino]-N-(3-iodobenzyl)isonicotinamide was synthesized according to the procedure for General Method 1, outlined above, starting with 0.23 mmol of 3-[(2-fluoro-4-iodophenyl)amino]isonicotinic acid (intermediate 1) and 0.43 mmol of 3-iodobenzylamine. LC/MS [6.37 min; 574 (M+1)]

Example 95

3-(2-Fluoro-4-iodo-phenylamino)-2-methyl-isonicotinic acid

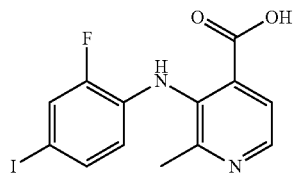 [SMILES: Cc1nccc(C(=O)O)c1Nc1ccc(I)cc1F]

3-(2-Fluoro-4-iodo-phenylamino)-2-methyl-isonicotinic acid was synthesized according to the procedure for General Method 1 and as Intermediate 1 by reacting 2 mmol of 2-fluoro-4-iodoaniline with 3.4 mmol of 2-fluoro-3-methyl-isonicotinic acid LC/MS [4.63 min; 373 (M+1)].

Example 96

N-{[(2R)-2,3-dihydroxypropyl]oxy}-3-(4-iodophenylamino)-isonicotinamide

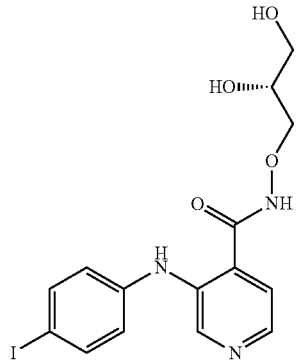 [SMILES: O=C(NOC[C@H](O)CO)c1ccncc1Nc1ccc(I)cc1]

N-{[(2R)-2,3-dihydroxypropyl]oxy}-3-(4-iodophenylamino)-isonicotinamide 3-(4-iodo-phenylamino)-isonicotinamide was synthesized in the same manner as N-{[(2R)-2,3-dihydroxypropyl]oxy}-3-[(2-fluoro-4-iodophenyl)amino]isonicotinamide (described above). LC/MS [7.17 min; 430 (M+1)]

Example 97

3-(2-Fluoro-4-iodo-phenylamino)-1-oxy-isonicotinamide

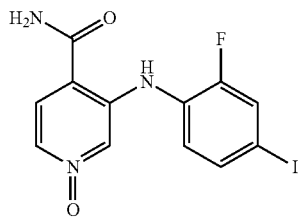 [SMILES: NC(=O)c1cc[n+]([O-])cc1Nc1ccc(I)cc1F]

The synthesis of 3-(2-Fluoro-4-iodo-phenylamino)-1-oxy-isonicotinamide was described under General Method 2.

Example 98

N-(2,2-diethoxyethyl)-3-[(2-fluoro-4-iodophenyl)amino]-isonicotinamide

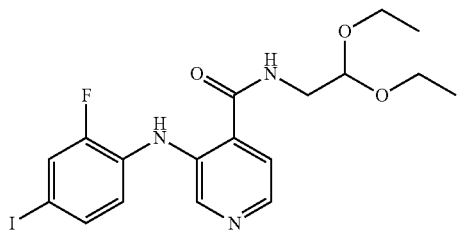 [SMILES: CCOC(CNC(=O)c1ccncc1Nc1ccc(I)cc1F)OCC]

N-(2,2-diethoxyethyl)-3-[(2-fluoro-4-iodophenyl)amino]isonicotinamide was synthesized according to the procedure for General Method 1, outlined above, starting with 0.33 mmol of 3-[(2-fluoro-4-iodophenyl)amino]isonicotinic acid (intermediate 1) and 0.5 mmol of 2,2-diethoxy-ethylamine. LC/MS [5.51 min; 474 (M+1)]

Example 99

3-[(2-fluoro-4-iodophenyl)amino]-N'-(4-methylphenyl)isonicotino-hydrazide

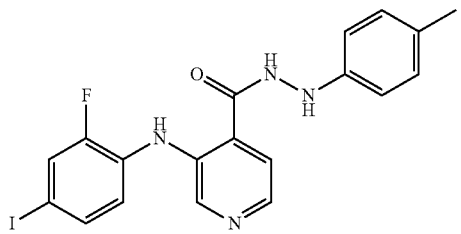 [SMILES: Cc1ccc(NNC(=O)c2ccncc2Nc2ccc(I)cc2F)cc1]

3-[(2-fluoro-4-iodophenyl)amino]-N'-(4-methylphenyl)isonicotinohydrazide was synthesized according to the procedure for General Method 1, outlined above, starting with 0.4 mmol of 3-[(2-fluoro-4-iodophenyl)amino]isonicotinic acid (intermediate 1) and 0.6 mmol of 4-methyl-phenylhydrazine. LC/MS [5.07 min; 463 (M+1)]

Example 100

3-(2-Fluoro-4-iodo-phenylamino)-2-methyl-isonicotinamide

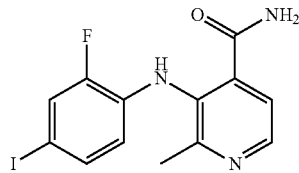 [SMILES: Cc1nccc(C(N)=O)c1Nc1ccc(I)cc1F]

3-(2-Fluoro-4-iodo-phenylamino)-2-methyl-isonicotinamide was synthesized according to the procedure for General Method 1, outlined above, starting with 0.2 mmol of 3-[(2-fluoro-4-iodophenyl)amino]-2-methyl-isonicotinic acid and 0.4 mmol of ammonium acetate. LC/MS [1.85 min; 372 (M+1)].

Example 101

N'-[3,5-bis(trifluoromethyl)phenyl]-3-[(2-fluoroiodophenyl)amino]-isonicotino-hydrazide

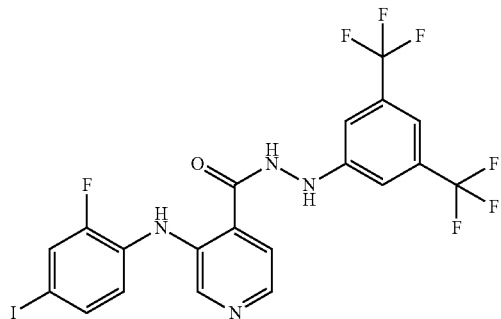 [SMILES: O=C(NNc1cc(C(F)(F)F)cc(C(F)(F)F)c1)c1ccncc1Nc1ccc(I)cc1F]

N'-[3,5-bis(trifluoromethyl)phenyl]-3-[(2-fluoroiodophenyl)amino]isonicotino-hydrazide was synthesized according to the procedure for General Method 1, outlined above, starting with 0.37 mmol of 3-[(2-fluoro-4-iodophenyl)amino]isonicotinic acid (intermediate 1) and 0.53 mmol of 3,5-ditrifluoromethylbenzylhydrazine. LC/MS [6.47 min; 585 (M+1)]

Example 102

4-[2-({3-[(2-fluoro-4-iodophenyl)amino]isonicotinoyl}-amino)ethyl]benzoic acid

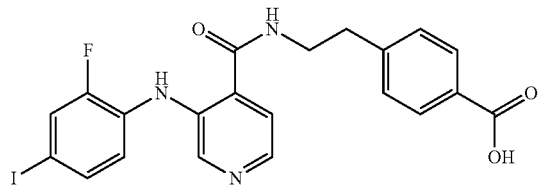 [SMILES: O=C(O)c1ccc(CCNC(=O)c2ccncc2Nc2ccc(I)cc2F)cc1]

4-[2-({3-[(2-fluoro-4-iodophenyl)amino]isonicotinoyl}amino)ethyl]benzoic acid was synthesized according to the procedure for General Method 1, outlined above, starting with 0.66 mmol of 3-[(2-fluoro-4-iodophenyl)amino]isonicotinic acid (intermediate 1) and 0.83 mmol of 4(2-ethylamine)benzoic acid. LC/MS [6.10 min; 506 (M+1)]

Example 103

3-[(2-fluoro-4-iodophenyl)amino]-N-[(pentafluorobenzyl)oxy]-isonicotinamide

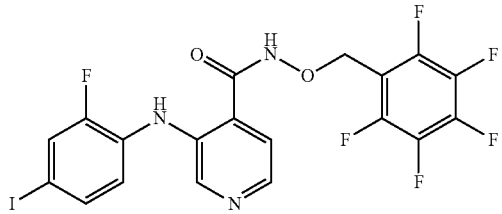 [SMILES: O=C(NOCc1c(F)c(F)c(F)c(F)c1F)c1ccncc1Nc1ccc(I)cc1F]

3-[(2-fluoro-4-iodophenyl)amino]-N-[(pentafluorobenzyl)oxy]isonicotinamide was synthesized according to the procedure for General Method 1, outlined above, starting with 0.32 mmol of 3-[(2-fluoro-4-iodophenyl)amino]isonicotinic acid (intermediate 1) and 0.43 mmol of O-pentafluorophenylmethyl-hydroxylamine. LC/MS [6.50 min; 554 (M+1)]

Example 104

3-[(2-fluoro-4-iodophenyl)amino]-N-(3-methoxyphenyl)-isonicotinamide

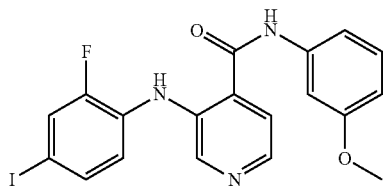 [SMILES: COc1cccc(NC(=O)c2ccncc2Nc2ccc(I)cc2F)c1]

3-[(2-fluoro-4-iodophenyl)amino]-N-(3-methoxyphenyl)isonicotinamide was synthesized according to the procedure for General Method 1, outlined above, starting with 0.31 mmol of 3-[(2-fluoro-4-iodophenyl)amino]isonicotinic acid (intermediate 1) and 0.46 mmol of 3-methoxyaniline. LC/MS [6.40 min; 464 (M+1)]

Example 105

3-[(2-fluoro-4-iodophenyl)amino]-N-[3-fluoro-5-(trifluoromethyl)-benzyl]isonicotinamide

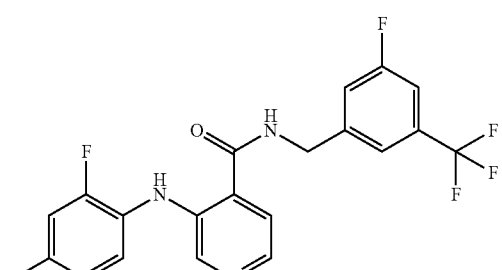

3-[(2-fluoro-4-iodophenyl)amino]-N-[3-fluoro-5-(trifluoromethyl)benzyl]isonicotinamide was synthesized according to the procedure for General Method 1, outlined above, starting with 0.25 mmol of 3-[(2-fluoro-4-iodophenyl)amino]isonicotinic acid (intermediate 1) and 0.37 mmol of 3-fluoro-5-trifluoromethyl-benzylamine. LC/MS [6.51 min; 534 (M+1)]

Example 106

3-[(2-fluoro-4-iodophenyl)amino]-N-(3-hydroxybenzyl)-isonicotinamide

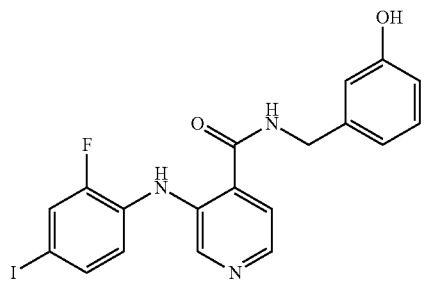 [SMILES: O=C(NCc1cccc(O)c1)c1ccncc1Nc1ccc(I)cc1F]

3-[(2-fluoro-4-iodophenyl)amino]-N-(3-hydroxybenzyl) isonicotinamide was synthesized according to the procedure for General Method 1, outlined above, starting with 0.22 mmol of 3-[(2-fluoro-4-iodophenyl)amino]isonicotinic acid (intermediate 1) and 0.35 mmol of 3-hydroxybenzylamine. LC/MS [6.01 min; 464 (M+1)]

Example 107

N-(4,4-diethoxybutyl)-3-[(2-fluoro-4-iodophenyl)amino]-isonicotinamide

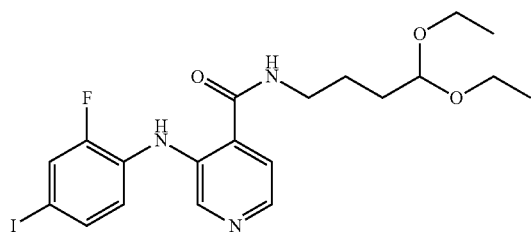 [SMILES: CCOC(CCCNC(=O)c1ccncc1Nc1ccc(I)cc1F)OCC]

N-(2,2-diethoxybutyl)-3-[(2-fluoro-4-iodophenyl)amino] isonicotinamide was synthesized according to the procedure for General Method 1, outlined above, starting with 0.30 mmol of 3-[(2-fluoro-4-iodophenyl)amino]isonicotinic acid (intermediate 1) and 0.45 mmol of 2,2-dibutyloxy-ethylamine. LC/MS [6.33 min; 502 (M+1)]

Example 108

N-(4-Fluoro-benzyl)-3-(2-fluoro-4-iodo-phenylamino)-iso-nicotinamide

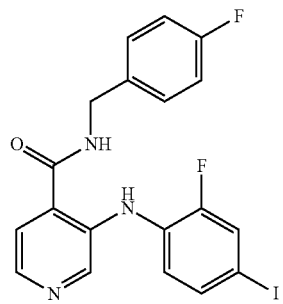 [SMILES: O=C(NCc1ccc(F)cc1)c1ccncc1Nc1ccc(I)cc1F]

N-(4-Fluoro-benzyl)-3-(2-fluoro-4-iodo-phenylamino)-isonicotinamide was synthesized according to the procedure for General Method 1, outlined above, starting with 0.25 mmol of 3-[(2-fluoro-4-iodophenyl)amino]isonicotinic acid (intermediate 1) and 0.33 mmol of 4-fluoro-benzylamine. LC/MS [6.99 min; 466 (M+1)]

Example 109

3-(2-Fluoro-4-iodo-phenylamino)-N-(2,2,2-trifluoro-ethyl)-isonicotinamide

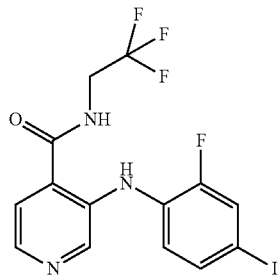 [SMILES: O=C(NCC(F)(F)F)c1ccncc1Nc1ccc(I)cc1F]

3-(2-Fluoro-4-iodo-phenylamino)-N-(2,2,2-trifluoro-ethyl)-isonicotinamide was synthesized according to the procedure for General Method 1, outlined above, starting with 0.30 mmol of 3-[(2-fluoro-4-iodophenyl)amino]isonicotinic acid (intermediate 1) and 0.45 mmol of 2,2,2-trifluoro-ethylamine. LC/MS [6.73 min; 440 (M+1)]

Example 110

3-(2-Fluoro-4-iodo-phenylamino)-N-(1-hydroxymethyl-cyclo-pentyl)-isonicotinamide

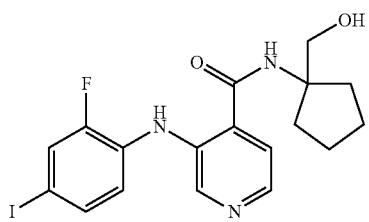 [SMILES: O=C(NC1(CO)CCCC1)c1ccncc1Nc1ccc(I)cc1F]

3-(2-Fluoro-4-iodo-phenylamino)-N-(1-hydroxymethyl-cyclopentyl)-isonicotinamide was synthesized according to the procedure for General Method 1, outlined above, starting with 0.25 mmol of 3-[(2-fluoro-4-iodophenyl)amino]isonicotinic acid (intermediate 1) and 0.42 mmol of. 1-aminocyclopentyl)-methanol. LC/MS [6.04 min; 456 (M+1)].

Example 111

5-[(2-fluoro-4-iodophenyl)amino]-2-methylisonicotinic acid

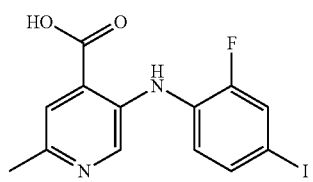 [SMILES: Cc1cc(C(=O)O)c(Nc2ccc(I)cc2F)cn1]

The synthesis of 5-[(2-fluoro-4-iodophenyl)amino]-2-methylisonicotinic acid is described under General Method 4.

Example 112

N-(1-(S)-Carbamoyl-2-hydroxy-ethyl)-3-(2-fluoro-4-iodo-phenylamino)-isonicotinamide

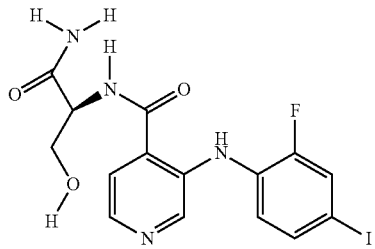 [SMILES: NC(=O)[C@H](CO)NC(=O)c1ccncc1Nc1ccc(I)cc1F]

N-(1-(S)-Carbamoyl-2-hydroxy-ethyl)-3-(2-fluoro-4-iodo-phenylamino)-isonicotinamide was synthesized according to the procedure for General Method 1, outlined above, starting with 0.30 mmol of 3-[(2-fluoro-4-iodophenyl)amino]isonicotinic acid (intermediate 1) and 0.45 mmol of L-serinamide. LC/MS [5.09 min; 445 (M+1)]

Example 113

3-(2-Fluoro-4-iodo-phenylamino)-N-(trans-2-hydroxy-cyclohexyl)-isonicotinamide

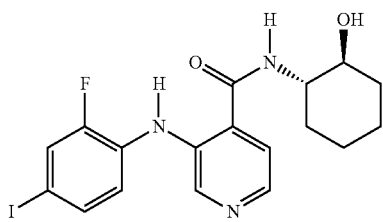 [SMILES: O=C(N[C@H]1CCCC[C@@H]1O)c1ccncc1Nc1ccc(I)cc1F]

3-(2-Fluoro-4-iodo-phenylamino)-N-(trans-2-hydroxycyclohexyl)-isonicotinamide was synthesized according to the procedure for General Method 1, outlined above, starting with 0.27 mmol of 3-[(2-fluoro-4-iodophenyl)amino]isonicotinic acid (intermediate 1) and 0.40 mmol of trans-2-aminocyclohexanol. LC/MS [6.40 (10 min) min; 640 (M+1)]

Example 114

N-(1,1-Bis-hydroxymethyl-propyl)-3-(2-fluoro-4-iodo-phenyl-amino)-isonicotin-amide

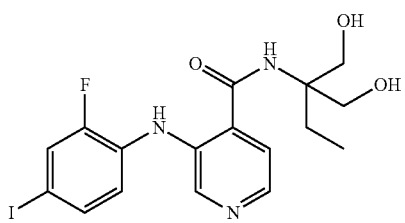 [SMILES: CCC(CO)(CO)NC(=O)c1ccncc1Nc1ccc(I)cc1F]

N-(1,1-Bis-hydroxymethyl-propyl)-3-(2-fluoro-4-iodo-phenylamino)-isonicotinamide was synthesized according to the procedure for General Method 1, outlined above, starting with 0.33 mmol of 3-[(2-fluoro-4-iodophenyl)amino]isonicotinic acid (intermediate 1) and 0.47 mmol of 2-amino-2-ethyl-propane-1,3-diol. LC/MS [5.93 min; 460 (M+1)]

Example 115

N-(2,3-dihydroxy-propyl)-3-(2-fluoro-4-iodo-phenylamino)-isonicotinamide

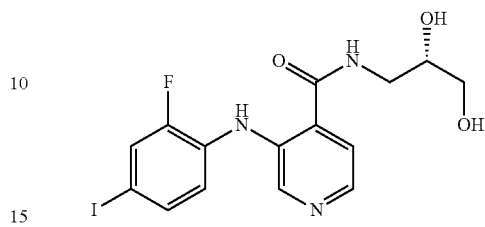

N-(2,3-dihydroxy-propyl)-3-(2-fluoro-4-iodo-phenylamino)-isonicotinamide was synthesized according to the procedure for General Method 1, outlined above, starting with 0.56 mmol of 3-[(2-fluoro-4-iodophenyl)amino]isonicotinic acid (intermediate 1) and 0.84 mmol of 2-amino-2-ethyl-propane-1,3-diol. LC/MS [5.41 min; 432 (M+1)]

Example 116

3-(2-Fluoro-4-iodo-phenylamino)-N-(3-piperazin-1-yl-propyl)-isonicotinamide

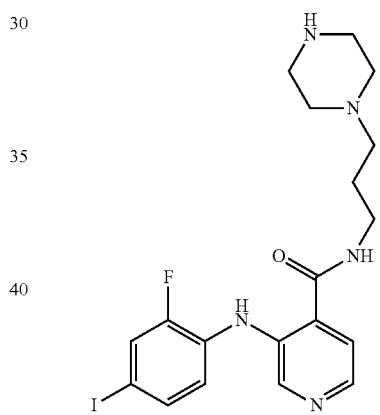

3-(2-Fluoro-4-iodo-phenylamino)-N-(3-piperazin-1-yl-propyl)-isonicotinamide was synthesized according to the procedure for General Method 1, outlined above, starting with 0.32 mmol of 3-[(2-fluoro-4-iodophenyl)amino]isonicotinic acid (intermediate 1) and 0.47 mmol of. 2-piperazin-1-yl-ethylamine. LC/MS [5.02 min; 484 (M+1)].

Example 117

2-Chloro-3-(2-fluoro-4-iodo-phenylamino)-isonicotinic acid

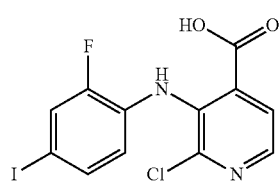 [SMILES: O=C(O)c1ccnc(Cl)c1Nc1ccc(I)cc1F]

2-Chloro-3-(2-fluoro-4-iodo-phenylamino)-isonicotinic acid was synthesized as outlined in General Method 1 and according to the procedure for the synthesis of intermediate 1 by reacting 4 mmol of 2-methyl-4-iodoaniline with 6 mmol 2-fluoro-3-chloro-isonicotinic acid. LC/MS [10.25 min; 390.9 (M−1)-ESI-].

Example 118

3-(4-Methoxy-phenylamino)-isonicotinic acid

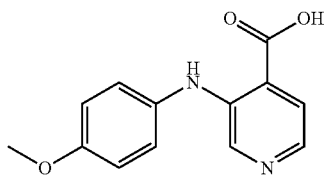 [SMILES: COc1ccc(Nc2cnccc2C(=O)O)cc1]

3-Fluoro-isonicotinic acid (50 mg, 0.354 mmol) and p-anisidine (44 mg, 0.354 mmol) was added to 2 ml dry THF and the mixture was cooled to −78° C. LiHMDS (1 M in THF, 1.24 ml) was added and the mixture was allowed to warm to room temperature over night. Hydrochloric acid (1 M in methanol, 5 ml) was added and the volatiles were removed in vacuo. The crude material was purified by preparative RP chromatography to give 11 mg (45 µmol; 13% yield) of pure desired product. LC-MS (method V): rt=1.82 min; m/z [M+H]+ 245.

Example 119

3-(4-Trifluoromethylsulfanyl-phenylamino)-isonicotinic acid

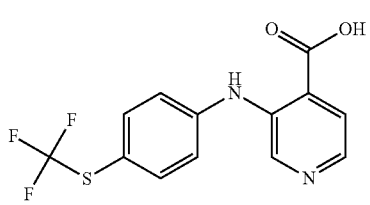 [SMILES: O=C(O)c1ccncc1Nc1ccc(SC(F)(F)F)cc1]

3-Fluoro-isonicotinic acid (50 mg, 0.354 mmol) and 4-(trifluoromethylthio)aniline (68.5 mg, 0.354 mmol) was added to 2 ml dry THF and the mixture was cooled to −78° C. LiHMDS (1 M in THF, 1.24 ml) was added and the mixture was allowed to warm to room temperature over night. Hydrochloric acid (1 M in methanol, 5 ml) was added and the volatiles were removed in vacuo. The crude material was purified by preparative HPLC to give 11.4 mg (45 µmol; 10% yield) of pure desired product. LC-MS (method V): rt=3.09 min, m/z [M+H]+ 315.

Example 120

3-(4-Trifluoromethoxy-phenylamino)-isonicotinic acid

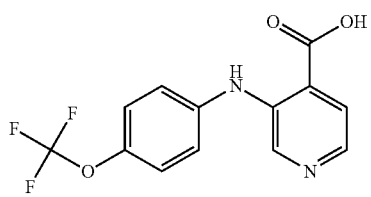 [SMILES: O=C(O)c1ccncc1Nc1ccc(OC(F)(F)F)cc1]

3-Fluoro-isonicotinic acid (50 mg, 0.354 mmol) and 4-(trifluoromethoxy)aniline (62.8 mg, 0.354 mmol) was added to 2 ml dry THF and the mixture was cooled to −78° C. LiHMDS (1 M in THF, 1.24 ml) was added and the mixture was allowed to warm to room temperature over night. Hydrochloric acid (1 M in methanol, 5 ml) was added and the volatiles were removed in vacuo. The crude material was purified by preparative HPLC to give 9.5 mg (32 µmol; 9% yield) of pure desired product. LC-MS (method V): rt=2.69 min; m/z [M+H]+ 299.

Example 121

3-[(4-Bromo-2-fluorophenyl)amino]-N-ethoxyisonicotinamide

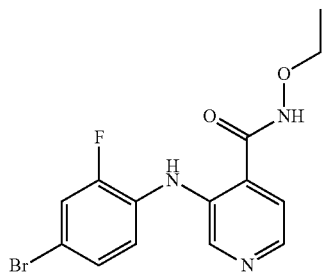 [SMILES: CCONC(=O)c1ccncc1Nc1ccc(Br)cc1F]

Step 1: Synthesis of 3-[(4-Bromo-2-fluoro)amino]isonicotinic acid.

3-Fluoro-isonicotinic acid (1 g, 7.09 mmol) and 4-bromo-2-fluoroaniline (1.35 g, 7.09 mmol) was added to 10 ml of dry THF and the mixture was cooled to −78° C. LiHMDS (1 M in THF, 24.8 ml) was added and the mixture was allowed to warm to room temperature over night. Solid ammonium hydrochloride (2 g) was added and after 1 h the mixture was filtered and the volatiles were removed in vacuo. The crude material was purified by flash-chromatography using C2-modified silica and a gradient of 0-12% methanol in DCM as eluent to give 1.21 g (3.89 mmol; 55% yield) of pure desired carboxylic acid product.

Step 2: 3-[(4-Bromo-2-fluoro)amino]isonicotinic acid from step 1 (300 mg, 0.964 mmol) was dissolved in 6 ml dry DMF followed by the addition of DIPEA (1.16 mmol, 2080, PyBOP (1.16 mmol, 602 mg) and O-ethylhydroxylamine hydrochloride (1.93 mmol, 188 mg). The mixture was stirred at ambient temperature over night and the volatiles were removed in vacuo. The crude material was purified by flash chromatography using silica gel and a gradient of 0-5% methanol in DCM as eluent to give 822 mg of a mixture of the desired product and PyBop-derived phosphoramide byproduct. A 215 mg sample thereof was further purified by preparative RP-HPLC to give 23.3 mg (65.5 mmol) of the pure title compound. LC-MS (method III): rt=6.46 min; m/z [M+H]+ 354/356

Example 122

3-[(4-Iodo-2-fluorophenyl)amino]-N-ethoxyisonicotinamide

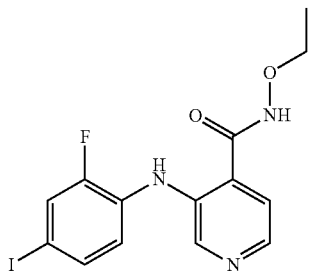 [SMILES: CCONC(=O)c1ccncc1Nc1ccc(I)cc1F]

Step 1: Synthesis of 3-[(4-iodo-2-fluoro)amino]isonicotinic acid.

3-Fluoro-isonicotinic acid (1 g, 7.09 mmol) and 4-iodo-2-fluoroaniline (1.68 g, 7.09 mmol) was added to 10 ml of dry THF and the mixture was cooled to −78° C. LiHMDS (1 M in THF, 24.8 ml) was added and the mixture was allowed to warm to room temperature over night. Solid ammonium hydrochloride (2 g) was added and after 1 h the mixture was filtered and the volatiles were removed in vacuo. The crude material was purified by flash-chromatography using C2-modified silica and a gradient of 0-12% methanol in DCM as eluent to give 932 mg (2.32 mmol; 33% yield) of pure desired carboxylic acid product.

Step 2: 3-[(4-Iodo-2-fluoro)amino]isonicotinic acid from step 1 (200 mg, 0.559 mmol) was dissolved in 4 ml dry DMF followed by the addition of DIPEA (0.671 mmol, 121 µl), PyBOP (0.371 mmol, 350 mg) and O-ethylhydroxylamine hydrochloride (1.12 mmol, 110 mg). The mixture was stirred at ambient temperature over night and the volatiles were removed in vacuo. The crude material was purified by preparative RP-HPLC to give 113 mg (282 mmol; 50% yield) of the pure title compound. LC-MS (method III): rt=7.03 min; m/z [M+H]+ 402.

Example 123

N-[3-(4-Iodo-2-methyl-phenylamino)-pyridine-4-carbonyl]-methanesulfonamide

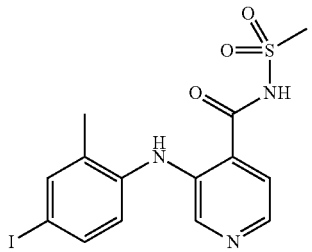 [SMILES: Cc1cc(I)ccc1Nc1cnccc1C(=O)NS(C)(=O)=O]

3-[(4-Iodo-2-methylphenyl)amino]isonicotinic acid (example 3) (50 mg, 0.141 mmol) was dissolved in 4 ml dry THF followed by the addition of 1,1'-carbonyldiimidazole (CDI) (0.311 mmol, 50 mg), methanesulfonamide (0.169 mmol, 16.1 mg) and DBU (0.169 mmol, 26 mg). The mixture was stirred for 16 h at 40° C. and the volatiles were removed in vacuo. The crude material was purified by preparative HPLC to give 20.3 mg (47 µmol; 33% yield) of pure desired product. LC-MS (method III): rt=2.74 min; m/z [M+H]+ 432.

Example 124

N—((S)-2,3-Dihydroxy-propoxy)-3-(4-iodo-2-methyl-phenylamino)-isonicotinamide

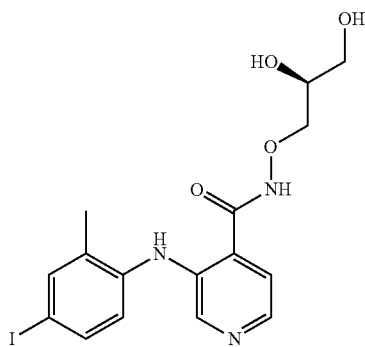 [SMILES: Cc1cc(I)ccc1Nc1cnccc1C(=O)NOC[C@@H](O)CO]

The title compound was synthesized by the procedure as described for Example 119 using O—(S)-2,2-dimethyl-[1,3]dioxolan-4-ylmethyl) -hydroxylamine as a building block. LC-MS (method III): rt=3.22 min; m/z [M+H]+ 444.

Example 125

3-(4-Bromo-2-fluoro-phenylamino)-2-chloro-isonicotinic acid

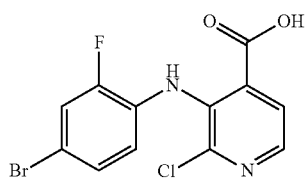 [SMILES: O=C(O)c1ccnc(Cl)c1Nc1ccc(Br)cc1F]

2-Chloro-3-fluoro-isonicotinic acid (200 mg, 1.14 mmol) and 4-bromo-2-fluoroaniline (217 mg, 1.14 mmol) were added to 5 ml of dry THF and the mixture was cooled to −78° C. LiHMDS (1 M in THF, 4.0 ml) was added and the mixture was allowed to warm to room temperature over night. Solid ammonium hydrochloride (1 g) was added and after 1 h the mixture was filtered and the volatiles were removed in vacuo. The crude material was purified by flash-chromatography using a gradient of 0-12% methanol (containing 0.5% formic acid) in DCM as eluent to give 213 mg (0.617 mmol; 54% yield) of pure desired carboxylic acid product. LC-MS (method III): rt=4.42 min; m/z [M+H]+ 386/388.

Example 126

5-[3-(4-Bromo-2-fluoro-phenylamino)-pyridin-4-yl]-3H-[1,3,4]oxadiazol-2-one

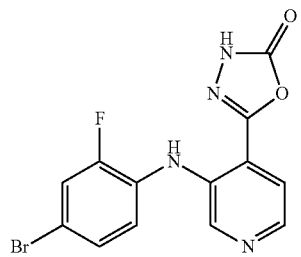 [SMILES: O=c1[nH]nc(-c2ccncc2Nc2ccc(Br)cc2F)o1]

Step 1: Synthesis of 3-(4-Bromo-2-fluoro-phenylamino)-isonicotinic acid hydrazide.

3-(4-Bromo-2-fluoro-phenylamino)-isonicotinic acid (synthesis: see example 121 step 1) (1.5 g, 4.82 mmol) was dissolved in dry DMF (30 ml), N-t-butoxycarbonylhydrazide (1.27 g, 9.64 mmol), ByBOP (3.26 g, 6.27 mmol) and DIPEA (2.52 ml, 14.5 mmol) were added and the mixture was stirred at 60° C. for 14 h. The volatiles were evaporated, the residue was redissolved in ethyl acetate and washed consecutively with saturated NaHCO$_3$, water and brine and dried over sodium sulfate. The volatiles were evaporated and the crude material was purified by flash-chromatography using a gradient of 0-10% methanol in DCM as eluent. The Boc-protected hydrazide was treated with 4N HCl in dioxane (40 ml) at ambient temperature for 14 h and the volatiles were removed under reduced pressure to give 1.51 g (4.66 mmol) of the crude hydrazide.

Step 2: The material derived from step 1 was dissolved in DMF, DIPEA (1.14 ml, 6.52 mmol) and 1,1"-carbonyldiimidazole (CDI, 945 mg, 5.83 mmol) were added and the mixture was stirred at room temperature for 14 h. The volatiles were evaporated and the crude material was purified by flash-chromatography using a gradient of 30-80% ethyl acetate in cyclohexane to give 888 mg (2.53 mmol, 52% yield, 2 steps) of the title compound. LC-MS (method V): rt=3.27 min; m/z [M+H]+ 351/353.

Example 127

2-{5-[3-(4-Bromo-2-fluoro-phenylamino)-pyridin-4-yl]-[1,3,4]oxadiazol-2-ylamino}-ethanol

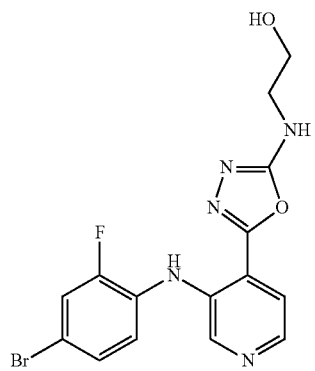 [SMILES: OCCNc1nnc(-c2ccncc2Nc2ccc(Br)cc2F)o1]

Step 1: 5-[3-(4-Bromo-2-fluoro-phenylamino)-pyridin-4-yl]-3H-[1,3,4]oxadiazol-2-one (example 19, 100 mg, 0.277 mmol) was dissolved in ethanol (4 ml), ethanolamine (85 mg, 1.38 mmol) was added and the mixture was stirred for 20 min at 160° C. in a microwave oven. The volatiles were removed to give the crude compound, which was used in the next step.

Step 2: Dry dichloromethane (10 ml) was added to the product derived from step 1, triphenylphosphine (113 mg, 0.429 mmol), triethylamine (58 µl, 0.416 mmol) and carbon tetrachloride (107 µl, 1.11 mmol) were added. The mixture was heated at 100° C. for 10 min in a microwave oven, the volatiles were removed and the crude material was purified by preparative HPLC to give 43 mg (40% yield) of the title compound. LC-MS (method III): rt=4.92 min; m/z [M+H]+ 394/396.

Example 128

N-{5-[3-(4-Bromo-2-fluoro-phenylamino)-pyridin-4-yl]-[1,3,4]oxadiazol-2-yl}-N'-methyl-ethane-1,2-diamine

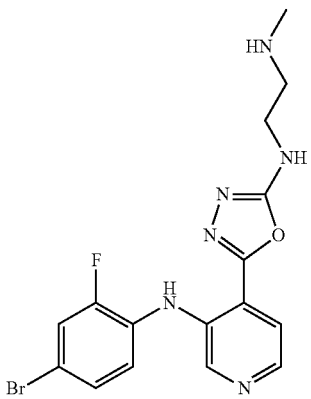 [SMILES: CNCCNc1nnc(-c2ccncc2Nc2ccc(Br)cc2F)o1]

Step 1: 5-[3-(4-Bromo-2-fluoro-phenylamino)-pyridin-4-yl]-3H-[1,3,4]oxadiazol-2-one (example 19, 100 mg, 0.277 mmol) was dissolved in ethanol (3 ml), N-(2-aminoethyl)-N-methylcarbamic acid t-butylester (96 mg, 0.554 mmol) was added and the mixture was stirred for 20 min at 150° C. in a microwave oven. The volatiles were removed to give the crude compound, which was used in the next step.

Step 2: Dry dichloromethane (5 ml) was added to the product derived from step 1 followed by triphenylphosphine (113 mg, 0.429 mmol), triethylamine (58 µl, 0.416 mmol) and carbon tetrachloride (107 µl, 1.11 mmol). The mixture was heated at 100° C. for 20 min in a microwave oven, the volatiles were removed and the crude material was purified by preparative HPLC to give 87 mg (62% yield) of the Boc-protected title compound. The material was treated with 4N HCl in dioxane (4 ml) for 1 h at ambient temperature and the volatiles were removed to give the pure title compound. LC-MS (method V): rt=1.94 min; m/z [M+H]+ 407/409.

Example 129

[4-(5-Allylamino-[1,3,4]oxadiazol-2-yl)-pyridin-3-yl]-(4-bromo-2-methyl-phenyl)-amine

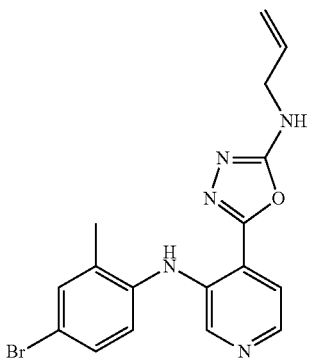 [SMILES: C=CCNc1nnc(-c2ccncc2Nc2ccc(Br)cc2C)o1]

Step 1: 3-(4-Bromo-2-methyl-phenylamino)-isonicotinic acid hydrazide was prepared from 3-[(4-bromo-2-methylphenyl)amino]isonicotinic acid (example 2) by the procedure as described for example 126 step 1.

Step 2: 3-(4-Bromo-2-methyl-phenylamino)-isonicotinic acid hydrazide (0.426 mmol) was dissolved in 5 ml THF and treated with allylisocyanate (110 mg, 0.852 mmol) followed by DIPEA (110 mg, 0.852 mmol) and the mixture was stirred for 2 h at ambient temperature. The volatiles were removed to give the crude compound, which was used for the next step.

Step 3: The product derived from step 2 was cyclized by the procedure described for example 127 step 2. LC-MS (method III): rt=6.99 min; m/z [M+H]+ 386/388.

Assay 1: MEK-1 Enzyme Assay (LANCE-HTRF)

The activity of the compounds of the present invitation may be determined by the following procedure: Inhibition of human MEK1 kinase activity was monitored with a homogenous, fluorescence based assay. The assay uses time resolved fluorescence resonance energy transfer to probe for phosphorylation of ERK1 by MEK1. The assay is carried out in low volume 96 well microtiter plates. In a total volume of 15 μl, compounds are incubated with 100 nM MEK1, 15 μM ATP, 300 nM ERK2 employing a buffer containing 20 mM TRIS/HCl, 10 mM MgCl2, 100 μM NaVO4, 1 mM DTT, and 0.005% Tween 20 (pH 7.4). After two hours, 5 nM Europium-anti-PY20 (Perkin Elmer) and 50 nM Anti-GST-Allophycocyanin (CisBio) in buffer containing 50 mM EDTA and 0.05% BSA are added and the reaction incubated for one hour in the dark. Time-resolved fluorescence is measured using a LJL-Analyst (Molecular Devices) with an excitation wavelength of 340 nm and an emission wavelength of 665 nm. The final concentration of DMSO is 2%. To assess the inhibitory potential of the compounds, IC50-values were determined.

In this assay compounds of the invention exhibited IC50s within certain ranges. The following compounds exemplify such activity with "+" meaning 1 μM<IC50≤10 μM and "++" IC≤1 μM. All results are shown in Table 1.

Assay 2: Tumor Cell Proliferation Assays (ATP Lite)

Murine colon C26, human melanoma A375 and Mel5 or human pancreatic MiaPaCa-2 cells were plated in 96 well Corning white plates (1500 cells/well for C26, and 2000 cells/well for A375, and MiaPaCa-2) and cultured overnight at 37° C. in 5% CO2. Inhibitors were serially diluted in 100% DMSO and subsequently added to cells to reach a final concentration of 0.25% DMSO. The cells were incubated for 4 days in the presence of test compounds in cell growth media (DMEM with 10% fetal bovine serum, 2 mM glutamine for C26, and MiaPaCa-2, and RPMI with 10% fetal bovine serum, 2 mM glutamine for A375). Cell proliferation was quantitated using the ATP lite cell proliferation kit (Packard). Inhibition of cell proliferation is shown in Table 1. Columns 4-6 show the concentration of compounds required to induce 50% cell death (IC50 in μM) of human endometriotic cells. With "+" meaning 3 μM<IC50≤10 μM and "++" IC50≤3 μM and "n.d." means not determined. Few compounds were also tested on human melanoma cell Mel5. Compound of Example #124 showed an IC50 of "++", the compound of Example 4 showed an IC50 of "+" and the compound of Example 5 showed an IC50 of "++".

Assay 3: Microsomal Stability Assay

Compounds were tested on their stability in human, rat and mouse liver microsomal preparations (HLM, RLM and MLM respectively). At a final concentration of 3 μM, compounds were incubated at 37° C. with 0.5 mg/ml human, rat or mouse liver microsomes in a buffer containing 50 mM phosphate, pH 7.4 and 2 mM NADPH. Pooled human liver microsomes or pooled male rat liver microsomes (Sprague Dawley) were obtained from NatuTec (Frankfurt, Germany). Incubations without NADPH served as negative controls. Reactions were stopped after 0, 15, 30, 45 or 60 min by the addition of acetonitrile and microsomes were pelleted by centrifugation (10 min at 6200×g). Supernatants were analyzed by HPLC regarding the concentration of mother compound. Finally, the half life of compounds in the regarding microsomal preparation was calculated. Results are shown in Table 2. Wherein "+" means $t_{1/2}$ of 1-30 min, "++" means $t_{1/2}$ of 31-120 min and "+++" means $t_{1/2}$ of >120 min.

Assay 4: Caco-2 Permeability Assay

Caco-2 cells obtained from the ATCC at passage number 27 are used. Cells (passage number 40-60) were seeded on to Millipore Multiscreen Caco-2 plates or Falcon HTS inserts at 1×105 cells/cm2. Cells were cultured for 20 days in DMEM and media was changed every two or three days. On day 20 the permeability study was performed.

Permeability was studied by applying compound to the apical surface of cell monolayers and measuring compound permeation into the basolateral compartment. The experiment was also performed in the reverse direction (B-A) to investigate active transport. Hanks Balanced Salt Solution (HBSS) pH 7.4 buffer with 25 mM HEPES and 10 mM glucose at 37° C. was used as the medium in permeability studies. Incubations were carried out in an atmosphere of 5% $CO_2$ with a relative humidity of 95%.

The monolayers were prepared by rinsing both basolateral and apical surfaces twice with HBSS at 37° C. Cells were then incubated with HBSS in both apical and basolateral compartments for 40 minutes to stabilize physiological parameters.

HBSS was then removed from the apical compartment and replaced with test compound dosing solutions. The solutions were made by diluting 10 mM DMSO concentrates with HBSS to give a final test compound concentration of 10 μM (final DMSO concentration adjusted to 1%). The fluorescent integrity marker lucifer yellow was also included in the dosing solution. Analytical standards were made from dosing solutions. Test compound permeability was assessed in duplicate. On each plate compounds of known permeability characteristics were run as controls.

The apical compartment inserts were then placed into 'companion' plates containing fresh HBSS. For basolateral to apical (B-A) experiments the experiment was initiated by replacing buffer in the inserts then placing them in companion plates containing dosing solutions. At 120 minutes the companion plate was removed and apical and basolateral samples diluted for analysis by LC-MS/MS (the donor compartment was also sampled to permit determination of starting concentration after non-specific binding has occurred).

Analysis

The integrity of the monolayers throughout the experiment is checked by monitoring lucifer yellow permeation using fluorimetric analysis. Lucifer yellow permeation was low if monolayers have not been damaged. Test and control compounds were quantified by LC-MS/MS cassette analysis using a 5-point calibration with appropriate dilution of the samples. Should lucifer yellow Papps were above QC limits in more than one well per test compound, the compound was re-tested.

The permeability coefficient for each compound ($P_{app}$) was calculated from the following equation:

$$P_{app} = [dQ/dt]/[C_0 \times A]$$

Whereby dQ/dt is the rate of permeation of the drug across the cells, $C_0$ is the donor compartment concentration at time zero and A is the area of the cell monolayer. $C_0$ is obtained from analysis of the donor compartment at the end of the incubation period.

Test compounds were grouped into low, medium or high absorption potential based on comparison with control compounds, which have known human absorption.

In addition, permeation was studied in both directions across the cells, and an asymmetry index was reported from mean A-B and B-A data. This was derived from:

$$P_{app(B-A)}/P_{app(A-B)}$$

Results are shown in Table 2. Wherein "+" means a caco A-B and caco B-A value of 1-10 and "++" means a caco A-B and caco B-A value of 11-100.

TABLE 1

Results of MEK enzyme assay and tumor cell proliferation assay

| Example # | MEK inhibition | IC50 [μM] C26 | IC50 [μM] A375 | IC50 [μM] Miapaca |
|---|---|---|---|---|
| 1 | ++ | | | |
| 2 | ++ | | | |
| 3 | ++ | | | |
| 4 | ++ | | ++ | n.d. |
| 5 | ++ | + | ++ | n.d. |
| 6 | + | | | |
| 7 | ++ | ++ | ++ | ++ |
| 8 | ++ | ++ | ++ | ++ |
| 9 | ++ | + | ++ | n.d. |
| 10 | ++ | + | ++ | ++ |
| 11 | ++ | ++ | ++ | ++ |
| 12 | ++ | ++ | ++ | ++ |
| 13 | ++ | ++ | ++ | ++ |
| 14 | ++ | ++ | ++ | ++ |
| 15 | ++ | ++ | ++ | ++ |
| 16 | ++ | ++ | ++ | ++ |
| 17 | ++ | ++ | ++ | ++ |
| 18 | ++ | ++ | ++ | ++ |
| 19 | ++ | + | ++ | ++ |
| 20 | ++ | ++ | ++ | ++ |
| 21 | ++ | + | ++ | + |
| 22 | ++ | ++ | ++ | ++ |
| 23 | ++ | ++ | ++ | ++ |
| 24 | ++ | ++ | ++ | ++ |
| 25 | ++ | ++ | ++ | ++ |
| 26 | ++ | + | ++ | + |
| 27 | ++ | + | + | + |
| 28 | ++ | + | ++ | + |
| 29 | ++ | + | ++ | + |
| 30 | ++ | ++ | ++ | ++ |
| 31 | ++ | ++ | ++ | ++ |
| 32 | ++ | ++ | ++ | ++ |
| 33 | ++ | ++ | ++ | ++ |
| 34 | ++ | + | ++ | + |
| 35 | ++ | ++ | ++ | ++ |
| 36 | ++ | ++ | ++ | ++ |
| 37 | ++ | n.d. | n.d. | n.d. |
| 38 | + | n.d. | n.d. | n.d. |
| 39 | ++ | ++ | ++ | ++ |
| 40 | ++ | + | ++ | + |
| 41 | ++ | ++ | ++ | ++ |
| 42 | ++ | + | ++ | + |
| 43 | ++ | + | ++ | + |
| 44 | ++ | + | ++ | + |
| 45 | ++ | + | ++ | + |
| 46 | ++ | + | ++ | + |
| 47 | ++ | ++ | ++ | ++ |
| 48 | ++ | ++ | ++ | ++ |
| 49 | ++ | ++ | ++ | ++ |
| 50 | ++ | + | ++ | + |
| 51 | ++ | + | ++ | ++ |
| 52 | + | n.d. | n.d. | n.d. |
| 53 | ++ | ++ | ++ | ++ |
| 54 | + | | + | |
| 55 | ++ | + | ++ | + |
| 56 | + | + | ++ | + |
| 57 | + | n.d. | n.d. | n.d. |
| 58 | ++ | ++ | ++ | ++ |
| 59 | + | n.d. | n.d. | n.d. |
| 60 | ++ | ++ | ++ | ++ |
| 61 | ++ | | + | |
| 62 | ++ | + | ++ | |
| 63 | ++ | | ++ | |
| 64 | ++ | + | ++ | + |
| 65 | ++ | + | ++ | + |
| 66 | ++ | | ++ | |
| 67 | ++ | ++ | ++ | ++ |
| 68 | ++ | ++ | ++ | ++ |
| 69 | ++ | + | ++ | |
| 70 | ++ | ++ | ++ | ++ |
| 71 | ++ | + | ++ | + |
| 72 | ++ | + | ++ | + |
| 73 | ++ | | | |
| 74 | ++ | + | ++ | + |
| 75 | ++ | ++ | ++ | ++ |
| 76 | ++ | + | ++ | + |
| 77 | ++ | + | ++ | + |
| 78 | ++ | + | ++ | |
| 79 | ++ | ++ | ++ | ++ |
| 80 | ++ | | ++ | + |
| 81 | ++ | + | ++ | + |
| 82 | ++ | + | ++ | + |
| 83 | ++ | ++ | ++ | ++ |
| 84 | ++ | + | ++ | |
| 85 | ++ | + | ++ | + |
| 86 | ++ | + | ++ | + |
| 87 | ++ | | ++ | + |
| 88 | ++ | + | + | + |
| 89 | + | n.d. | n.d. | n.d. |
| 90 | ++ | ++ | ++ | ++ |
| 91 | ++ | + | ++ | + |
| 92 | ++ | + | ++ | + |
| 93 | ++ | + | ++ | + |
| 94 | ++ | | + | |
| 95 | ++ | | | |
| 96 | ++ | ++ | ++ | ++ |
| 97 | ++ | ++ | ++ | ++ |
| 98 | ++ | + | ++ | + |
| 99 | ++ | + | ++ | + |
| 100 | ++ | + | ++ | + |
| 101 | ++ | + | ++ | + |
| 102 | ++ | + | ++ | + |
| 103 | ++ | n.d. | n.d. | n.d. |
| 104 | ++ | n.d. | n.d. | n.d. |
| 105 | ++ | n.d. | n.d. | n.d. |
| 106 | ++ | n.d. | n.d. | n.d. |
| 107 | ++ | n.d. | n.d. | n.d. |
| 108 | ++ | n.d. | n.d. | n.d. |
| 109 | ++ | n.d. | n.d. | n.d. |
| 110 | ++ | n.d. | n.d. | n.d. |
| 111 | ++ | n.d. | n.d. | n.d. |
| 112 | ++ | n.d. | n.d. | n.d. |
| 113 | ++ | n.d. | n.d. | n.d. |
| 114 | ++ | n.d. | n.d. | n.d. |
| 115 | ++ | n.d. | n.d. | n.d. |
| 116 | ++ | n.d. | n.d. | n.d. |
| 117 | n.d. | n.d. | n.d. | n.d. |
| 118 | + | n.d. | n.d. | n.d. |
| 119 | + | n.d. | n.d. | n.d. |
| 120 | | n.d. | n.d. | n.d. |
| 121 | ++ | n.d. | n.d. | n.d. |
| 122 | | n.d. | n.d. | n.d. |
| 123 | ++ | n.d. | n.d. | n.d. |
| 124 | ++ | + | n.d. | n.d. |
| 125 | ++ | n.d. | n.d. | n.d. |
| 126 | + | n.d. | n.d. | n.d. |
| 127 | | n.d. | n.d. | n.d. |
| 128 | ++ | n.d. | n.d. | n.d. |
| 129 | ++ | n.d. | n.d. | n.d. |

TABLE 2

Results of caco-2 permeability assay and microsomal stability assay

| Example # | HLM $t_{1/2}$ [min] | RLM $t_{1/2}$ [min] | MLM $t_{1/2}$ [min] | Caco A-B | Caco B-A |
|---|---|---|---|---|---|
| 4 | ++ | ++ | n.d. | n.d. | n.d. |
| 9 | +++ | +++ | +++ | + | ++ |
| 123 | ++ | + | n.d. | n.d. | n.d. |
| 127 | +++ | +++ | + | ++ | ++ |
| 128 | +++ | ++ | n.d. | ++ | ++ |
| 129 | +++ | ++ | +++ | ++ | ++ |

What is claimed is:

1. A method of treating a subject with a hyperproliferative disease comprising administering to the subject an effective amount of a MEK inhibitor, wherein the hyperproliferative disease is related to the hyperactivity of MEK and diseases modulated by the MEK cascade in mammals, and wherein the MEK inhibitor is a compound according to Formula (II):

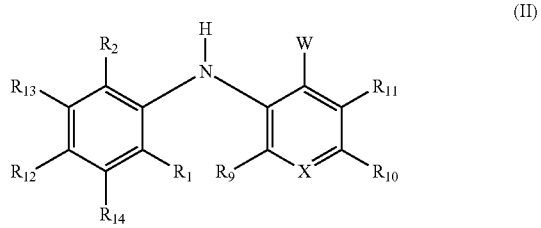

(II)

or a pharmaceutically acceptable salt thereof,
wherein:
$R_1$, $R_2$, $R_9$, $R_{10}$, $R_{11}$, $R_{12}$, $R_{13}$ and $R_{14}$ are independently selected from: hydrogen, halogen, cyano, nitro, azido, —$OR_3$, —$NR_4C(O)OR_6$, —$OC(O)R_3$, —$NR_4S(O)_jR_6$, —$S(O)_jNR_3R_4$ —$S(O)_jNR_4C(O)R_3$, —$C(O)NR_4S(O)_jR_6$, —$S(O)_jR_6$, —$NR_4C(O)R_3$, —$C(O)NR_3R_4$, —$NR_5C(O)NR_3R_4$, —$NR_5C(NCN)NR_3R_4$, —$NR_3R_4$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, or —$S(O)_j(C_1$-$C_6$ alkyl);
provided that $R_{12}$ is not OH, and $R_{13}$, $R_{14}$ are not $C_1$-$C_{10}$ alkyl;
$R_3$ is selected from hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl or $C_3$-$C_{10}$ cycloalkylalkyl, where each alkyl, alkenyl, alkynyl and cycloalkyl is unsubstituted or substituted with primary amino, aminocarbonyl, carboxyl, cyano, halogen, hydroxy, nitro or trihalomethyl;
$R_4$ is selected from hydrogen or $C_1$-$C_6$ alkyl, whereby alkyl may be unsubstituted or substituted with primary amino, aminocarbonyl, carboxyl, cyano, halogen, hydroxy, nitro or trihalomethyl;
$R_5$ is selected from hydrogen or $C_1$-$C_6$ alkyl, whereby alkyl may be unsubstituted or substituted with primary amino, aminocarbonyl, carboxyl, cyano, halogen, hydroxy, nitro or trihalomethyl;
$R_6$ is selected from trifluoromethyl, $C_1$-$C_{10}$ alkyl or $C_3$-$C_{10}$ cycloalkyl;
W is selected from —$C(O)OR_{15}$, —$C(O)NR_4R_{15}$, —$C(O)NR_4OR_{15}$, —$C(O)NR_4S(O)_jR_6$, —$C(O)NR_4NR_4R_{15}$, —NR'C(O)R', —NR'S(O)$_j$R', —NRC(O)NR'R", NR'S(O)$_j$NR'R", or —$C(O)NR_4NR_4C(O)R_{15}$;
provided that W is not —C(O)OH;
$R_{15}$ is independently selected from: hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, and heterocyclylalkyl; wherein each alkyl, alkenyl, alkynyl, cycloalkyl, aryl, heteroaryl and heterocyclyl is unsubstituted or substituted with primary amino, aminocarbonyl, carboxyl, cyano, halogen, hydroxy, nitro, trihalomethyl, O—$C_1$-$C_4$ alkyl or NR'R";
R' and R" are independently selected from hydrogen, $C_1$-$C_4$ alkyl, $C_2$-$C_4$ alkenyl, aryl and arylalkyl;
X is N or $N^+O^-$; and
j is 1 or 2, with the proviso that 3-Phenylamino-isonicotinic acid methyl ester and 3-Oxo-3-(3-phenylamino-pyridin-4-yl)-propionic acid ethyl ester are not included.

2. The method according to claim 1, wherein the disease is selected from the group consisting of cancer, inflammation, pancreatitis or kidney disease, pain, benign hyperplasia of the skin, restenosis, prostate, diseases related to vasculogenesis or angiogenesis, tumor angiogenesis, skin diseases selected from psoriasis, eczema, and sclerodema, diabetes, diabetic retinopathy, retinopathy of prematurity, age-related macular degeneration, hemangioma, glioma, melanoma and Kaposi's sarcoma.

3. The method according to claim 2, wherein the disease is cancer or inflammation.

4. The method according to claim 2, wherein the cancer is selected from the group consisting of ovarian, breast, lung, pancreatic, prostate, colon, melanoma and epidermoid cancer.

5. The method according to claim 3, wherein the inflammation is selected from the group consisting of rheumatoid arthritis, inflammatory bowel disease and atherosclerosis.

6. A method of treating a subject with a hyperproliferative disease comprising administering to the subject an effective amount of a pharmaceutical composition comprising an MEK inhibitor and a pharmaceutically acceptable excipient, wherein the hyperproliferative disease is related to the hyperactivity of MEK and diseases modulated by the MEK cascade in mammals, and wherein the MEK inhibitor is a compound of Formula (II):

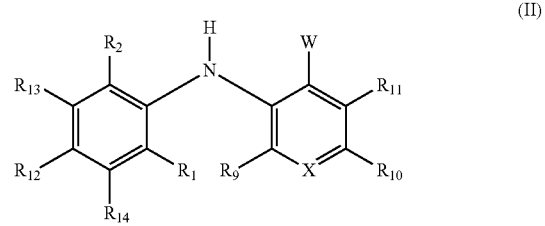

(II)

or a pharmaceutically acceptable salt thereof,
wherein:
$R_1$, $R_2$, $R_9$, $R_{10}$, $R_{11}$, $R_{12}$, $R_{13}$ and $R_{14}$ are independently selected from: hydrogen, halogen, cyano, nitro, azido, —$OR_3$, —$NR_4C(O)OR_6$, —$OC(O)R_3$, —$NR_4S(O)_jR_6$, —$S(O)_jNR_3R_4$ —$S(O)_jNR_4C(O)R_3$, —$C(O)NR_4S(O)_jR_6$,—$S(O)_jR_6$, —$NR_4C(O)R_3$, —$C(O)NR_3R_4$, —$NR_5C(O)NR_3R_4$, —$NR_5C(NCN)NR_3R_4$, —$NR_3R_4$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, or —$S(O)_j(C_1$-$C_6$ alkyl);
provided that $R_{12}$ is not OH, and $R_{13}$, $R_{14}$ are not $C_1$-$C_{10}$ alkyl;

$R_3$ is selected from hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl or $C_3$-$C_{10}$ cycloalkylalkyl, where each alkyl, alkenyl, alkynyl and cycloalkyl is unsubstituted or substituted with primary amino, aminocarbonyl, carboxyl, cyano, halogen, hydroxy, nitro or trihalomethyl;

$R_4$ is selected from hydrogen or $C_1$-$C_6$ alkyl, whereby alkyl may be unsubstituted or substituted with primary amino, aminocarbonyl, carboxyl, cyano, halogen, hydroxy, nitro or trihalomethyl;

$R_5$ is selected from hydrogen or $C_1$-$C_6$ alkyl, whereby alkyl may be unsubstituted or substituted with primary amino, aminocarbonyl, carboxyl, cyano, halogen, hydroxy, nitro or trihalomethyl;

$R_6$ is selected from trifluoromethyl, $C_1$-$C_{10}$ alkyl or $C_3$-$C_{10}$ cycloalkyl;

W is selected from —C(O)OR$_{15}$, —C(O)NR$_4$R$_{15}$, —C(O)NR$_4$OR$_{15}$, —C(O)NR$_4$S(O)$_j$R$_6$, —C(O)NR$_4$NR$_4$R$_{15}$, —NR'C(O)R', —NR'S(O)$_j$R', —NRC(O)NR'R", NR'S(O)$_j$NR'R", or —C(O)NR$_4$NR$_4$C(O)R$_{15}$;

provided that W is not —C(O)OH;

$R_{15}$ is independently selected from: hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, and heterocyclylalkyl; wherein each alkyl, alkenyl, alkynyl, cycloalkyl, aryl, heteroaryl and heterocyclyl is unsubstituted or substituted with primary amino, aminocarbonyl, carboxyl, cyano, halogen, hydroxy, nitro, trihalomethyl, O—$C_1$-$C_4$ alkyl or NR'R";

R' and R" are independently selected from hydrogen, $C_1$-$C_4$ alkyl, $C_2$-$C_4$ alkenyl, aryl and arylalkyl;

X is N or N$^+$O$^-$; and j is 1 or 2, with the proviso that 3-Phenylamino-isonicotinic acid methyl ester and 3-Oxo-3-(3-phenylamino-pyridin-4-yl)-propionic acid ethyl ester are not included.

7. The method according to claim 6, wherein the disease is selected from the group consisting of cancer, inflammation, pancreatitis or kidney disease, pain, benign hyperplasia of the skin, restenosis, prostate, diseases related to vasculogenesis or angiogenesis, tumor angiogenesis, skin diseases selected from psoriasis, eczema, and sclerodema, diabetes, diabetic retinopathy, retinopathy of prematurity, age-related macular degeneration, hemangioma, glioma, melanoma and Kaposi's sarcoma.

8. The method according to claim 7, wherein the disease is cancer or inflammation.

9. The method according to claim 7, wherein the cancer is selected from the group consisting of ovarian, breast, lung, pancreatic, prostate, colon, melanoma and epidermoid cancer.

10. The method according to claim 8, wherein the inflammation is selected from the group consisting of rheumatoid arthritis, inflammatory bowel disease and atherosclerosis.

11. A method of treating a subject with a hyperproliferative disease comprising administering to the subject an effective amount of a MEK inhibitor, wherein the hyperproliferative disease is cancer, and wherein the MEK inhibitor is a compound according to Formula (II):

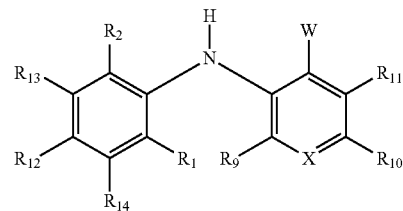

(II)

or a pharmaceutically acceptable salt thereof, wherein:

$R_1$, $R_2$, $R_9$, $R_{10}$, $R_{11}$, $R_{12}$, $R_{13}$ and $R_{14}$ are independently selected from: hydrogen, halogen, cyano, nitro, azido, —OR$_3$, —NR$_4$C(O)OR$_6$, —OC(O)R$_3$, —NR$_4$S(O)$_j$R$_6$, —S(O)$_j$NR$_3$R$_4$, —S(O)$_j$NR$_4$C(O)R$_3$, —C(O)NR$_4$S(O)$_j$R$_6$, —S(O)$_j$R$_6$, —NR$_4$C(O)R$_3$, —C(O)NR$_3$R$_4$, —NR$_5$C(O)NR$_3$R$_4$, —NR$_5$C(NCN)NR$_3$R$_4$, —NR$_3$R$_4$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, or —S(O)$_j$($C_1$-$C_6$ alkyl);

provided that $R_{12}$ is not OH, and $R_{13}$, $R_{14}$ are not $C_1$-$C_{10}$ alkyl;

$R_3$ is selected from hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl or $C_3$-$C_{10}$ cycloalkylalkyl, where each alkyl, alkenyl, alkynyl and cycloalkyl is unsubstituted or substituted with primary amino, aminocarbonyl, carboxyl, cyano, halogen, hydroxy, nitro or trihalomethyl;

$R_4$ is selected from hydrogen or $C_1$-$C_6$ alkyl, whereby alkyl may be unsubstituted or substituted with primary amino, aminocarbonyl, carboxyl, cyano, halogen, hydroxy, nitro or trihalomethyl;

$R_5$ is selected from hydrogen or $C_1$-$C_6$ alkyl, whereby alkyl may be unsubstituted or substituted with primary amino, aminocarbonyl, carboxyl, cyano, halogen, hydroxy, nitro or trihalomethyl;

$R_6$ is selected from trifluoromethyl, $C_1$-$C_{10}$ alkyl or $C_3$-$C_{10}$ cycloalkyl;

W is selected from —C(O)OR$_{15}$, —C(O)NR$_4$R$_{15}$, —C(O)NR$_4$OR$_{15}$, —C(O)NR$_4$S(O)$_j$R$_6$, —C(O)NR$_4$NR$_4$R$_{15}$, —NR'C(O)R', —NR'S(O)$_j$R', —NRC(O)NR'R", NR'S(O)$_j$NR'R", or —C(O)NR$_4$NR$_4$C(O)R$_{15}$;

provided that W is not —C(O)OH;

$R_{15}$ is independently selected from: hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, and heterocyclylalkyl; wherein each alkyl, alkenyl, alkynyl, cycloalkyl, aryl, heteroaryl and heterocyclyl is unsubstituted or substituted with primary amino, aminocarbonyl, carboxyl, cyano, halogen, hydroxy, nitro, trihalomethyl, O—$C_1$-$C_4$ alkyl or NR'R";

R' and R" are independently selected from hydrogen, $C_1$-$C_4$ alkyl, $C_2$-$C_4$ alkenyl, aryl and arylalkyl;

X is N or N$^+$O$^-$; and j is 1 or 2, with the proviso that 3-Phenylamino-isonicotinic acid methyl ester and 3-Oxo-3-(3-phenylamino-pyridin-4-yl)-propionic acid ethyl ester are not included.

12. The method according to claim 11, wherein the cancer is selected from the group consisting of ovarian, breast, lung, pancreatic, prostate, colon and epidermoid cancer.

13. The method according to claim 11, wherein the MEK inhibitor is provided in a pharmaceutical composition comprising the MEK inhibitor and a pharmaceutically acceptable excipient.

14. A method of inhibiting hyperactivity of MEK in a cell, comprising administering to the cell an effective amount of a MEK inhibitor, wherein the MEK inhibitor is a compound according to Formula (II):

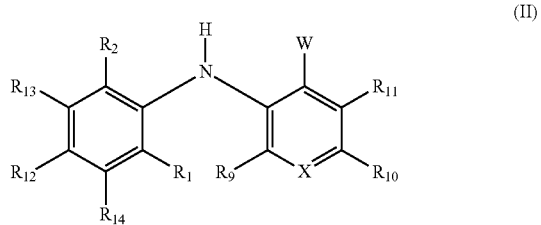

or a pharmaceutically acceptable salt thereof,
wherein:
- $R_1$, $R_2$, $R_9$, $R_{10}$, $R_{11}$, $R_{12}$, $R_{13}$ and $R_{14}$ are independently selected from: hydrogen, halogen, cyano, nitro, azido, —$OR_3$, —$NR_4C(O)OR_6$, —$OC(O)R_3$, —$NR_4S(O)_jR_6$, —$S(O)_jNR_3R_4$, —$S(O)_jNR_4C(O)R_3$, —$C(O)NR_4S(O)_jR_6$, —$S(O)_jR_6$, —$NR_4C(O)R_3$, —$C(O)NR_3R_4$, —$NR_5C(O)NR_3R_4$, —$NR_5C(NCN)NR_3R_4$, —$NR_3R_4$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, or —$S(O)_j(C_1$-$C_6$ alkyl);
- provided that $R_{12}$ is not OH, and $R_{13}$, $R_{14}$ are not $C_1$-$C_{10}$ alkyl;
- $R_3$ is selected from hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl or $C_3$-$C_{10}$ cycloalkylalkyl, where each alkyl, alkenyl, alkynyl and cycloalkyl is unsubstituted or substituted with primary amino, aminocarbonyl, carboxyl, cyano, halogen, hydroxy, nitro or trihalomethyl;
- $R_4$ is selected from hydrogen or $C_1$-$C_6$ alkyl, whereby alkyl may be unsubstituted or substituted with primary amino, aminocarbonyl, carboxyl, cyano, halogen, hydroxy, nitro or trihalomethyl;
- $R_5$ is selected from hydrogen or $C_1$-$C_6$ alkyl, whereby alkyl may be unsubstituted or substituted with primary amino, aminocarbonyl, carboxyl, cyano, halogen, hydroxy, nitro or trihalomethyl;
- $R_6$ is selected from trifluoromethyl, $C_1$-$C_{10}$ alkyl or $C_3$-$C_{10}$ cycloalkyl;
- W is selected from —$C(O)OR_{15}$, —$C(O)NR_4R_{15}$, —$C(O)NR_4OR_{15}$, —$C(O)NR_4S(O)_jR_6$, —$C(O)NR_4NR_4R_{15}$, —NR'C(O)R', —NR'S(O)_jR', —NRC(O)NR'R", NR'S(O)_jNR'R", or —$C(O)NR_4NR_4C(O)R_{15}$;
- provided that W is not —C(O)OH;
- $R_{15}$ is independently selected from: hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl, and heterocyclylalkyl; wherein each alkyl, alkenyl, alkynyl, cycloalkyl, aryl, heteroaryl and heterocyclyl is unsubstituted or substituted with primary amino, aminocarbonyl, carboxyl, cyano, halogen, hydroxy, nitro, trihalomethyl, O—$C_1$-$C_4$ alkyl or NR'R";
- R' and R" are independently selected from hydrogen, $C_1$-$C_4$ alkyl, $C_2$-$C_4$ alkenyl, aryl and arylalkyl;
- X is N or $N^{+O-}$; and
- j is 1 or 2, with the proviso that 3-Phenylamino-isonicotinic acid methyl ester and 3-Oxo-3-(3-phenylamino-pyridin-4-yl)-propionic acid ethyl ester are not included.

15. The method according to claim 1, wherein:
- $R_1$, $R_2$, $R_9$, $R_{10}$, $R_{11}$, $R_{12}$, $R_{13}$ and $R_{14}$ are independently selected from hydrogen, halogen, cyano, nitro, azido, —$OR_3$, —$NR_4C(O)OR_6$, —$OC(O)R_3$, —$NR_4S(O)_jR_6$, —$S(O)_jNR_3R_4$, —$S(O)_jNR_4C(O)R_3$, —$C(O)NR_4S(O)_jR_6$, $S(O)_jR_6$, —$NR_4C(O)R_3$, —$C(O)NR_3R_4$, —$NR_5C(O)NR_3R_4$, —$NR_5C(NCN)NR_3R_4$, —$NR_3R_4$, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl or —$S(O)j(C1$-$C6$ alkyl);
- provided that $R_{12}$ is not OH, and $R_{13}$, $R_{14}$ are not $C_1$-$C_{10}$ alkyl;
- $R_3$ is selected from hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl or $C_3$-$C_{10}$ cycloalkylalkyl, where each alkyl, alkenyl, alkynyl and cycloalkyl is unsubstituted or substituted with primary amino, aminocarbonyl, carboxyl, cyano, halogen, hydroxy, nitro or trihalomethyl;
- $R_4$ is selected from hydrogen or $C_1$-$C_6$ alkyl, whereby alkyl may be unsubstituted or substituted with primary amino, aminocarbonyl, carboxyl, cyano, halogen, hydroxy, nitro or trihalomethyl;
- $R_5$ is selected from hydrogen or $C_1$-$C_6$ alkyl, whereby alkyl may be unsubstituted or substituted with primary amino, aminocarbonyl, carboxyl, cyano, halogen, hydroxy, nitro or trihalomethyl;
- $R_6$ is selected from trifluoromethyl, $C_1$-$C_{10}$ alkyl or $C_3$-$C_{10}$ cycloalkyl;
- W is —$C(O)OR_{15}$, —$C(O)NR_4R_{15}$, —$C(O)NR_4OR_{15}$ or —$C(O)NR_4S(O)_jR_6$;
- provided that W is not C(O)OH;
- $R_{15}$ is independently selected from hydrogen, trifluoromethyl, $C_1$-$C_{10}$ alkyl, $C_2$-$C_{10}$ alkenyl, $C_2$-$C_{10}$ alkynyl, $C_3$-$C_{10}$ cycloalkyl, $C_3$-$C_{10}$ cycloalkylalkyl, aryl, arylalkyl, heteroaryl, heteroarylalkyl, heterocyclyl or heterocyclylalkyl, where each alkyl, alkenyl, alkynyl, cycloalkyl, aryl, heteroaryl and heterocyclyl is unsubstituted or substituted with primary amino, aminocarbonyl, carboxyl, cyano, halogen, hydroxy, nitro, trihalomethyl, O—$C_1$-$C_4$ alkyl or NR'R";
- R' and R" are independently selected from hydrogen, $C_1$-$C_4$ alkyl, $C_2$-$C_4$ alkenyl, aryl or arylalkyl;
- X is N or $N^{+}O^{-}$; and
- j is 1 or 2.

16. The method according to claim 1, wherein:
- $R_1$, $R_2$, $R_9$ and $R_{11}$ are independently selected from hydrogen, halo, $C_1$-$C_4$ alkyl, $C_3$-$C_4$ cycloalkyl, $C_2$-$C_4$ alkenyl, $C_2$-$C_4$ alkynyl, cyano, nitro, $OR_3$ or $NR_3R_4$, where each alkyl, alkenyl, alkynyl, cycloalkyl is optionally substituted with one to five halogens;
- $R_{10}$ and $R_{12}$ are independently selected from hydrogen, halo, $C_1$-$C_{10}$ alkyl, $C_3$-$C_{10}$ cycloalkyl, $C_2$-$C_{10}$ alkenyl, $C_2$-$C_{10}$ alkynyl, cyano, nitro, azido, $NR_4SO_2R_6$, $SO_2NR_3R_4$, $SO_2R_6$, $C(O)NR_3R_4$, —$S(O)_jNR_4C(O)R_3$, —$C(O)NR_4S(O)_jR_6$, $OR_3$, $NR_3R_4$ or —$S(C_1$-$C_2$ alkyl) substituted with 1 to 5 F;
- $R_{13}$ and $R_{14}$ are independently selected from H, F, Cl, $C_1$-$C_4$ alkyl, $C_3$-$C_4$ cycloalkyl, $C_2$-$C_4$ alkenyl or $C_2$-$C_4$ alkynyl, where each alkyl, alkenyl, cycloalky, alkynyl is optionally substituted with one to five halogens;
- W is —$C(O)OR_{15}$, —$C(O)NR_4R_{15}$, —$C(O)NR_4OR_{15}$, —$C(O)(C_2$-$C_{10}$ alkyl) or —$C(O)NR_4S(O)_jR_6$;
- $R_{15}$ is selected from hydrogen, $C_1$-$C_4$ alkyl, $C_1$-$C_4$ alkenyl or $C_4$-$C_6$ cycloalkylalkyl, where alkyl or alkenyl is optionally substituted by 1 or 2 of OH, O—$C_1$-$C_4$ alkyl or NR'R"; and R' and R" are each independently selected from hydrogen, $C_1$-$C_4$ alkyl, $C_2$-$C_4$ alkenyl, aryl or arylalkyl.

17. The method according to claim 1, wherein:

$R_1$ is independently selected from H and F;

$R_2$ is independently selected from hydrogen, F, Cl or Me, where the methyl group is optionally substituted with one to three fluorines;

$R_9$ is independently selected from H, F or Cl;

$R_{10}$ is independently selected from H, F, Cl, Br, nitro, Me or OMe, where the methyl groups are optionally substituted with one to three fluorines, $SO_2NR_3R_4$ or $C(O)NR_3R_4$, wherein $R_3$ and $R_4$ are independently $C_1$-$C_6$ alkyl, optionally substituted by 1 or 2 alkyl amino or O-alkyl, or $R_3$ and $R_4$ taken together form a cyclic ring with 1 or 2 N atoms and optionally an O atom, said ring being optionally substituted by 1 or 2 alkyl amino or O-alkyl;

$R_{11}$ is independently selected from H, F, Cl, Br, Me or OMe, where the methyl groups are optionally substituted with one to three fluorines;

$R_{12}$ is independently selected from H, F, Cl, Br, nitro, Me, $SCF_3$, $SCHF_2$, $SCH_2F$, $SO_2NR_3R_4$, $C(O)NR_3R_4$ or OMe, where the methyl groups are optionally substituted with one to three fluorines, wherein $R_3$ and $R_4$ are independently $C_1$-$C_6$ alkyl, optionally substituted by 1 or 2 alkyl amino or O-alkyl, or $R_3$ and $R_4$ taken together form a cyclic ring with 1 or 2 N atoms and optionally an O atom, said ring being optionally substituted by 1 or 2 alkyl amino or O-alkyl;

$R_{13}$ is independently selected from H and F;

$R_{14}$ is independently selected from H and F;

W is —$C(O)NR_4OR_{15}$; and $R_{15}$ is $C_1$-$C_4$ alkyl or $C_1$-$C_4$ alkenyl optionally substituted with 1 to 3 substituents OH, O-Me, $NH_2$, N(methyl)$_2$ or N(ethyl)$_2$.

18. The method according to claim 1, wherein:

W is —$C(O)NR_4OR_{15}$;

$R_4$ is hydrogen;

$R_{15}$ is selected from $C_1$-$C_4$ alkyl or $C_1$-$C_4$ alkenyl that may be further substituted by 1 or 2 of OH, O—$C_1$-$C_4$ alkyl or NR'R"; and R' and R" are independently hydrogen, methyl or ethyl.

* * * * *